US012605205B2

(12) United States Patent
Cook et al.

(10) Patent No.: US 12,605,205 B2
(45) Date of Patent: Apr. 21, 2026

(54) ACTIVE ALIGNMENT SYSTEM AND METHOD FOR OPTIMIZING OPTICAL COUPLING OF MULTIPLEXER FOR LASER-DRIVEN INTRAVASCULAR LITHOTRIPSY DEVICE

(71) Applicant: BOSTON SCIENTIFIC SCIMED, INC., Maple Grove, MN (US)

(72) Inventors: Christopher A. Cook, Laguna Niguel, CA (US); Gerald D. Bacher, Carlsbad, CA (US); John F. Black, Bainbridge Island, WA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 0 days.

(21) Appl. No.: 18/500,757

(22) Filed: Nov. 2, 2023

(65) Prior Publication Data
US 2024/0058060 A1     Feb. 22, 2024

Related U.S. Application Data

(63) Continuation of application No. 17/308,934, filed on May 5, 2021, now abandoned.
(Continued)

(51) Int. Cl.
*A61B 18/20*          (2006.01)
*A61B 18/24*          (2006.01)
(Continued)

(52) U.S. Cl.
CPC .. *A61B 18/245* (2013.01); *A61B 2018/00369* (2013.01); *A61B 2018/208* (2013.01); *A61B 2018/2272* (2013.01)

(58) Field of Classification Search
CPC .... A61B 18/20; A61B 18/24–26; A61N 5/06; A61F 9/008
See application file for complete search history.

(56) References Cited

U.S. PATENT DOCUMENTS 4,649,924 A     3/1987   Taccardi
4,699,147 A     10/1987  Chilson et al.
(Continued)

FOREIGN PATENT DOCUMENTS

AU     2017205323     7/2017
AU     2022227829     9/2022
(Continued)

OTHER PUBLICATIONS

Davletshin, Yevgeniy R., "A Computational Analysis of Nanoparticle-Mediated Optical Breakdown", A dissertation presented to Ryerson University in Partial Fulfillment of the requirements for the degree of Doctor of Philosophy in the Program of Physics, Toronto, Ontario, CA 2017.
(Continued)

*Primary Examiner* — Lynsey C Eiseman
(74) *Attorney, Agent, or Firm* — SEAGER, TUFTE & WICKHEM, LLP

(57)          ABSTRACT

A catheter system (100) for treating a treatment site (106) includes a first light source (124), a plurality of light guides (122A), a multiplexer (128), a multiplexer alignment system (142), and a first beamsplitter (268). The first light source (124) generates a source beam (124A). The multiplexer (128) receives the source beam (124A), and alternatively directs the source beam (124A) to each of the plurality of light guides (122A). The multiplexer alignment system (142) is operatively coupled to the multiplexer (128). The multiplexer alignment system (142) includes a second light source (270) that generates a probe source beam (270A) that is directed to scan across a guide proximal end (122P) of
(Continued)

each of the plurality of light guides (122A) so that a time is determined to generate the source beam (124A) so that the source beam (124A) is optically coupled to the guide proximal end (122P) of each of the plurality of light guides (122A). The first beamsplitter (268) receives the source beam (124A) and the probe source beam (270A), and alternately directs the probe source beam (270A) and the source beam (124A) toward the guide proximal end (122P) of each of the plurality of light guides (122A).

20 Claims, 8 Drawing Sheets

Related U.S. Application Data

(60) Provisional application No. 63/023,669, filed on May 12, 2020.

(51) Int. Cl.
    *A61B 18/00*      (2006.01)
    *A61B 18/22*      (2006.01)

(56)              References Cited

U.S. PATENT DOCUMENTS

| | | |
|---|---|---|
| 4,799,479 A | 1/1989 | Spears |
| 4,850,351 A | 7/1989 | Herman |
| 4,913,142 A | 4/1990 | Kittrell et al. |
| 4,932,954 A | 6/1990 | Wondrazek et al. |
| 4,955,895 A | 9/1990 | Suglyama |
| 4,960,108 A | 10/1990 | Reichel et al. |
| 4,994,059 A | 2/1991 | Kosa et al. |
| 4,998,930 A | 3/1991 | Lundahl |
| 5,019,075 A | 5/1991 | Spears et al. |
| 5,034,010 A | 7/1991 | Kittrell et al. |
| 5,041,121 A | 8/1991 | Wondrazek et al. |
| 5,057,106 A | 10/1991 | Kasevich et al. |
| 5,082,343 A | 1/1992 | Coult et al. |
| 5,093,877 A | 3/1992 | Aita et al. |
| 5,104,391 A | 4/1992 | Ingle |
| 5,104,392 A | 4/1992 | Kittrell et al. |
| 5,109,452 A | 4/1992 | Selvin et al. |
| 5,116,227 A | 5/1992 | Levy |
| 5,125,404 A | 6/1992 | Kittrell et al. |
| 5,126,165 A | 6/1992 | Akihama et al. |
| 5,152,768 A | 10/1992 | Bhatta |
| 5,173,049 A | 12/1992 | Levy |
| 5,176,674 A | 1/1993 | Hofmann |
| 5,181,921 A | 1/1993 | Makita et al. |
| 5,188,632 A | 2/1993 | Goldenberg |
| 5,200,838 A | 4/1993 | Nudelman |
| 5,269,777 A | 12/1993 | Doiron |
| 5,290,277 A | 3/1994 | Vercimak et al. |
| 5,324,282 A | 6/1994 | Dodick |
| 5,328,472 A | 7/1994 | Steinke et al. |
| 5,336,184 A | 8/1994 | Teirstein |
| 5,363,458 A | 11/1994 | Pan |
| 5,372,138 A | 12/1994 | Crowley |
| 5,387,225 A | 2/1995 | Euteneur |
| 5,400,428 A | 3/1995 | Grace |
| 5,410,797 A | 5/1995 | Steinke et al. |
| 5,417,689 A | 5/1995 | Fine |
| 5,422,926 A | 6/1995 | Smith |
| 5,431,647 A | 7/1995 | Purcell |
| 5,454,809 A | 10/1995 | Janssen |
| 5,456,680 A | 10/1995 | Taylor |
| 5,474,537 A | 12/1995 | Solar |
| 5,496,311 A | 3/1996 | Abele et al. |
| 5,509,917 A | 4/1996 | Cecchetti |
| 5,519,798 A | 5/1996 | Shahid et al. |
| 5,540,679 A | 7/1996 | Fram |
| 5,562,657 A | 10/1996 | Griffin |
| 5,598,494 A | 1/1997 | Behrmann et al. |

| | | | | |
|---|---|---|---|---|
| 5,609,606 A | 3/1997 | O'Boyle | | |
| 5,611,807 A | 3/1997 | O'Boyle | | |
| 5,637,877 A | 6/1997 | Sinofsky | | |
| 5,661,829 A | 8/1997 | Zheng | | |
| 5,697,377 A | 12/1997 | Wittkamph | | |
| 5,718,241 A | 2/1998 | Ben-Haim et al. | | |
| 5,729,583 A | 3/1998 | Tang | | |
| 5,764,843 A | 6/1998 | Macken et al. | | |
| 5,772,609 A | 6/1998 | Nguyen et al. | | |
| 5,860,974 A | 1/1999 | Abele | | |
| 5,891,135 A | 4/1999 | Jackson et al. | | |
| 5,906,611 A | 5/1999 | Dodick et al. | | |
| 5,944,697 A | 8/1999 | Benett et al. | | |
| 6,007,514 A | 12/1999 | Nita | | |
| 6,015,404 A | 1/2000 | Altshuler | | |
| 6,080,119 A | 6/2000 | Schwarze et al. | | |
| 6,123,923 A | 9/2000 | Unger | | |
| 6,139,510 A | 10/2000 | Palermo | | |
| 6,186,963 B1 | 2/2001 | Schwarze et al. | | |
| 6,203,537 B1 | 3/2001 | Adrian | | |
| 6,210,404 B1 | 4/2001 | Shadduck | | |
| 6,339,470 B1 | 1/2002 | Papademetriou et al. | | |
| 6,356,575 B1 | 3/2002 | Fukumoto | | |
| 6,368,318 B1 | 4/2002 | Visuri et al. | | |
| 6,423,055 B1 | 7/2002 | Farr | | |
| 6,500,174 B1 | 12/2002 | Maguire et al. | | |
| 6,514,203 B2 | 2/2003 | Bukshpan | | |
| 6,514,249 B1 | 2/2003 | Maguire | | |
| 6,524,251 B2 | 2/2003 | Rabiner et al. | | |
| 6,538,739 B1* | 3/2003 | Visuri | ......... | G01N 21/431 |
| | | | | 356/497 |
| 6,544,218 B1 | 4/2003 | Choi | | |
| 6,548,010 B1 | 4/2003 | Stivland et al. | | |
| 6,560,387 B1 | 5/2003 | Hehlen et al. | | |
| 6,607,502 B1 | 8/2003 | Maguire et al. | | |
| 6,631,220 B1 | 10/2003 | Liang et al. | | |
| 6,652,547 B2 | 11/2003 | Rabiner et al. | | |
| 6,666,834 B2 | 12/2003 | Restle et al. | | |
| 6,702,781 B1 | 3/2004 | Reifart et al. | | |
| 6,773,447 B2 | 8/2004 | Laguna | | |
| 6,824,554 B1 | 11/2004 | Jang | | |
| 6,849,994 B1 | 2/2005 | White et al. | | |
| 6,890,317 B2 | 5/2005 | Gerdts et al. | | |
| 6,947,785 B1 | 9/2005 | Beatty et al. | | |
| 6,966,890 B2 | 11/2005 | Coyle et al. | | |
| 6,978,168 B2 | 12/2005 | Beatty et al. | | |
| 6,990,370 B1 | 1/2006 | Beatty et al. | | |
| 7,273,470 B2 | 9/2007 | Wantink | | |
| 7,309,324 B2 | 12/2007 | Hayes et al. | | |
| 7,367,967 B2 | 5/2008 | Eidenschink | | |
| 7,470,240 B2 | 12/2008 | Schultheiss et al. | | |
| 7,539,231 B1 | 5/2009 | Honea et al. | | |
| 7,569,032 B2 | 8/2009 | Naimark et al. | | |
| 7,599,588 B2 | 10/2009 | Eberle et al. | | |
| 7,641,646 B2 | 1/2010 | Kennedy, II | | |
| 7,691,079 B2 | 4/2010 | Gobel | | |
| 7,713,260 B2 | 5/2010 | Lessard | | |
| 7,758,572 B2 | 7/2010 | Weber et al. | | |
| 7,762,984 B2 | 7/2010 | Kumoyama et al. | | |
| 7,810,395 B2 | 10/2010 | Zhou | | |
| 7,850,685 B2 | 12/2010 | Kunis et al. | | |
| 7,867,178 B2 | 1/2011 | Simnacher | | |
| 7,909,797 B2 | 3/2011 | Kennedy, II et al. | | |
| 7,942,850 B2 | 5/2011 | Levit et al. | | |
| 7,967,781 B2 | 6/2011 | Simpson et al. | | |
| 7,972,299 B2 | 7/2011 | Carter | | |
| 7,985,189 B1 | 7/2011 | Ogden et al. | | |
| 8,021,328 B2 | 9/2011 | Lee | | |
| 8,029,473 B2 | 10/2011 | Carter | | |
| 8,043,256 B2 | 10/2011 | Hansen | | |
| 8,066,732 B2 | 11/2011 | Paul et al. | | |
| 8,088,121 B2 | 1/2012 | Nishide | | |
| 8,157,760 B2 | 4/2012 | Criado et al. | | |
| 8,162,859 B2 | 4/2012 | Schultheiss et al. | | |
| 8,166,825 B2 | 5/2012 | Zhou | | |
| 8,192,368 B2 | 6/2012 | Woodruff | | |
| 8,197,505 B2 | 6/2012 | Hirszowicz et al. | | |
| 8,246,643 B2 | 8/2012 | Nita | | |
| 8,267,886 B2 | 9/2012 | Ewing | | |

(56)  References Cited

U.S. PATENT DOCUMENTS

| | | | |
|---|---|---|---|
| 8,292,913 B2 | 10/2012 | Warnack | |
| 8,328,820 B2 | 12/2012 | Diamant | |
| 8,364,235 B2 | 1/2013 | Kordis et al. | |
| 8,372,034 B2 | 2/2013 | Levit | |
| 8,382,738 B2 | 2/2013 | Simpson et al. | |
| 8,414,527 B2 | 4/2013 | Mallaby | |
| 8,419,613 B2 | 4/2013 | Saadat | |
| 8,439,890 B2 | 5/2013 | Beyar | |
| 8,556,813 B2 | 10/2013 | Cashman et al. | |
| 8,556,851 B2 | 10/2013 | Hirszowicz | |
| 8,574,247 B2 | 11/2013 | Adams et al. | |
| 8,657,814 B2 | 2/2014 | Werneth | |
| 8,709,075 B2 | 4/2014 | Adams et al. | |
| 8,728,091 B2 | 5/2014 | Hakala et al. | |
| 8,734,424 B2 | 5/2014 | Watanabe | |
| 8,747,416 B2 | 6/2014 | Hakala et al. | |
| 8,784,362 B2 | 7/2014 | Boutilette | |
| 8,834,510 B2 | 9/2014 | Wilson et al. | |
| 8,888,788 B2 | 11/2014 | Hakala et al. | |
| 8,956,371 B2 | 2/2015 | Hawkins et al. | |
| 8,956,374 B2 | 2/2015 | Hawkins et al. | |
| 8,986,339 B2 | 3/2015 | Warnack | |
| 8,992,519 B2 | 3/2015 | Kim et al. | |
| 8,992,817 B2 | 3/2015 | Stamberg | |
| 9,005,216 B2 | 4/2015 | Hakala et al. | |
| 9,011,462 B2 | 4/2015 | Adams et al. | |
| 9,011,463 B2 | 4/2015 | Adams et al. | |
| 9,011,511 B2 | 4/2015 | Gregorich | |
| 9,044,575 B2 | 6/2015 | Beasley et al. | |
| 9,044,618 B2 | 6/2015 | Hawkins et al. | |
| 9,044,619 B2 | 6/2015 | Hawkins et al. | |
| 9,056,185 B2 | 6/2015 | Fischell et al. | |
| 9,072,534 B2 | 7/2015 | Adams et al. | |
| 9,089,669 B2 | 7/2015 | Haslinger et al. | |
| 9,131,949 B2 | 9/2015 | Coleman et al. | |
| 9,138,249 B2 | 9/2015 | Adams et al. | |
| 9,138,260 B2 | 9/2015 | Miller et al. | |
| 9,180,280 B2 | 11/2015 | Hawkins et al. | |
| 9,220,521 B2 | 12/2015 | Hawkins et al. | |
| 9,237,984 B2 | 1/2016 | Hawkins et al. | |
| 9,254,169 B2 | 2/2016 | Long et al. | |
| 9,282,984 B2 | 3/2016 | Nita | |
| 9,283,359 B2 | 3/2016 | Pepper | |
| 9,289,132 B2 | 3/2016 | Ghaffari et al. | |
| 9,289,224 B2 | 3/2016 | Adams et al. | |
| 9,289,319 B2 | 3/2016 | Pacetti et al. | |
| 9,320,530 B2 | 4/2016 | Grace | |
| 9,333,000 B2 | 5/2016 | Hakala et al. | |
| 9,339,632 B2 | 5/2016 | Eidenschink et al. | |
| 9,364,645 B2 | 6/2016 | Erikawa | |
| 9,375,223 B2 | 6/2016 | Wallace | |
| 9,421,025 B2 | 8/2016 | Hawkins et al. | |
| 9,433,428 B2 | 9/2016 | Hakala et al. | |
| 9,433,745 B2 | 9/2016 | Cully | |
| 9,504,809 B2 | 11/2016 | Bo | |
| 9,510,887 B2 | 12/2016 | Burnett | |
| 9,522,012 B2 | 12/2016 | Adams | |
| 9,554,815 B2 | 1/2017 | Adams et al. | |
| 9,555,267 B2 | 1/2017 | Ein-gal | |
| 9,566,209 B2 | 2/2017 | Katragadda et al. | |
| 9,579,114 B2 | 2/2017 | Mantell et al. | |
| 9,579,492 B2 | 2/2017 | Simpson | |
| 9,585,684 B2 | 3/2017 | Nita et al. | |
| 9,592,328 B2 | 3/2017 | Jeevanandam | |
| 9,603,506 B2 | 3/2017 | Goldfarb et al. | |
| 9,629,567 B2 | 4/2017 | Porath et al. | |
| 9,642,673 B2 | 5/2017 | Adams | |
| 9,662,069 B2 | 5/2017 | De Graff et al. | |
| 9,687,166 B2 | 6/2017 | Subramaniam | |
| 9,700,655 B2 | 7/2017 | Laudenslager et al. | |
| 9,730,715 B2 | 8/2017 | Adams | |
| 9,737,361 B2 | 8/2017 | Magana | |
| 9,764,142 B2 | 9/2017 | Imran | |
| 9,782,570 B2 | 10/2017 | Hirszowicz | |
| 9,814,476 B2 | 11/2017 | Adams et al. | |
| 9,833,348 B2 | 12/2017 | Jordan et al. | |
| 9,839,764 B2 | 12/2017 | Chouinard | |
| 9,861,377 B2 | 1/2018 | Mantell et al. | |
| 9,867,629 B2 | 1/2018 | Hawkins et al. | |
| 9,878,135 B2 | 1/2018 | Holzapfel et al. | |
| 9,894,756 B2 | 2/2018 | Weinkam et al. | |
| 9,901,704 B2 | 2/2018 | Appling | |
| 9,955,946 B2 | 5/2018 | Miller et al. | |
| 9,974,963 B2 | 5/2018 | Imran | |
| 9,974,970 B2 | 5/2018 | Nuta et al. | |
| 9,993,292 B2 | 6/2018 | Adams et al. | |
| 10,039,561 B2 | 8/2018 | Adams et al. | |
| 10,076,384 B2 | 9/2018 | Kasprzyk | |
| 10,086,175 B2 | 10/2018 | Torres et al. | |
| 10,124,153 B2 | 11/2018 | Feig | |
| 10,136,829 B2 | 11/2018 | Deno et al. | |
| 10,149,690 B2 | 12/2018 | Hawkins et al. | |
| 10,159,505 B2 | 12/2018 | Hakala et al. | |
| 10,194,994 B2 | 2/2019 | Deno et al. | |
| 10,201,387 B2 | 2/2019 | Grace et al. | |
| 10,206,698 B2 | 2/2019 | Hakala et al. | |
| 10,226,265 B2 | 3/2019 | Ku et al. | |
| 10,245,410 B2 | 4/2019 | Aggerholm | |
| 10,327,846 B1 | 6/2019 | Stark et al. | |
| 10,328,290 B2 | 6/2019 | Zhou et al. | |
| 10,357,264 B2 | 7/2019 | Kat-Kuoy | |
| 10,405,923 B2 | 9/2019 | Yu et al. | |
| 10,406,031 B2 | 9/2019 | Thyzel | |
| 10,406,318 B2 | 9/2019 | Williams | |
| 10,420,569 B2 | 9/2019 | Adams | |
| 10,439,791 B2 | 10/2019 | Kalhan | |
| 10,441,300 B2 | 10/2019 | Hawkins | |
| 10,449,339 B2 | 10/2019 | Wilson et al. | |
| 10,463,430 B2 | 11/2019 | Dick | |
| 10,478,202 B2 | 11/2019 | Adams et al. | |
| 10,517,620 B2 | 12/2019 | Adams | |
| 10,517,621 B1 | 12/2019 | Hakala et al. | |
| 10,537,287 B2 | 1/2020 | Braido et al. | |
| 10,555,744 B2 | 2/2020 | Nguyen et al. | |
| 10,561,428 B2 | 2/2020 | Eggert et al. | |
| 10,583,277 B2 | 3/2020 | Rundquist | |
| 10,589,073 B2 | 3/2020 | Mallaby | |
| 10,617,850 B2 | 4/2020 | Tal | |
| 10,646,240 B2 | 5/2020 | Betelia et al. | |
| 10,668,245 B2 | 6/2020 | Kanae | |
| 10,682,178 B2 | 6/2020 | Adams et al. | |
| 10,695,531 B2 | 6/2020 | Suzuki | |
| 10,702,293 B2 | 7/2020 | Adams et al. | |
| 10,709,462 B2 | 7/2020 | Nguyen et al. | |
| 10,709,872 B2 | 7/2020 | Alvarez et al. | |
| 10,758,255 B2 | 9/2020 | Adams | |
| 10,797,684 B1 | 10/2020 | Benz et al. | |
| 10,799,688 B2 | 10/2020 | Calhoun | |
| 10,842,567 B2 | 11/2020 | Grace et al. | |
| 10,850,075 B2 | 12/2020 | Tarunaga | |
| 10,857,329 B2 | 12/2020 | Davies | |
| 10,933,225 B2 | 3/2021 | Campbell | |
| 10,952,740 B2 | 3/2021 | Dasnurkar et al. | |
| 10,952,790 B2 | 3/2021 | Haverkost et al. | |
| 10,959,743 B2 | 3/2021 | Adams et al. | |
| 10,966,737 B2 | 4/2021 | Nguyen | |
| 10,967,156 B2 | 4/2021 | Gulachenski | |
| 10,973,538 B2 | 4/2021 | Hakala et al. | |
| 10,974,028 B2 | 4/2021 | Buller et al. | |
| 10,980,987 B2 | 4/2021 | Tarunaga | |
| 11,000,299 B2 | 5/2021 | Hawkins et al. | |
| 11,020,135 B1 | 6/2021 | Hawkins | |
| 11,026,707 B2 | 6/2021 | Ku et al. | |
| 11,040,176 B2 | 6/2021 | Blanchard et al. | |
| 11,058,492 B2 | 7/2021 | Grace et al. | |
| 11,076,874 B2 | 8/2021 | Hakala et al. | |
| 11,116,939 B2 | 9/2021 | Jamous et al. | |
| 11,141,131 B2 | 10/2021 | Stigall | |
| 11,179,169 B2 | 11/2021 | Brouillete et al. | |
| 11,207,493 B2 | 12/2021 | Suzuki et al. | |
| 11,213,661 B2 | 1/2022 | Spindler | |
| 11,229,772 B2 | 1/2022 | Nita | |
| 11,229,776 B2 | 1/2022 | Kugler et al. | |
| 11,246,659 B2 | 2/2022 | Grace et al. | |

(56) References Cited

U.S. PATENT DOCUMENTS

| | | | |
|---|---|---|---|
| 11,253,681 B2 | 2/2022 | Williams | |
| 11,266,817 B2 | 3/2022 | Cope et al. | |
| 11,389,171 B2 | 7/2022 | Goldsmith | |
| 11,389,628 B2 | 7/2022 | Spencer | |
| 11,395,669 B2 | 7/2022 | O'Malley et al. | |
| 11,399,862 B2 | 8/2022 | Massimini et al. | |
| 11,406,452 B2 | 8/2022 | Efremkin | |
| 11,406,799 B2 | 8/2022 | McEvaddy et al. | |
| 11,484,327 B2 | 11/2022 | Anderson et al. | |
| 11,540,848 B2 | 1/2023 | Cai et al. | |
| 11,564,729 B2 | 1/2023 | Walzman | |
| 11,602,363 B2 | 3/2023 | Nguyen | |
| 11,633,200 B2 | 4/2023 | Anderson et al. | |
| 11,672,585 B2 | 6/2023 | Schultheis | |
| 11,672,599 B2 | 6/2023 | Schultheis et al. | |
| 11,707,323 B2 | 7/2023 | Schultheis et al. | |
| 11,771,449 B2 | 10/2023 | Adams et al. | |
| 11,779,363 B2 | 10/2023 | Vo | |
| 11,826,530 B2 | 11/2023 | Suzuki | |
| 11,839,391 B2 | 12/2023 | Schultheis et al. | |
| 11,911,054 B2 | 2/2024 | Singla | |
| 11,911,056 B2 | 2/2024 | Anderson et al. | |
| 11,918,285 B2 | 3/2024 | Sun et al. | |
| 11,944,331 B2 | 4/2024 | Anderson et al. | |
| 11,950,793 B2 | 4/2024 | Nguyen | |
| 12,011,185 B2 | 6/2024 | Vo | |
| 12,023,098 B2 | 7/2024 | Nguyen | |
| 12,035,932 B1 | 7/2024 | Nunes | |
| 12,076,077 B2 | 9/2024 | Mori | |
| 12,144,516 B2 | 11/2024 | Betelia | |
| 12,178,458 B1 | 12/2024 | Betelia et al. | |
| 12,193,691 B2 | 1/2025 | Adams | |
| 2001/0016761 A1 | 8/2001 | Rudie | |
| 2001/0018569 A1 | 8/2001 | Erbel | |
| 2001/0020164 A1 | 9/2001 | Papademetriou | |
| 2001/0049464 A1 | 12/2001 | Ganz | |
| 2001/0051784 A1 | 12/2001 | Brisken | |
| 2002/0045811 A1* | 4/2002 | Kittrell | G02B 6/4296 |
| | | | 606/7 |
| 2002/0052621 A1 | 5/2002 | Fried et al. | |
| 2002/0065512 A1 | 5/2002 | Fjield et al. | |
| 2002/0082553 A1 | 6/2002 | Duchamp | |
| 2002/0183620 A1 | 12/2002 | Tearney | |
| 2002/0183729 A1 | 12/2002 | Farr et al. | |
| 2002/0188204 A1 | 12/2002 | McNamara et al. | |
| 2003/0009157 A1 | 1/2003 | Levine et al. | |
| 2003/0050632 A1 | 3/2003 | Fjield et al. | |
| 2003/0065316 A1 | 4/2003 | Levine et al. | |
| 2003/0114901 A1 | 6/2003 | Loeb et al. | |
| 2003/0125719 A1 | 7/2003 | Furnish | |
| 2003/0144654 A1 | 7/2003 | Hilal | |
| 2003/0176873 A1 | 9/2003 | Chernenko et al. | |
| 2004/0002677 A1 | 1/2004 | Gentsler | |
| 2004/0024349 A1 | 2/2004 | Flock et al. | |
| 2004/0073251 A1 | 4/2004 | Weber | |
| 2004/0097996 A1 | 5/2004 | Rabiner | |
| 2004/0133254 A1 | 7/2004 | Sterzer et al. | |
| 2004/0162508 A1 | 8/2004 | Uebelacker | |
| 2004/0210278 A1 | 10/2004 | Boll | |
| 2004/0243119 A1 | 12/2004 | Lane et al. | |
| 2004/0249401 A1 | 12/2004 | Rabiner | |
| 2004/0254570 A1 | 12/2004 | Hadsjicostis | |
| 2005/0010095 A1 | 1/2005 | Stewart et al. | |
| 2005/0021013 A1 | 1/2005 | Visuri | |
| 2005/0080396 A1 | 4/2005 | Rontal | |
| 2005/0113722 A1 | 5/2005 | Schultheis | |
| 2005/0171437 A1 | 8/2005 | Carberry | |
| 2005/0171527 A1 | 8/2005 | Bhola | |
| 2005/0251131 A1 | 11/2005 | Lesh | |
| 2005/0259319 A1 | 11/2005 | Brooker | |
| 2005/0273014 A1 | 12/2005 | Gianchandani et al. | |
| 2005/0277839 A1 | 12/2005 | Alderman et al. | |
| 2006/0033241 A1 | 2/2006 | Schewe et al. | |
| 2006/0084966 A1 | 4/2006 | Maguire et al. | |
| 2006/0098921 A1 | 5/2006 | Benaron et al. | |
| 2006/0142703 A1 | 6/2006 | Carter | |
| 2006/0190022 A1 | 8/2006 | Beyar et al. | |
| 2006/0200039 A1 | 9/2006 | Brockway et al. | |
| 2006/0221528 A1 | 10/2006 | Li et al. | |
| 2006/0241524 A1 | 10/2006 | Lee et al. | |
| 2006/0241572 A1 | 10/2006 | Zhou | |
| 2006/0241733 A1 | 10/2006 | Zhang et al. | |
| 2006/0270976 A1 | 11/2006 | Savage et al. | |
| 2007/0027524 A1 | 2/2007 | Johnson | |
| 2007/0043340 A1 | 2/2007 | Thyzel | |
| 2007/0060990 A1 | 3/2007 | Satake | |
| 2007/0088380 A1 | 4/2007 | Hirszowicz et al. | |
| 2007/0118057 A1 | 5/2007 | Ein-gal | |
| 2007/0142779 A1 | 6/2007 | Duane | |
| 2007/0142819 A1 | 6/2007 | El-Nounou et al. | |
| 2007/0142821 A1 | 6/2007 | Hennessy et al. | |
| 2007/0142856 A1 | 6/2007 | Jang | |
| 2007/0179496 A1 | 8/2007 | Swoyer | |
| 2007/0239082 A1 | 10/2007 | Schultheiss et al. | |
| 2007/0255270 A1 | 11/2007 | Carney | |
| 2007/0264353 A1 | 11/2007 | Myntti et al. | |
| 2007/0270897 A1 | 11/2007 | Skerven | |
| 2007/0280311 A1 | 12/2007 | Hofmann | |
| 2007/0299392 A1 | 12/2007 | Beyar et al. | |
| 2008/0033519 A1 | 2/2008 | Burwell | |
| 2008/0081950 A1 | 4/2008 | Koenig et al. | |
| 2008/0086118 A1 | 4/2008 | Lai | |
| 2008/0095714 A1 | 4/2008 | Castella et al. | |
| 2008/0097251 A1 | 4/2008 | Babaev | |
| 2008/0108867 A1 | 5/2008 | Zhou | |
| 2008/0114341 A1 | 5/2008 | Thyzel | |
| 2008/0132810 A1 | 6/2008 | Scoseria et al. | |
| 2008/0175539 A1 | 7/2008 | Brown | |
| 2008/0195088 A1 | 8/2008 | Farr et al. | |
| 2008/0214891 A1 | 9/2008 | Slenker et al. | |
| 2008/0221550 A1 | 9/2008 | Lee | |
| 2008/0281157 A1 | 11/2008 | Miyagi et al. | |
| 2008/0296152 A1 | 12/2008 | Voss | |
| 2008/0319356 A1 | 12/2008 | Cain et al. | |
| 2009/0036803 A1 | 2/2009 | Warlick et al. | |
| 2009/0043300 A1 | 2/2009 | Reitmajer et al. | |
| 2009/0054881 A1 | 2/2009 | Krespi | |
| 2009/0097806 A1 | 4/2009 | Viellerobe et al. | |
| 2009/0125007 A1 | 5/2009 | Splinter | |
| 2009/0131921 A1 | 5/2009 | Kurtz et al. | |
| 2009/0192495 A1 | 7/2009 | Ostrovsky et al. | |
| 2009/0240242 A1* | 9/2009 | Neuberger | A61B 18/24 |
| | | | 606/7 |
| 2009/0247945 A1 | 10/2009 | Levit | |
| 2009/0281531 A1 | 11/2009 | Rizoiu | |
| 2009/0292296 A1 | 11/2009 | Pansky | |
| 2009/0296751 A1 | 12/2009 | Kewitsch et al. | |
| 2009/0299327 A1 | 12/2009 | Tilson et al. | |
| 2009/0306533 A1 | 12/2009 | Rousche | |
| 2009/0312768 A1 | 12/2009 | Hawkins et al. | |
| 2010/0016862 A1 | 1/2010 | Hawkins et al. | |
| 2010/0036238 A1 | 2/2010 | Neidert | |
| 2010/0036294 A1 | 2/2010 | Mantell et al. | |
| 2010/0063491 A1 | 3/2010 | Verhagen | |
| 2010/0094209 A1 | 4/2010 | Drasler et al. | |
| 2010/0114020 A1 | 5/2010 | Hawkins et al. | |
| 2010/0114065 A1 | 5/2010 | Hawkins et al. | |
| 2010/0125268 A1 | 5/2010 | Gustus et al. | |
| 2010/0160838 A1 | 6/2010 | Krespi | |
| 2010/0160903 A1 | 6/2010 | Krespi | |
| 2010/0168572 A1 | 7/2010 | Sliwa | |
| 2010/0168836 A1 | 7/2010 | Kassab | |
| 2010/0168862 A1 | 7/2010 | Edie et al. | |
| 2010/0179632 A1 | 7/2010 | Bruszewski et al. | |
| 2010/0191089 A1 | 7/2010 | Stebler et al. | |
| 2010/0198114 A1 | 8/2010 | Novak et al. | |
| 2010/0199773 A1 | 8/2010 | Zhou | |
| 2010/0222786 A1 | 9/2010 | Kassab | |
| 2010/0234875 A1 | 9/2010 | Allex et al. | |
| 2010/0256535 A1 | 10/2010 | Novak et al. | |
| 2010/0265733 A1 | 10/2010 | O'Leary | |
| 2010/0286791 A1 | 11/2010 | Goldsmith | |
| 2010/0316333 A1 | 12/2010 | Luther | |
| 2011/0034832 A1 | 2/2011 | Cioanta et al. | |

(56)                    References Cited

U.S. PATENT DOCUMENTS

| | | |
|---|---|---|
| 2011/0059415 A1 | 3/2011 | Kasenbacher |
| 2011/0082452 A1 | 4/2011 | Melsky |
| 2011/0082534 A1 | 4/2011 | Wallace |
| 2011/0118634 A1 | 5/2011 | Golan |
| 2011/0144502 A1 | 6/2011 | Zhou et al. |
| 2011/0184244 A1 | 7/2011 | Kagaya et al. |
| 2011/0208185 A1 | 8/2011 | Diamant et al. |
| 2011/0213349 A1 | 9/2011 | Brown |
| 2011/0245740 A1 | 10/2011 | Novak et al. |
| 2011/0257641 A1 | 10/2011 | Hastings et al. |
| 2011/0263921 A1 | 10/2011 | Vrba et al. |
| 2011/0275990 A1 | 11/2011 | Besser et al. |
| 2011/0306956 A1 | 12/2011 | Islam |
| 2012/0064141 A1 | 3/2012 | Andreacchi et al. |
| 2012/0071715 A1 | 3/2012 | Beyar et al. |
| 2012/0071867 A1 | 3/2012 | Ryan |
| 2012/0071889 A1 | 3/2012 | Mantell et al. |
| 2012/0089132 A1 | 4/2012 | Dick et al. |
| 2012/0095335 A1 | 4/2012 | Sverdlik et al. |
| 2012/0095461 A1 | 4/2012 | Herscher et al. |
| 2012/0116289 A1 | 5/2012 | Hawkins et al. |
| 2012/0116486 A1 | 5/2012 | Naga et al. |
| 2012/0123331 A1 | 5/2012 | Satake |
| 2012/0123399 A1 | 5/2012 | Belikov |
| 2012/0143131 A1 | 6/2012 | Tun |
| 2012/0157892 A1 | 6/2012 | Reitmajer et al. |
| 2012/0203255 A1 | 8/2012 | Hawkins et al. |
| 2012/0221013 A1 | 8/2012 | Hawkins et al. |
| 2012/0232409 A1 | 9/2012 | Stahmann |
| 2012/0296367 A1 | 11/2012 | Grovender et al. |
| 2012/0323211 A1 | 12/2012 | Ogle |
| 2012/0330293 A1 | 12/2012 | Arai |
| 2013/0030431 A1 | 1/2013 | Adams |
| 2013/0030447 A1 | 1/2013 | Adams |
| 2013/0041355 A1 | 2/2013 | Heeren et al. |
| 2013/0046207 A1 | 2/2013 | Capelli |
| 2013/0046293 A1 | 2/2013 | Arai et al. |
| 2013/0053762 A1 | 2/2013 | Rontal et al. |
| 2013/0060234 A1 | 3/2013 | Besser |
| 2013/0110003 A1 | 5/2013 | Surti |
| 2013/0116714 A1 | 5/2013 | Adams et al. |
| 2013/0165764 A1 | 6/2013 | Scheuermann |
| 2013/0190803 A1 | 7/2013 | Angel et al. |
| 2013/0197614 A1 | 8/2013 | Gustus |
| 2013/0218054 A1 | 8/2013 | Sverdlik et al. |
| 2013/0226131 A1 | 8/2013 | Bacino et al. |
| 2013/0253466 A1 | 9/2013 | Campbell |
| 2013/0274726 A1 | 10/2013 | Takayama |
| 2013/0345617 A1 | 12/2013 | Wallace |
| 2014/0005576 A1 | 1/2014 | Adams |
| 2014/0005706 A1 | 1/2014 | Gelfand et al. |
| 2014/0012186 A1 | 1/2014 | Thyzel |
| 2014/0039002 A1 | 2/2014 | Diodone et al. |
| 2014/0039358 A1 | 2/2014 | Zhou et al. |
| 2014/0039513 A1 | 2/2014 | Hakala |
| 2014/0046229 A1 | 2/2014 | Hawkins et al. |
| 2014/0046353 A1 | 2/2014 | Adams |
| 2014/0052146 A1 | 2/2014 | Curtis et al. |
| 2014/0052147 A1 | 2/2014 | Hakala et al. |
| 2014/0058294 A1 | 2/2014 | Gross et al. |
| 2014/0074111 A1 | 3/2014 | Hakala |
| 2014/0128848 A1 | 5/2014 | Appling et al. |
| 2014/0153087 A1 | 6/2014 | Hutchings et al. |
| 2014/0155990 A1 | 6/2014 | Nyuli |
| 2014/0180069 A1 | 6/2014 | Millett |
| 2014/0180126 A1 | 6/2014 | Millett |
| 2014/0180134 A1 | 6/2014 | Hoseit |
| 2014/0188094 A1 | 7/2014 | Islam |
| 2014/0228829 A1 | 8/2014 | Schmitt |
| 2014/0257144 A1 | 9/2014 | Capelli et al. |
| 2014/0257148 A1 | 9/2014 | Jie |
| 2014/0276573 A1 | 9/2014 | Miesel |
| 2014/0288570 A1 | 9/2014 | Adams |
| 2014/0309536 A1 | 10/2014 | Douk et al. |
| 2014/0336626 A1 | 11/2014 | Jiang |
| 2014/0336637 A1 | 11/2014 | Agrawal |
| 2014/0357997 A1 | 12/2014 | Hartmann |
| 2015/0003900 A1 | 1/2015 | Ullrich et al. |
| 2015/0005576 A1 | 1/2015 | Diodone et al. |
| 2015/0039002 A1 | 2/2015 | Hawkins |
| 2015/0057648 A1 | 2/2015 | Swift et al. |
| 2015/0071591 A1 | 3/2015 | Chen |
| 2015/0073430 A1 | 3/2015 | Hakala et al. |
| 2015/0080875 A1 | 3/2015 | Kasprzyk et al. |
| 2015/0100048 A1 | 4/2015 | Hiereth et al. |
| 2015/0105715 A1 | 4/2015 | Pikus et al. |
| 2015/0119870 A1 | 4/2015 | Rudie |
| 2015/0126990 A1 | 5/2015 | Sharma |
| 2015/0141764 A1 | 5/2015 | Harks et al. |
| 2015/0250542 A1 | 9/2015 | Islam |
| 2015/0276689 A1 | 10/2015 | Watanabe et al. |
| 2015/0313732 A1 | 11/2015 | Fulton, III |
| 2015/0320432 A1 | 11/2015 | Adams |
| 2015/0342678 A1 | 12/2015 | Deladurantaye et al. |
| 2015/0342681 A1 | 12/2015 | Lee |
| 2015/0359432 A1 | 12/2015 | Ehrenreich |
| 2015/0359557 A1 | 12/2015 | Shimokawa |
| 2016/0008016 A1 | 1/2016 | Cioanta et al. |
| 2016/0016016 A1 | 1/2016 | Taylor et al. |
| 2016/0018602 A1 | 1/2016 | Govari et al. |
| 2016/0022294 A1 | 1/2016 | Cioanta et al. |
| 2016/0038087 A1 | 2/2016 | Hunter |
| 2016/0095610 A1 | 4/2016 | Lipowski et al. |
| 2016/0135828 A1 | 5/2016 | Hawkins et al. |
| 2016/0135891 A1 | 5/2016 | Feldman |
| 2016/0143522 A1 | 5/2016 | Ransbury |
| 2016/0151639 A1 | 6/2016 | Scharf et al. |
| 2016/0183819 A1 | 6/2016 | Burnett |
| 2016/0183957 A1 | 6/2016 | Hakala et al. |
| 2016/0184020 A1 | 6/2016 | Kowalewski et al. |
| 2016/0184022 A1 | 6/2016 | Grace et al. |
| 2016/0184023 A1 | 6/2016 | Grace et al. |
| 2016/0184526 A1 | 6/2016 | Beyar |
| 2016/0184570 A1 | 6/2016 | Grace et al. |
| 2016/0228187 A1 | 8/2016 | Gross |
| 2016/0234534 A1 | 8/2016 | Kitahara et al. |
| 2016/0262784 A1 | 9/2016 | Grace et al. |
| 2016/0270806 A1 | 9/2016 | Wallace |
| 2016/0302762 A1 | 10/2016 | Stigall et al. |
| 2016/0324564 A1 | 11/2016 | Gerlach et al. |
| 2016/0331389 A1 | 11/2016 | Hakala et al. |
| 2016/0339204 A1 | 11/2016 | Williams |
| 2016/0367274 A1 | 12/2016 | Wallace |
| 2016/0367275 A1 | 12/2016 | Wallace |
| 2017/0049463 A1 | 2/2017 | Popovic et al. |
| 2017/0056035 A1 | 3/2017 | Adams |
| 2017/0086867 A1 | 3/2017 | Adams |
| 2017/0119469 A1 | 5/2017 | Shimizu et al. |
| 2017/0119470 A1 | 5/2017 | Diamant et al. |
| 2017/0135709 A1 | 5/2017 | Nguyen et al. |
| 2017/0151421 A1 | 6/2017 | Asher |
| 2017/0192242 A1 | 7/2017 | Laycock |
| 2017/0209050 A1 | 7/2017 | Fengler et al. |
| 2017/0265942 A1 | 9/2017 | Grace et al. |
| 2017/0303946 A1 | 10/2017 | Ku et al. |
| 2017/0311965 A1 | 11/2017 | Adams |
| 2018/0008348 A1 | 1/2018 | Grace et al. |
| 2018/0042661 A1 | 2/2018 | Long |
| 2018/0042677 A1 | 2/2018 | Yu et al. |
| 2018/0045897 A1 | 2/2018 | Chia |
| 2018/0049877 A1 | 2/2018 | Venkatasubramanian |
| 2018/0085174 A1 | 3/2018 | Radtke et al. |
| 2018/0092763 A1 | 4/2018 | Dagan et al. |
| 2018/0095287 A1 | 4/2018 | Jeng et al. |
| 2018/0098779 A1 | 4/2018 | Betelia et al. |
| 2018/0152568 A1 | 5/2018 | Thumpudi et al. |
| 2018/0169392 A1 | 6/2018 | Franklin |
| 2018/0214677 A1 | 8/2018 | Tarunaga |
| 2018/0238675 A1 | 8/2018 | Wan |
| 2018/0256250 A1 | 9/2018 | Adams et al. |
| 2018/0280005 A1 | 10/2018 | Parmentier |
| 2018/0303501 A1 | 10/2018 | Hawkins |
| 2018/0303503 A1 | 10/2018 | Eggert et al. |
| 2018/0303504 A1 | 10/2018 | Eggert et al. |

(56)  References Cited

U.S. PATENT DOCUMENTS

| | | |
|---|---|---|
| 2018/0304053 A1 | 10/2018 | Eggert et al. |
| 2018/0323571 A1 | 11/2018 | Brown et al. |
| 2018/0333043 A1 | 11/2018 | Teriluc |
| 2018/0360482 A1 | 12/2018 | Nguyen |
| 2019/0029702 A1 | 1/2019 | De Cicco |
| 2019/0029703 A1 | 1/2019 | Wasdyke et al. |
| 2019/0069916 A1 | 3/2019 | Hawkins et al. |
| 2019/0072378 A1 | 3/2019 | Hane et al. |
| 2019/0097380 A1 | 3/2019 | Luft et al. |
| 2019/0099588 A1 | 4/2019 | Ramanath et al. |
| 2019/0104933 A1 | 4/2019 | Stern |
| 2019/0117242 A1 | 4/2019 | Lawinger |
| 2019/0150960 A1 | 5/2019 | Nguyen et al. |
| 2019/0150961 A1 | 5/2019 | Tozzi |
| 2019/0159792 A1 | 5/2019 | Panian |
| 2019/0167349 A1 | 6/2019 | Shamay |
| 2019/0175111 A1 | 6/2019 | Genereux et al. |
| 2019/0175300 A1* | 6/2019 | Horn ................... A61B 18/24 |
| 2019/0175372 A1 | 6/2019 | Boyden et al. |
| 2019/0175407 A1 | 6/2019 | Bacher |
| 2019/0209368 A1 | 7/2019 | Park et al. |
| 2019/0232066 A1 | 8/2019 | Lim et al. |
| 2019/0247680 A1 | 8/2019 | Mayer |
| 2019/0262594 A1 | 8/2019 | Ogata et al. |
| 2019/0265419 A1 | 8/2019 | Tayebati |
| 2019/0282249 A1 | 9/2019 | Tran et al. |
| 2019/0282250 A1 | 9/2019 | Tran et al. |
| 2019/0285803 A1 | 9/2019 | Van Zuylen |
| 2019/0321100 A1 | 10/2019 | Masotti et al. |
| 2019/0321101 A1 | 10/2019 | Massoti et al. |
| 2019/0328259 A1 | 10/2019 | Deno et al. |
| 2019/0365400 A1 | 12/2019 | Adams et al. |
| 2019/0380589 A1 | 12/2019 | Lloret |
| 2019/0388002 A1 | 12/2019 | Bozsak et al. |
| 2019/0388110 A1 | 12/2019 | Nguyen et al. |
| 2019/0388133 A1 | 12/2019 | Sharma |
| 2019/0388151 A1 | 12/2019 | Bhawalkar |
| 2019/0388654 A1 | 12/2019 | Chou |
| 2020/0000484 A1 | 1/2020 | Hawkins |
| 2020/0008856 A1 | 1/2020 | Harmouche |
| 2020/0022754 A1 | 1/2020 | Cottone |
| 2020/0038087 A1 | 2/2020 | Harmouche |
| 2020/0046429 A1 | 2/2020 | Tschida et al. |
| 2020/0046949 A1 | 2/2020 | Chisena et al. |
| 2020/0054352 A1 | 2/2020 | Brouillette et al. |
| 2020/0060814 A1 | 2/2020 | Murphy |
| 2020/0061931 A1 | 2/2020 | Brown et al. |
| 2020/0069371 A1 | 3/2020 | Brown et al. |
| 2020/0085458 A1 | 3/2020 | Nguyen et al. |
| 2020/0085459 A1 | 3/2020 | Adams |
| 2020/0101269 A1 | 4/2020 | Hayes |
| 2020/0107960 A1 | 4/2020 | Bacher |
| 2020/0108236 A1 | 4/2020 | Salazar et al. |
| 2020/0129195 A1 | 4/2020 | McGowan et al. |
| 2020/0129741 A1 | 4/2020 | Kawwas |
| 2020/0155812 A1 | 5/2020 | Zhang et al. |
| 2020/0197019 A1 | 6/2020 | Harper |
| 2020/0205890 A1 | 7/2020 | Harlev |
| 2020/0246032 A1 | 8/2020 | Betelia et al. |
| 2020/0289202 A1 | 9/2020 | Miyagawa et al. |
| 2020/0297366 A1 | 9/2020 | Nguyen et al. |
| 2020/0337717 A1 | 10/2020 | Walzman |
| 2020/0345380 A1 | 11/2020 | Boyle et al. |
| 2020/0383724 A1 | 12/2020 | Adams et al. |
| 2020/0397230 A1 | 12/2020 | Massimini et al. |
| 2020/0397453 A1 | 12/2020 | McGowan et al. |
| 2020/0398033 A1 | 12/2020 | McGowan et al. |
| 2020/0405333 A1 | 12/2020 | Massimini et al. |
| 2020/0405391 A1 | 12/2020 | Massimini et al. |
| 2020/0406009 A1 | 12/2020 | Massimini et al. |
| 2020/0406010 A1 | 12/2020 | Massimini et al. |
| 2021/0038237 A1 | 2/2021 | Adams |
| 2021/0085347 A1 | 3/2021 | Phan et al. |
| 2021/0085348 A1 | 3/2021 | Nguyen |
| 2021/0085383 A1 | 3/2021 | Vo et al. |
| 2021/0116302 A1 | 4/2021 | Jean-Ruel |
| 2021/0128241 A1 | 5/2021 | Schultheis |
| 2021/0137598 A1 | 5/2021 | Cook |
| 2021/0153939 A1 | 5/2021 | Cook |
| 2021/0177442 A1 | 6/2021 | Girdhar et al. |
| 2021/0177445 A1 | 6/2021 | Nguyen |
| 2021/0186613 A1 | 6/2021 | Cook |
| 2021/0212765 A1 | 7/2021 | Verhagen |
| 2021/0220052 A1 | 7/2021 | Cook |
| 2021/0220053 A1 | 7/2021 | Cook |
| 2021/0244473 A1 | 8/2021 | Cook et al. |
| 2021/0267685 A1 | 9/2021 | Schultheis |
| 2021/0275247 A1 | 9/2021 | Schultheis |
| 2021/0275249 A1 | 9/2021 | Massimini et al. |
| 2021/0282792 A1 | 9/2021 | Adams et al. |
| 2021/0290259 A1 | 9/2021 | Hakala et al. |
| 2021/0290286 A1 | 9/2021 | Cook |
| 2021/0290305 A1 | 9/2021 | Cook |
| 2021/0298603 A1 | 9/2021 | Feldman |
| 2021/0338258 A1 | 11/2021 | Hawkins et al. |
| 2021/0353359 A1 | 11/2021 | Cook |
| 2021/0369348 A1 | 12/2021 | Cook |
| 2021/0378743 A1 | 12/2021 | Massimini et al. |
| 2021/0378744 A1 | 12/2021 | Fanier et al. |
| 2021/0386479 A1 | 12/2021 | Massimini et al. |
| 2022/0000505 A1 | 1/2022 | Hauser |
| 2022/0000506 A1 | 1/2022 | Hauser |
| 2022/0000507 A1 | 1/2022 | Hauser |
| 2022/0000508 A1 | 1/2022 | Schmitt et al. |
| 2022/0000509 A1 | 1/2022 | Laser et al. |
| 2022/0000551 A1 | 1/2022 | Govari et al. |
| 2022/0001138 A1 | 1/2022 | Howell |
| 2022/0008130 A1 | 1/2022 | Massimini et al. |
| 2022/0008693 A1 | 1/2022 | Humbert et al. |
| 2022/0015785 A1 | 1/2022 | Hakala et al. |
| 2022/0021190 A1 | 1/2022 | Pecquois |
| 2022/0022902 A1 | 1/2022 | Spano |
| 2022/0022912 A1 | 1/2022 | Efremkin |
| 2022/0023528 A1 | 1/2022 | Long et al. |
| 2022/0040454 A1 | 2/2022 | Hamm |
| 2022/0054194 A1 | 2/2022 | Bacher et al. |
| 2022/0071704 A1 | 3/2022 | Le |
| 2022/0168594 A1 | 6/2022 | Mayer |
| 2022/0183738 A1 | 6/2022 | Flores et al. |
| 2022/0218402 A1 | 7/2022 | Schultheis |
| 2022/0249165 A1 | 8/2022 | Cook |
| 2022/0249166 A1 | 8/2022 | Cook et al. |
| 2022/0273324 A1 | 9/2022 | Schultheis |
| 2022/0287732 A1 | 9/2022 | Anderson et al. |
| 2022/0313293 A1 | 10/2022 | Singh |
| 2022/0313359 A1 | 10/2022 | Schultheis et al. |
| 2022/0338890 A1 | 10/2022 | Anderson et al. |
| 2022/0354578 A1 | 11/2022 | Cook |
| 2022/0387106 A1 | 12/2022 | Cook |
| 2023/0013920 A1 | 1/2023 | Massimini |
| 2023/0064371 A1 | 3/2023 | Cook et al. |
| 2023/0137107 A1 | 5/2023 | Cook et al. |
| 2023/0157754 A1 | 5/2023 | Bacher et al. |
| 2023/0200906 A1 | 6/2023 | Cook et al. |
| 2023/0233256 A1 | 7/2023 | Cook et al. |
| 2023/0240748 A1 | 8/2023 | Cook et al. |
| 2023/0248376 A1 | 8/2023 | Anderson et al. |
| 2023/0255635 A1 | 8/2023 | Schultheis et al. |
| 2023/0255688 A1 | 8/2023 | Schultheis et al. |
| 2023/0255689 A1 | 8/2023 | Schultheis et al. |
| 2023/0310054 A1 | 10/2023 | Schultheis |
| 2023/0310067 A1 | 10/2023 | Schultheis et al. |
| 2023/0310073 A1 | 10/2023 | Adams et al. |
| 2023/0320576 A1 | 10/2023 | Feldman |
| 2023/0338088 A1 | 10/2023 | Massimini et al. |
| 2023/0338089 A1 | 10/2023 | Schultheis |
| 2023/0414234 A1 | 12/2023 | Anderson et al. |
| 2024/0001076 A1 | 1/2024 | Gelsinger |
| 2024/0016508 A1 | 1/2024 | Kocur |
| 2024/0016544 A1 | 1/2024 | Schultheis et al. |
| 2024/0016545 A1 | 1/2024 | Schultheis et al. |
| 2024/0023813 A1 | 1/2024 | Milner |
| 2024/0032995 A1 | 2/2024 | Schultheis et al. |
| 2024/0033002 A1 | 2/2024 | Cook |

(56)  References Cited

U.S. PATENT DOCUMENTS

| | | |
|---|---|---|
| 2024/0041520 A1 | 2/2024 | Schultheis et al. |
| 2024/0050170 A1 | 2/2024 | Fournier |
| 2024/0050696 A1 | 2/2024 | Japuntich |
| 2024/0058060 A1 | 2/2024 | Cook |
| 2024/0065711 A1 | 2/2024 | Hendrickson |
| 2024/0065712 A1 | 2/2024 | Schultheis |
| 2024/0099773 A1 | 3/2024 | Schabert |
| 2024/0122648 A1 | 4/2024 | Cook |
| 2024/0165658 A1 | 5/2024 | Fu |
| 2024/0173044 A1 | 5/2024 | Chen et al. |
| 2024/0173526 A1 | 5/2024 | Kofidis |
| 2024/0189543 A1 | 6/2024 | Salinas |
| 2024/0216062 A1 | 7/2024 | Cook |
| 2024/0260981 A1 | 8/2024 | Betelia |
| 2024/0260982 A1 | 8/2024 | Peterson |
| 2024/0277410 A1 | 8/2024 | Cook |
| 2024/0277974 A1 | 8/2024 | Oehler |
| 2024/0277980 A1 | 8/2024 | O'Neill |
| 2024/0285296 A1 | 8/2024 | Vo |
| 2024/0285922 A1 | 8/2024 | Chu |
| 2024/0299051 A1 | 9/2024 | Sidhu et al. |
| 2024/0307119 A1 | 9/2024 | Nguyen |
| 2024/0325045 A1 | 10/2024 | Otake |
| 2024/0382258 A1 | 11/2024 | Schultheis |
| 2025/0025237 A1 | 1/2025 | Cook |
| 2025/0040947 A1 | 2/2025 | Schultheis |

FOREIGN PATENT DOCUMENTS

| | | |
|---|---|---|
| CA | 2229806 | 3/1997 |
| CA | 2281519 | 8/1998 |
| CA | 2983655 | 10/2016 |
| CA | 3209797 | 9/2022 |
| CN | 102057422 | 5/2011 |
| CN | 109223100 | 1/2019 |
| CN | 110638501 | 1/2020 |
| CN | 110638501 A | 1/2020 |
| CN | 106794043 | 3/2020 |
| CN | 107411805 | 1/2022 |
| CN | 107899126 | 1/2022 |
| CN | 109475378 | 1/2022 |
| CN | 113876388 | 1/2022 |
| CN | 113877044 | 1/2022 |
| CN | 113907838 | 1/2022 |
| CN | 113951972 A | 1/2022 |
| CN | 113951973 A | 1/2022 |
| CN | 113974765 | 1/2022 |
| CN | 113974826 A | 1/2022 |
| CN | 113993463 | 1/2022 |
| CN | 215384399 | 1/2022 |
| CN | 215386905 | 1/2022 |
| CN | 215458400 | 1/2022 |
| CN | 215458401 | 1/2022 |
| CN | 215505065 | 1/2022 |
| CN | 215534803 | 1/2022 |
| CN | 215537694 | 1/2022 |
| CN | 215584286 | 1/2022 |
| CN | 215606068 | 1/2022 |
| CN | 215651393 | 1/2022 |
| CN | 215651394 | 1/2022 |
| CN | 215651484 | 1/2022 |
| CN | 215653328 | 1/2022 |
| CN | 114053552 | 2/2022 |
| CN | 115175625 | 10/2022 |
| CN | 117752412 | 3/2024 |
| CN | 118055734 | 5/2024 |
| DE | 3038445 A1 | 5/1982 |
| DE | 3836337 A1 | 4/1990 |
| DE | 3913027 A1 | 10/1990 |
| DE | 69431758 | 1/2003 |
| DE | 10230626 | 1/2004 |
| DE | 202008016760 | 3/2009 |
| DE | 102007046902 | 4/2009 |
| DE | 102008034702 | 1/2010 |
| DE | 102009007129 | 8/2010 |
| DE | 202010009899 | 11/2010 |
| DE | 102013201928 | 8/2014 |
| DE | 102020117713 | 1/2022 |
| EP | 0119296 | 9/1984 |
| EP | 0261831 B1 | 6/1992 |
| EP | 558297 A2 | 9/1993 |
| EP | 0571306 A1 | 11/1993 |
| EP | 0547146 | 7/1995 |
| EP | 1179993 A1 | 2/2002 |
| EP | 1946712 | 7/2008 |
| EP | 1946712 A1 | 7/2008 |
| EP | 1453566 | 9/2008 |
| EP | 2157569 | 2/2010 |
| EP | 2470248 | 7/2012 |
| EP | 2879595 | 6/2015 |
| EP | 2879595 A1 | 6/2015 |
| EP | 2944264 A1 | 6/2015 |
| EP | 3226795 A1 | 10/2017 |
| EP | 3266487 | 1/2018 |
| EP | 3318204 | 5/2018 |
| EP | 2879607 | 2/2019 |
| EP | 3461438 A1 | 4/2019 |
| EP | 3473195 A1 | 4/2019 |
| EP | 2961463 | 5/2019 |
| EP | 3240603 | 5/2019 |
| EP | 3197381 | 3/2020 |
| EP | 3643260 A1 | 4/2020 |
| EP | 3240494 | 3/2021 |
| EP | 3522812 | 12/2021 |
| EP | 3076881 B1 | 1/2022 |
| EP | 3932342 | 1/2022 |
| EP | 3936140 | 1/2022 |
| EP | 3960099 | 3/2022 |
| EP | 4051154 | 9/2022 |
| EP | 4129213 | 2/2023 |
| EP | 4277537 | 11/2023 |
| EP | 4297669 | 1/2024 |
| EP | 4146322 | 4/2024 |
| EP | 3182931 | 6/2024 |
| EP | 3950036 | 8/2024 |
| EP | 4034005 | 12/2024 |
| GB | 1082397 | 9/1967 |
| JP | S62275446 A | 11/1987 |
| JP | H05264763 | 10/1993 |
| JP | 1996089511 | 4/1996 |
| JP | H09117407 | 5/1997 |
| JP | 2001520070 | 10/2001 |
| JP | 2004519296 | 7/2004 |
| JP | 2008506447 | 3/2008 |
| JP | 2008083273 | 4/2008 |
| JP | 2009519777 | 5/2009 |
| JP | 2009213589 | 9/2009 |
| JP | 2011524203 | 9/2011 |
| JP | 4805208 | 11/2011 |
| JP | 4808620 | 11/2011 |
| JP | 2012505050 | 3/2012 |
| JP | 2014123147 | 7/2014 |
| JP | A2014516614 | 7/2014 |
| JP | A2015522344 | 8/2015 |
| JP | 2015217215 | 12/2015 |
| JP | 2018538077 | 12/2018 |
| JP | 2024511710 | 3/2024 |
| KR | 20050098932 | 10/2005 |
| KR | 20080040111 | 5/2008 |
| KR | 20160090877 A | 8/2016 |
| KR | 20180054041 | 5/2018 |
| WO | WO9007904 A1 | 7/1990 |
| WO | WO9105332 A1 | 4/1991 |
| WO | 9203095 A1 | 3/1992 |
| WO | WO9208515 | 5/1992 |
| WO | WO9524867 | 9/1995 |
| WO | 1999002095 A1 | 1/1999 |
| WO | 1999020189 A1 | 4/1999 |
| WO | WO200067648 | 11/2000 |
| WO | WO2000067648 A1 | 11/2000 |
| WO | WO0103599 | 1/2001 |
| WO | WO0103599 A2 | 1/2001 |
| WO | 20060006169 A2 | 1/2006 |
| WO | WO2006006169 | 1/2006 |

(56)                    References Cited

FOREIGN PATENT DOCUMENTS

| WO | WO2009121017 | | 10/2009 |
|---|---|---|---|
| WO | WO2009149321 | A1 | 12/2009 |
| WO | WO2009152352 | | 12/2009 |
| WO | 2010042653 | A1 | 4/2010 |
| WO | WO2011094379 | | 8/2011 |
| WO | 20110126580 | A2 | 10/2011 |
| WO | WO2011126580 | | 10/2011 |
| WO | WO2012025833 | | 3/2012 |
| WO | WO2012042619 | | 4/2012 |
| WO | WO20120052924 | A1 | 4/2012 |
| WO | WO2012058156 | | 5/2012 |
| WO | WO20120120495 | A2 | 9/2012 |
| WO | WO2013119662 | | 8/2013 |
| WO | 20130169807 | A1 | 11/2013 |
| WO | WO2013169807 | | 11/2013 |
| WO | WO2014025397 | A1 | 2/2014 |
| WO | WO20140022867 | A1 | 2/2014 |
| WO | WO2014138582 | | 9/2014 |
| WO | WO2015056662 | | 4/2015 |
| WO | WO2015097251 | A2 | 7/2015 |
| WO | 20150177790 | A1 | 11/2015 |
| WO | WO2016014999 | | 1/2016 |
| WO | WO2016089683 | A1 | 6/2016 |
| WO | WO2016090175 | | 6/2016 |
| WO | WO2016098670 | | 6/2016 |
| WO | WO2016109739 | | 7/2016 |
| WO | WO2016143556 | | 9/2016 |
| WO | WO2016151595 | A1 | 9/2016 |
| WO | WO20170192869 | A1 | 11/2017 |
| WO | 20180022641 | A1 | 2/2018 |
| WO | WO2018022593 | A1 | 2/2018 |
| WO | WO2018083666 | | 5/2018 |
| WO | 20180175322 | A1 | 9/2018 |
| WO | WO2018175322 | | 9/2018 |
| WO | WO2018191013 | | 10/2018 |
| WO | WO2019200201 | A1 | 10/2019 |
| WO | WO2019222843 | | 11/2019 |
| WO | WO2020056031 | | 3/2020 |
| WO | WO20200086361 | A1 | 4/2020 |
| WO | WO2020089876 | A1 | 5/2020 |
| WO | WO2020157648 | | 8/2020 |
| WO | WO2020256693 | | 12/2020 |
| WO | WO2020256898 | | 12/2020 |
| WO | WO2020256898 | A1 | 12/2020 |
| WO | WO2020256949 | | 12/2020 |
| WO | WO2020256949 | A1 | 12/2020 |
| WO | WO2020263469 | A1 | 12/2020 |
| WO | WO2020263685 | A1 | 12/2020 |
| WO | WO2020263687 | A1 | 12/2020 |
| WO | WO2020263688 | A1 | 12/2020 |
| WO | WO2020263689 | A1 | 12/2020 |
| WO | WO2021061451 | | 4/2021 |
| WO | WO2021067563 | | 4/2021 |
| WO | WO2021086571 | A1 | 5/2021 |
| WO | WO2021096922 | A1 | 5/2021 |
| WO | WO2021101766 | | 5/2021 |
| WO | WO2021101766 | A1 | 5/2021 |
| WO | WO2021126762 | A1 | 6/2021 |
| WO | WO2021150502 | A1 | 7/2021 |
| WO | WO2021162855 | A1 | 8/2021 |
| WO | WO2021173417 | A1 | 9/2021 |
| WO | WO2021183367 | A1 | 9/2021 |
| WO | WO2021183401 | A1 | 9/2021 |
| WO | WO2021188233 | A1 | 9/2021 |
| WO | WO2021231178 | A1 | 11/2021 |
| WO | WO2021247685 | A1 | 12/2021 |
| WO | WO2021257425 | A1 | 12/2021 |
| WO | WO2022007490 | | 1/2022 |
| WO | WO2022008440 | | 1/2022 |
| WO | WO2022010767 | A1 | 1/2022 |
| WO | WO2022055784 | | 3/2022 |
| WO | WO2022125525 | | 6/2022 |
| WO | WO2022154954 | | 7/2022 |
| WO | WO2022173719 | | 8/2022 |
| WO | WO2022183075 | | 9/2022 |
| WO | WO2022187058 | | 9/2022 |
| WO | WO2022216488 | | 10/2022 |
| WO | WO2022240674 | | 11/2022 |
| WO | WO2022260932 | | 12/2022 |
| WO | WO2023107334 | | 6/2023 |
| WO | WO2024079108 | | 4/2024 |
| WO | WO2024107418 | | 5/2024 |

OTHER PUBLICATIONS

Vogel, A., et al. "Acoustic transient generation by laser-produced cavitation bubbles near solid boundaries", Journal Acoustical Society of America, 1988, pp. 719-731, vol. 84.
Asshauer, T., et al. "Acoustic transient generation by holmium-laser-induced cavitation bubbles", Journal of Applied Physics, Nov. 1, 1994, pp. 5007-5013, vol. 76, No. 9, American Institute of Physics.
Zheng, W., "Optic Lenses Manufactured on Fiber Ends", 2015, Splicer Engineering AFL, Duncan, SC USA.
Ali, Ziad A., et al. "Optical Coherence Tomography Characterization of Coronary Lithoplasty for Treatment of Calcified Lesions", JACC: Cardiovascular Imaging, 2017, pp. 897-906, vol. 109, No. 8, Elsevier.
Ali, Ziad A., et al. "Intravascular lithotripsy for treatment of stent underexpansion secondary to severe coronary calcification" 2018, European Society of Cardiology.
Ashok, Praveen C., et al. "Raman spectroscopy bio-sensor for tissue discrimination in surgical robotics—full article", Journal of Biophotonics, 2014, pp. 103-109, vol. 7, No. 1-2.
Ashok, Praveen C., et al. "Raman spectroscopy bio-sensor for tissue discrimination in surgical robotics—proof" Journal of Biophotonics 7, 2014, No. 1-2.
Bian, D. C., et al. "Experimental Study of Pulsed Discharge Underwater Shock-Related Properties in Pressurized Liquid Water", Hindawi Advances in Materials Science and Engineering, Jan. 2018, 12 pages, vol. 2018, Article ID 8025708.
Bian, D. C., et al. "Study on Breakdown Delay Characteristics Based on High-voltage Pulse Discharge in Water with Hydrostatic Pressure", Journal of Power Technologies 97(2), 2017, pp. 89-102.
Doukas, A. G., et al. "Biological effects of laser induced shock waves: Structural and functional cell damage in vitro", Ultrasound in Medicine and Biology, 1993, pp. 137-146, vol. 19, Issue 2, Pergamon Press, USA.
Brodmann, Marianne et al. "Safety and Performance of Lithoplasty for Treatment of Calcified Peripheral Artery Lesions", JACC, 2017, vol. 70, No. 7.
Brouillette, M., "Shock Waves at Microscales", 2003, pp. 3-12, Springer-Verlag.
Mirshekari, G., et al. "Shock Waves in Microchannels", 2013, pp. 259-283, vol. 724, Cambridge University Press.
"Bubble Dynamics and Shock Waves", Springer, 2013, Springer-Verlag, Berlin Heildelberg.
Hardy, Luke A., et al. "Cavitation Bubble Dynamics During Thulium Fiber Laser Lithotripsy", SPIE, Feb. 29, 2016, vol. 9689, San Francisco, California, USA.
Claverie, A., et al. "Experimental characterization of plasma formation and shockwave propagation induced by high power pulsed underwater electrical discharge", Review of Scientific Instruments, 2014, American Institute of Physics.
Blackmon, Richard L., et al. "Comparison of holmium: YAG and thulium fiber laser lithotripsy ablation thresholds, ablation rates, and retropulsion effects", Journal of Biomedical Optics, 2011, vol. 16(7), SPIE.
Debasis, P., et al. "Continuous-wave and quasi-continuous wave thulium-doped all-fiber laser: implementation on kidney stone fragmentations", Applied Optics, Aug. 10, 2016, vol. 55, No. 23, Optical Society of America.
Cook, Jason R., et al. "Tissue mimicking phantoms for photoacoustic and ultrasonic imaging", Biomedical Optics Express, 2011, vol. 2, No. 11, Optical Society of America.
Deckelbaum, Lawrence I., "Coronary Laser Angioplasty", Lasers in Surgery and Medicine, 1994, pp. 101-110, Wiley-Liss Inc.

(56)　　　　　References Cited

OTHER PUBLICATIONS

Costanzo, F., "Underwater Explosion Phenomena and Shock Physics", Research Gate, 2011.

Mizeret, J. C., et al. "Cylindrical fiber optic light diffuser for medical applications", Lasers in Surgery and Medicine, 1996, pp. 159-167, vol. 19, Issue 2, Wiley-Liss Inc., Lausanne, Switzerland.

De Silva, K., et al. "A Calcific, Undilatable Stenosis Lithoplasty, a New Tool in the Box?", JACC: Cardiovascular Interventions, 2017, vol. 10, No. 3, Elsevier.

Vesselov, L., et al. "Design and performance of thin cylindrical diffusers created in Ge-doped multimode optical fibers", Applied Optics, 2005, pp. 2754-2758, vol. 44, Issue 14, Optical Society of America.

Hutchens, Thomas C., et al. "Detachable fiber optic tips for use in thulium fiber laser lithotripsy", Journal of Biomedical Optics, Mar. 2013, vol. 18(3), SPIE.

Kostanski, Kris L., et al. "Development of Novel Tunable Light Scattering Coating Materials for Fiber Optic Diffusers in Photodynamic Cancer Therapy", Journal of Applied Polymer Science, 2009, pp. 1516-1523, vol. 112, Wiley InterScience.

Kristiansen, M., et al. "High Voltage Water Breakdown Studies", DoD, 1998, Alexandria, VA, USA.

Dwyer, J. R., et al. "A study of X-ray emission from laboratory sparks in air at atmospheric pressure", Journal of Geophysical Research, 2008, vol. 113, American Geophysical Union.

Jansen, Duco E., et al. "Effect of Pulse Duration on Bubble Formation and Laser-Induced Pressure Waves During Holmium Laser Ablation", Lasers in Surgery and Medicine 18, 1996, pp. 278-293, Wiley-Liss Inc., Austin, TX, USA.

Shangguan, HanQun et al. "Effects of Material Properties on Laser-induced Bubble Formation in Absorbing Liquids and On Submerged Targets", SPIE, 1997, pp. 783-791, vol. 2869.

Varghese, B., et al. "Effects of polarization and absorption on laser induced optical breakdown threshold for skin rejuvenation", SPIE, Mar. 9, 2016, vol. 9740, SPIE, San Francisco, USA.

Varghese, B., et al. "Effects of polarization and apodization on laser induced optical breakdown threshold", Optics Express, Jul. 29, 2013, vol. 21, No. 15, Optical Society of America.

Bonito, Valentina, "Effects of polarization, plasma and thermal initiation pathway on irradiance threshold of laser induced optical breakdown", Philips Research, 2013, The Netherlands.

Vogel, A. et al. "Energy balance of optical breakdown in water at nanosecond to femtosecond time scales", Applied Physics B 68, 1999, pp. 271-280, Springer-Verlag.

Kang, Hyun W., et al. "Enhanced photocoagulation with catheter based diffusing optical device", Journal of Biomedical Optics, Nov. 2012, vol. 17(11), SPIE.

Esch, E., et al. "A Simple Method For Fabricating Artificial Kidney Stones Of Different Physical Properties", National Institute of Health Public Access Author Manuscript, Aug. 2010.

Isner, Jeffrey M., et al. "Excimer Laser Atherectomy", Circulation, Jun. 1990, vol. 81, No. 6, American Heart Association, Dallas, TX, USA.

Israel, Douglas H., et al. "Excimer Laser-Facilitated Balloon Angioplasty of a Nondilateable Lesion", JACC, Oct. 1991, vol. 18, No. 4, American College of Cardiology, New York, USA.

Van Leeuwen, Ton G., et al. "Excimer Laser Induced Bubble: Dimensions, Theory, and Implications for Laser Angioplasty", Lasers in Surgery and Medicine 18, 1996, pp. 381-390, Wiley-Liss Inc., Utrecht, The Netherlands.

Nguyen, H., et al. "Fabrication of multipoint side-firing optical fiber by laser micro-ablation", Optics Letters, May 1, 2017, vol. 42, No. 9, Optical Society of America.

Zheng, W., "Optic Lenses Manufactured on Fiber Ends", 2015, IEEE, Duncan, SC, USA.

Whitesides, George M., et al. "Fluidic Optics", 2006, vol. 6329, SPIE, Cambridge, MA, USA.

Forero, M., et al. "Coronary lithoplasty: a novel treatment for stent underexpansion", Cardiovascular Flashlight, 2018, European Society of Cardiology.

Ghanate, A. D., et al. "Comparative evaluation of spectroscopic models using different multivariate statistical tools in a multicancer scenario", Journal of Biomedical Optics, Feb. 2011, pp. 1-9, vol. 16(2), SPIE.

Roberts, Randy M., et al. "The Energy Partition of Underwater Sparks", The Journal of the Acoustical Society of America, Jun. 1996, pp. 3465-3474, Acoustical Society of America, Austin, TX, USA.

Blackmon, Richard L., et al. "Holmium: YAG Versus Thulium Fiber Laser Lithotripsy", Lasers in Surgery and Medicine, 2010, pp. 232-236, Wiley-Liss Inc.

Varghese, B., "Influence of absorption induced thermal initiation pathway on irradiance threshold for laser induced breakdown", Biomedical Optics Express, 2015, vol. 6, No. 4, Optical Society of America.

Noack, J., "Influence of pulse duration on mechanical effects after laser-induced breakdown in water", Journal of Applied Physics, 1998, pp. 7488-EOA, vol. 83, American Institute of Physics.

Van Leeuwen, Ton G., et al. "Intraluminal Vapor Bubble Induced by Excimer Laser Pulse Causes Microsecond Arterial Dilation and Invagination Leading to Extensive Wall Damage in the Rabbit", Circulation, Apr. 1993, vol. 87, No. 4, American Heart Association, Dallas, TX, USA.

Vogel, A., et al. "Intraocular Photodisruption With Picosecond and Nanosecond Laser Pulses: Tissue Effects in Cornea, Lens, and Retina", Investigative Ophthalmology & Visual Science, Jun. 1994, pp. 3032-3044, vol. 35, No. 7, Association for Research in Vision and Ophthalmology.

Jones, H. M., et al. "Pulsed dielectric breakdown of pressurized water and salt solutions", Journal of Applied Physics, Jun. 1998, pp. 795-805, vol. 77, No. 2, American Institute of Physics.

Kozulin, I., et al. "The dynamic of the water explosive vaporization on the flat microheater", Journal of Physics: Conference Series, 2018, pp. 1-4, IOP Publishing, Russia.

Cross, F., "Laser Angioplasty", Vascular Medicine Review, 1992, pp. 21-30, Edward Arnold.

Doukas, A. G., et al. "Laser-generated stress waves and their effects on the cell membrane", IEEE Journal of Selected Topics in Quantum Electronics, 1999, pp. 997-1003, vol. 5, Issue 4, IEEE.

Noack, J., et al. "Laser-Induced Plasma Formation in Water at Nanosecond to Femtosecond Time Scales: Calculation of Thresholds, Absorption Coefficients, and Energy Density", IEEE Journal of Quantum Electronics, 1999, pp. 1156-1167, vol. 35, No. 8, IEEE.

Pratsos, A., "The use of Laser for the treatment of coronary artery disease", Bryn Mawr Hospital, 2010.

Li, Xian-Dong, et al. "Influence of deposited energy on shock wave induced by underwater pulsed current discharge", Physics of Plasmas, 2016, vol. 23, American Institute of Physics.

Logunov, S., et al. "Light diffusing optical fiber illumination", Renewable Energy and the Environment Congress, 2013, Corning, NY, USA.

Maxwell, A. D., et al. "Cavitation clouds created by shock scattering from bubbles during histotripsy", Acoustical Society of America, 2011, pp. 1888-1898, vol. 130, No. 4, Acoustical Society of America.

Mcateer, James A., et al. "Ultracal-30 Gypsum Artificial Stones For Research On The Mechinisms Of Stone Breakage In Shock Wave Lithotripsy", 2005, pp. 429-434, Springer-Verlag.

Vogel, A., et al. "Mechanisms of Intraocular Photodisruption With Picosecond and Nanosecond Laser Pulses", Lasers in Surgery and Medicine, 1994, pp. 32-43, vol. 15, Wiley-Liss Inc., Lubeck, Germany.

Vogel, A., et al. "Mechanisms of Pulsed Laser Ablation of Biological Tissues", Chemical Reviews, 2003, pp. 577-644, vol. 103, No. 2, American Chemical Society.

Medlight, "Cylindrical light diffuser Model RD-ML", Medlight S.A., Switzerland. 2015.

Medlight, "Cylindircal light diffuser Model RD", Medlight S.A., Switzerland. 2015.

Mayo, Michael E., "Interaction of Laser Radiation with Urinary Calculi", Cranfield University Defense and Security, PhD Thesis, 2009, Cranfield University.

(56) References Cited

OTHER PUBLICATIONS

Vogel, A., et al. "Minimization of Cavitation Effects in Pulsed Laser Ablation Illustrated on Laser Angioplasty", Applied Physics, 1996, pp. 173-182, vol. 62, Springer-Verlag.

Mirshekari, G., et al. "Microscale Shock Tube", Journal of Microelectromechanical Systems, 2012, pp. 739-747, vol. 21, No. 3, IEEE.

"Polymicro Sculpted Silica Fiber Tips", Molex, 2013, Molex.

Zhou, J., et al. "Optical Fiber Tips and Their Applications", Polymicro Technologies A Subsidiary of Molex, Nov. 2007.

Liang, Xiao-Xuan, et al. "Multi-Rate-Equation modeling of the energy spectrum of laser-induced conduction band electrons in water", Optics Express, 2019, vol. 27, No. 4, Optical Society of America.

Nachabe, R., et al. "Diagnosis of breast cancer using diffuse optical spectroscopy from 500 to 1600 nm: comparison of classification methods", Journal of Biomedical Optics, 2011, vol. 16(8), SPIE.

Naugol'nykh, K. A., et al. "Spark Discharges in Water", Academy of Sciences USSR Institute of Acoustics, 1971, Nauka Publishing Co., Moscow, USSR.

Van Leeuwen, Ton G., et al. "Noncontact Tissue Ablation by Holmium: YSGG Laser Pulses in Blood", Lasers in Surgery and Medicine, 1991, vol. 11, pp. 26-34, Wiley-Liss Inc.

Nyame, Yaw A., et al. "Kidney Stone Models for In Vitro Litho-tripsy Research: A Comprehensive Review", Journal of Endourol-ogy, Oct. 2015, pp. 1106-1109, vol. 29, No. 10, Mary Ann Liebert Inc., Cleveland, USA.

Ohl, Siew-Wan, et al. "Bubbles with shock waves and ultrasound: a review", Interface Focus, pp. 1-15, vol. 5, The Royal Society Publishing. Oct. 2015.

Zheng, W., "Optical Lenses Manufactured on Fiber Ends", IEEE, 2015, Splicer Engineering, Duncan SC USA.

Dwyer, p. J., et al. "Optically integrating balloon device for photodynamic therapy", Lasers in Surgery and Medicine, 2000, pp. 58-66, vol. 26, Issue 1, Wiley-Liss Inc., Boston MA USA.

"The New Optiguide DCYL700 Fiber Optic Diffuser Series", Optiguide Fiber Optic Spec Sheet, Pinnacle Biologics, 2014, Pinnacle Biologics, Illinois, USA.

Van Leeuwen, Ton G., et al. "Origin of arterial wall dissections induced by pulsed excimer and mid-infared laser ablation in the pig", JACC, 1992, pp. 1610-1618, vol. 19, No. 7, American College of Cardiology.

Oshita, D., et al. "Characteristic of Cavitation Bubbles and Shock Waves Generated by Pulsed Electric Discharges with Different Voltages", IEEE, 2012, pp. 102-105, Kumamoto, Japan.

Karsch, Karl R., et al. "Percutaneous Coronary Excimer Laser Angioplasty in Patients With Stable and Unstable Angina Pectoris", Circulation, 1990, pp. 1849-1859, vol. 81, No. 6, American Heart Association, Dallas TX, USA.

Murray, A., et al. "Peripheral laser angioplasty with pulsed dye laser and ball tipped optical fibres", The Lancet, 1989, pp. 1471-1474, vol. 2, Issue 8678-8679.

Mohammadzadeh, M., et al. "Photoacoustic Shock Wave Emission and Cavitation from Structured Optical Fiber Tips", Applied Phys-ics Letters, 2016, vol. 108, American Institute of Physics Publishing LLC.

Doukas, A. G., et al. "Physical characteristics and biological effects of laser-induced stress waves", Ultrasound in Medicine and Biol-ogy, 1996, pp. 151-164, vol. 22, Issue 2, World Federation for Ultrasound in Medicine and Biology, USA.

Doukas, A. G., et al. "Physical factors involved in stress-wave-induced cell injury: the effect of stress gradient", Ultrasound in Medicine and Biology, 1995, pp. 961-967, vol. 21, Issue 7, Elsevier Science Ltd., USA.

Piedrahita, Francisco S., "Experimental Research Work On A Sub-Millimeter Spark-Gap For Sub Nanosecond Gas Breakdown", Thesis for Universidad Nacional De Colombia, 2012, Bogota, Colombia.

Vogel, A., et al. "Plasma Formation in Water by Picosecond and Nanosecond Nd: YAG Laser Pulses—Part I: Optical Breakdown at Threshold and Superthreshold Irradiance", IEEE Journal of Selected Topics in Quantum Electronics, 1996, pp. 847-859, vol. 2, No. 4, IEEE.

Park, Hee K., et al. "Pressure Generation and Measurement in the Rapid Vaporization of Water on a Pulsed-Laser-Heated Surface", Journal of Applied Physics, 1996, pp. 4072-4081, vol. 80, No. 7, American Institute of Physics.

Cummings, Joseph P., et al. "Q-Switched laser ablation of tissue: plume dynamics and the effect of tissue mechanical properties", SPIE, Laser-Tissue Interaction III, 1992, pp. 242-253, vol. 1646.

Lee, Seung H., et al. "Radial-firing optical fiber tip containing conical-shaped air-pocket for biomedical applications", Optics Express, 2015, vol. 23, No. 16, Optical Society of America.

Hui, C., et al. "Research on sound fields generated by laser-induced liquid breakdown", Optica Applicata, 2010, pp. 898-907, vol. XL, No. 4, Xi'an, China.

Riel, Louis-Philippe, et al. "Characterization of Calcified Plaques Retrieved From Occluded Arteries and Comparison with Potential Artificial Analogues", Proceedings of the ASME 2014 International Mechanical Engineering Congress and Exposition, 2014, pp. 1-11, ASME, Canada.

Roberts, Randy M., et al. "The Energy Partition of Underwater Sparks", The Journal of the Acoustical Society of America, 1996, pp. 3465-3475, vol. 99, No. 6, Acoustical Society of America.

Rocha, R., et al. "Fluorescence and Reflectance Spectroscopy for Identification of Atherosclerosis in Human Carotid Arteries Using Principal Components Analysis", Photomedicine and Lsser Surgery, 2008, pp. 329-335, vol. 26, No. 4, Mary Ann Liebert Inc.

Scepanovic, Obrad R., et al. "Multimodal spectroscopy detects features of vulnerable atherosclerotic plaque", Journal of Biomedi-cal Optics, 2011, pp. 1-10, vol. 16, No. 1, SPIE.

Serruys, P. W., et al. "Shaking and Breaking Calcified Plaque Lithoplasty, a Breakthrough in Interventional Armamentarium?", JACC: Cardiovascular Imaging, 2017, pp. 907-911, vol. 10, No. 8, Elsevier.

Vogel, A., et al. "Shock wave emission and cavitation bubble generation by picosecond and nanosecond optical breakdown in water", The Journal of the Acoustical Society of America, 1996, pp. 148-165, vol. 100, No. 1, Acoustical Society of America.

Vogel, A., et al. "Shock-Wave Energy and Acoustic Energy Dissi-pation After Laser-induced Breakdown", SPIE, 1998, pp. 180-189, vol. 3254, SPIE.

International Search Report and Written Opinion, issued by the EP/ISA, in PCT/US2021/048819, dated Jan. 14, 2022.

Stelzle, F., et al. "Diffuse Reflectance Spectroscopy for Optical Soft Tissue Differentiation as Remote Feedback Control for Tissue-Specific Laser Surgery", Lasers in Surgery and Medicine, 2010, pp. 319-325, vol. 42, Wiley-Liss Inc.

Stelzle, F., et al. Tissue Discrimination by Uncorrected Autofluorescence Spectra: A Proof-of-Principle Study for Tissue-Specific Laser Sur-gery, Sensors, 2013, pp. 13717-13731, vol. 13, Basel, Switzerland.

Tagawa, Y., et al. "Structure of laser-induced shock wave in water", Japan Society for the Promotion of Science, 2016.

Shen, Y., et al. "Theoretical and experimental studies of directivity of sound field generated by pulsed laser induced breakdown in liquid water", SPIE, 2013, pp. 8796141-8796148, vol. 8796, SPIE.

Preisack, M., et al. "Ultrafast imaging of tissue ablation by a XeCl excimer laser in saline", Lasers in Surgery and Medicine, 1992, pp. 520-527, vol. 12, Wiley-Liss Inc.

Versluis, M., et al. "How Snapping Shrimp Snap: Through Cavitat-ing Bubbles", Science Mag, 2000, pp. 2114-2117, vol. 289, Ameri-can Association for the Advancement of Science, Washington DC, USA.

Yan, D., et al. "Study of the Electrical Characteristics, Shock-Wave Pressure Characteristics, and Attenuation Law Based on Pulse Discharge in Water", Shock and Vibration, 2016, pp. 1-11, vol. 2016, Article ID 6412309, Hindawi Publishing Corporation.

Zhang, Q., et al. "Improved Instruments and Methods for the Photographic Study of Spark-Induced Cavitation Bubbles", Water, 2018, pp. 1-12, vol. 10, No. 1683.

"Damage threshold of fiber facets", NKT Photonics, 2012, pp. 1-4, Denmark.

(56)             References Cited

OTHER PUBLICATIONS

Smith, A., et al. "Bulk and surface laser damage of silica by picosecond and nanosecond pulses at 1064 nm", Applied Optics, 2008, pp. 4812-4832, vol. 47, No. 26, Optical Society of America.

Smith, A., et al. "Deterministic Nanosecond Laser-Induced Breakdown Thresholds In Pure and Yb3 Doped Fused Silica", SPIE, 2007, pp. 6453171-64531712, vol. 6453, SPIE.

Sun, X., et al. "Laser Induced Damage to Large Core Optical Fiber by High Peak Power Laser", Specialty Photonics Division, 2010.

Smith, A., et al. "Nanosecond laser-induced breakdown in pure and Yb3 doped fused silica", SPIE, 2007, vol. 6403, SPIE.

Smith, A., et al. "Optical Damage Limits to Pulse Energy From Fibers", IEEE Journal of Selected Topics in Quantum Electronics, 2009, pp. 153-158, vol. 15, No. 1, IEEE.

Reichel, E., et al. "A Special Irrigation Liquid to Increase the Reliability of Laser-Induced Shockwave Lithotripsy", Lasers in Surgery and Medicine, 1992, pp. 204-209, vol. 12, Wiley-Liss Inc., Graz, Austria.

Reichel, E., et al. "Bifunctional irrigation liquid as an ideal energy converter for laser lithotripsy with nanosecond laser pulses", SPIE Lasers in Urology, Laparoscopy, and General Surgery, 1991, pp. 129-133, vol. 1421, SPIE.

Reichel, E., et al. "Laser-induced Shock Wave Lithotripsy with a Regenerative Energy Converter", Lasers in Medical Science, 1992, pp. 423-425, vol. 7, Bailliere Tindall.

Hardy, L., et al. "Cavitation Bubble Dynamics during Thulium Fiber Laser Lithotripsy", SPIE BiOS, 2016, vol. 9689, SPIE.

Deckelbaum, L., "Coronary Laser Angioplasty", Lasers in Surgery and Medicine, 1994, pp. 101-110, vol. 14, Wiley-Liss Inc., Conneticuit, USA.

Shangguan, H., et al. "Effects of Material Properties on Laser-induced Bubble Formation in Absorbing Liquids and On Submerged Targets", Diagnostic and Therapeutic Cardiovascular Interventions VII, SPIE, 1997, pp. 783-791, vol. 2869, SPIE.

Van Leeuwen, T., et al. "Excimer Laser Induced Bubble: Dimensions, Theory, and Implications for Laser Angioplasty", Lasers in Surgery and Medicine, 1996, pp. 381-390, vol. 18, Wiley-Liss Inc., The Netherlands.

Vogel, A., et al. "Shock Wave Emission and Cavitation Bubble Generation by Picosecond and Nanosecond Optical Breakdown in Water", The Journal of Acoustical Society of America, 1996, pp. 148-165, vol. 100, No. 1, The Acoustical Society of America.

Varghese, B., et al. "Influence of absorption induced thermal initiation pathway on irradiance threshold for laser induced breakdown", Biomedical Optics Express, 2015, vol. 6, No. 4, Optical Society of America.

Linz, N., et al. "Wavelength dependence of nanosecond infrared laser-induced breakdown in water: Evidence for multiphoton initiation via an intermediate state", Physical Review, 2015, pp. 134114.1-1341141.10, vol. 91, American Physical Society.

International Search Report and Written Opinion dated Jun. 27, 2018, in PCT Application Serial No. PCT/US2018/027121.

International Search Report and Written Opinion dated Jul. 20, 2018, in PCT Application Serial No. PCT/US2018/027801.

International Search Report and Written Opinion dated Jul. 20, 2018, in PCT Application Serial No. PCT/US2018/027784.

European Search Report, for European Patent No. 18185152, mailed Dec. 13, 2018.

International Search Report and Written Opinion dated May 22, 2019, in PCT Application Serial No. PCT/US2019/022009.

International Search Report and Written Opinion dated May 29, 2019, in PCT Application Serial No. PCT/US2019/022016.

International Search Report and Written Opinion dated Jun. 22, 2018, in Application Serial No. NL2019807, issued by the European Patent Office.

Noimark, Sacha, et al., "Carbon-Nanotube-PDMS Composite Coatings on Optical Fibers for All-Optical Ultrasound Imaging", Advanced Functional Materials, 2016, pp. 8390-8396, vol. 26, Wiley-Liss Inc.

Chen, Sung-Liang, "Review of Laser-Generated Ultrasound Transmitters and their Applications to All-Optical Ultrasound Transducers and Imaging", Appl. Sci. 2017, 7, 25.

Colchester, R., et al. "Laser-Generated ultrasound with optica fibres using functionalised carbon nanotube composite coatings", Appl. Phys. Lett., 2014, vol. 104, 173504, American Institute of Physics.

Poduval, R., et al. "Optical fiber ultrasound transmitter with electrospun carbon nanotube-polymer composite", Appl. Phys. Lett., 2017, vol. 110, 223701, American Institute of Physics.

Tian, J., et al. "Distributed fiber-optic laser-ultrasound generation based on ghost-mode of tilted fiber Bragg gratings", Optics Express, Mar. 2013, pp. 6109-6114, vol. 21, No. 5, Optical Society of America.

Kim, J., et al. "Optical Fiber Laser-Generated-Focused-Ultrasound Transducers for Intravascular Therapies", IEEE, 2017.

Kang, H., et al. "Enhanced photocoagulation with catheter-based diffusing optical device", Journal of Biomedical Optics, 2012, vol. 17, Issue 11, 118001, SPIE.

International Search Report and Written Opinion dated Jan. 3, 2020, in PCT Application Serial No. PCT/US2019/056579.

Communication Pursuant to Article 94(3) EPC, for European Patent Application No. 18185152.8, mailed Jan. 16, 2019.

European Search Report, for European Patent Application No. 18185152.8, mailed Dec. 20, 2018.

International Search Report and Written Opinion dated Jul. 29, 2020 in PCT Application Serial No. PCT/US2020/034005.

International Search Report and Written Opinion dated Sep. 11, 2020 in PCT Application Serial No. PCT/US2020/038517.

International Search Report and Written Opinion dated Sep. 9, 2020 in PCT Application Serial No. PCT/US2020/038530.

International Search Report and Written Opinion dated Sep. 11, 2020 in PCT Application Serial No. PCT/US2020/038521.

International Search Report and Written Opinion dated Sep. 7, 2020 in PCT Application Serial No. PCT/US2020/034642.

International Preliminary Report on Patentability dated Sep. 15, 2020 in PCT Application Serial No. PCT/US2019/022009.

International Search Report and Written Opinion dated Sep. 14, 2020 in PCT Application Serial No. PCT/US2020/038523.

International Search Report and Written Opinion dated Oct. 2, 2020 in PCT Application Serial No. PCT/US2020/036107.

Schafter+Kirchhoff, Laser Beam Couplers series 60SMS for coupling into single-mode and polarization-maintaining fiber cables, Schafter+Kirchhoff, pp. 1-5, Germany. Dec. 2, 2021.

International Search Report and Written Opinion dated Jan. 29, 2020 in PCT Application Serial No. PCT/US2020/059961.

International Search Report and Written Opinion dated Jan. 20, 2020 in PCT Application Serial No. PCT/US2020/054792.

Partial Search Report and Provisional Opinion dated Feb. 19, 2021 in PCT Application Serial No. PCT/US2020/059960.

Shariat, Mohammad H., et al. "Localization of the ectopic spiral electrical source using intracardiac electrograms during atrial fibrillation." 2015 IEEE 28th Canadian Conference on Electrical and Computer Engineering (CCECE). IEEE, 2015.

Nademanee, Koonlawee, et al. "A new approach for catheter ablation of atrial fibrillation: mapping of the electrophysiologic substrate." Journal of the American College of Cardiology 43.11 (2004): 2044-2053.

Calkins, Hugh. "Three dimensional mapping of atrial fibrillation: techniques and necessity." Journal of interventional cardiac electrophysiology 13.1 (2005): 53-59.

Shariat, Mohammad Hassan. Processing the intracardiac electrogram for atrial fibrillation ablation. Diss. Queen's University (Canada), 2016.

Meng et al., "Accurate Recovery Of Atrial Endocardial Potential Maps From Non-contact Electrode Data." Auckland Bioengineering Institute. (ID 1421). May 2019.

Jiang et al., "Multielectrode Catheter For Substrate Mapping For Scar-related VT Ablation: A Comparison Between Grid Versus Linear Configurations." UChicago Medicine, Center for Arrhythmia Care, Chicago IL (ID 1368). Poster for conference in San Francisco, May 8-11, 2019.

Sacher et al., "Comparison Of Manual Vs Automatic Annotation To Identify Abnormal Substrate For Scar Related VT Ablation." LIRYC

(56) References Cited

OTHER PUBLICATIONS

Institute, Bordeaux University Hospital, France (ID 1336). Poster for conference in San Francisco, May 8-11, 2019.

Oriel Instruments, "Introduction to Beam Splitters for Optical Research Applications", Apr. 2014, pp. 1-9, https://www.azoptics.com/Article.aspx?ArticaID=871.

International Search Report and Written Opinion dated Apr. 12, 2021 in PCT Application Serial No. PCT/US2020/059960.

International Search Report and Written Opinion dated Apr. 13, 2021 in PCT Application Serial No. PCT/US2020/064846.

International Search Report and Written Opinion dated Apr. 13, 2021 in PCT Application Serial No. PCT/US2021/013944.

International Search Report and Written Opinion dated May 25, 2021 in PCT Application Serial No. PCT/US2021/017604.

International Search Report and Written Opinion dated Jun. 2, 2021 in PCT Application Serial No. PCT/US2021/018522.

International Search Report and Written Opinion dated Jun. 2, 2021 in PCT Application Serial No. PCT/US2021/015204.

International Search Report and Written Opinion dated Jun. 17, 2021 in PCT Application Serial No. PCT/US2021/020934.

International Search Report and Written Opinion dated Jul. 13, 2021 in PCT Application Serial No. PCT/US2021/024216.

International Search Report and Written Opinion dated Jun. 22, 2021 in PCT Application Serial No. PCT/US2021/020937.

International Search Report and Written Opinion dated Jun. 24, 2021 in PCT Application Serial No. PCT/US2021/021272.

International Search Report and Written Opinion dated Aug. 20, 2021 in PCT Application Serial No. PCT/US2021/031130.

International Search Report and Written Opinion dated Apr. 4, 2022 in PCT Application Serial No. PCT/US2021/062170.

International Search Report and Written Opinion dated Apr. 4, 2022 in PCT Application Serial No. PCT/US2021/065073.

Partial Search Report and Provisional Opinion dated May 3, 2022 in PCT Application No. PCT/US2022/015577.

International Search Report and Written Opinion dated May 13, 2022 in PCT Application Serial No. PCT/US2022/017562.

International Search Report and Written Opinion dated Jun. 28, 2022, in PCT Application Serial No. PCT/US2022/015577.

International Search Report and Written Opinion dated Jun. 27, 2022, in PCT Application Serial No. PCT/US2022/022460.

International Search Report and Written Opinion dated Aug. 25, 2022 in PCT Application Serial No. PCT US/2022/028035.

International Search Report and Written Opinion dated Sep. 15, 2022 in PCT Application Serial No. PCT US/2022/032045.

International Search Report and Written Opinion dated Nov. 8, 2022 in PCT Application Serial No. PCT US/2022/039678.

International Search Report and Written Opinion, PCT Application Serial No. PCT/US2022/047751 issued Feb. 10, 2023, by the European Patent Office. (56PCT).

International Search Report and Written Opinion, PCT Application Serial No. PCT/US2022/047691 issued Feb. 13, 2023, by the European Patent Office. (53PCT).

Accucoat, "Beamsplitter: Divide, combine & conquer"; 2023.

Lin et al., "Photoacoustic imaging", Science Direct; 2021.

Zhou et al., "Photoacoustic Imaging with fiber optic technology: A review", Science Direct; 2020.

International Search Report and Written Opinion issued by the European Patent Office, for Serial No. PCT/US2022/053775, dated Apr. 21, 2023. (Re 45PCT).

International Search Report and Written Opinion issued by the European Patent Office, for Serial No. PCT/US2023/011497, dated Apr. 28, 2023. (Re 54PCT).

International Search Report and Written Opinion issued by the European Patent Office, for Serial No. PCT/US2023/012599, dated May 19, 2023. (Re 57PCT).

PathFinder Digital, "Free Space Optics vs. Fiber Optics", 2023.

International Search Report and Written Opinion, issued in Application Serial No. PCT/US2023/016152, dated Jul. 12, 2023.

Shen, Yajie et al. "High-peak-power and narrow-linewidth Q-switched Ho: YAG laser in-band pumped at 1931 nm." Applied Physics Express 13.5 (2020): 052006. (Year 2020).

"Custom Medical Skived Tubing", Duke Extrusion, 2025. https://www.dukeextrusion.com/tubing-options/skived-tubing.

Definition of ablation—NCI Dictionary of Cancer Terms—NCI, National Cancer Institute, p. 1 (Year:2025).

Daemen, J., Tovar Forero, M.N, "The Coronary Intravascular Lithotripsy System", ICR Journal, 2019; 14(3); 174-181.

Butt, N., Khalid, N., Shlofmitz, E., "Intravascular Lithotripsy"; NCBI Bookshelf. A service of the National Library of Medicine, National Institutes of Health; StatPearls Publishing, 2023.

* cited by examiner

ACTIVE ALIGNMENT SYSTEM AND METHOD FOR OPTIMIZING OPTICAL COUPLING OF MULTIPLEXER FOR LASER-DRIVEN INTRAVASCULAR LITHOTRIPSY DEVICE

RELATED APPLICATIONS

This application is a continuation application of and claims priority on U.S. patent application Ser. No. 17/308,934, filed on May 5, 2021, and entitled "ACTIVE ALIGNMENT SYSTEM AND METHOD FOR OPTIMIZING OPTICAL COUPLING OF MULTIPLEXER FOR LASER-DRIVEN INTRAVASCULAR LITHOTRIPSY DEVICE". Additionally, U.S. patent application Ser. No. 17/308,934 claims priority on U.S. Provisional Application Ser. No. 63/023,669, filed on May 12, 2020. As far as permitted, the contents of U.S. patent application Ser. No. 17/308,934 and U.S. Provisional Application Ser. No. 63/023,669 are incorporated in their entirety herein by reference.

BACKGROUND

Vascular lesions within vessels in the body can be associated with an increased risk for major adverse events, such as myocardial infarction, embolism, deep vein thrombosis, stroke, and the like. Severe vascular lesions can be difficult to treat and achieve patency for a physician in a clinical setting.

Vascular lesions may be treated using interventions such as drug therapy, balloon angioplasty, atherectomy, stent placement, vascular graft bypass, to name a few. Such interventions may not always be ideal or may require subsequent treatment to address the lesion.

SUMMARY

The present invention is directed toward a catheter system for treating a treatment site within or adjacent to a vessel wall or heart valve. In various embodiments, the catheter system includes a first light source, a plurality of light guides, a multiplexer, a multiplexer alignment system, and a first beamsplitter. The first light source generates a source beam. The plurality of light guides are each configured to alternatively receive the source beam from the first light source. Each light guide has a guide proximal end. The multiplexer receives the source beam from the first light source. The multiplexer alternatively directs the source beam from the first light source to each of the plurality of light guides. The multiplexer alignment system is operatively coupled to the multiplexer. The multiplexer alignment system includes a second light source that generates a probe source beam that is directed by the multiplexer alignment system to scan across the guide proximal end of each of the plurality of light guides so that a time is determined to generate the source beam so that the source beam is optically coupled to the guide proximal end of each of the plurality of light guides. The first beamsplitter receives (i) the source beam from the first light source, and (ii) the probe source beam from the second light source. The first beamsplitter is configured to alternately direct the probe source beam and the source beam toward the guide proximal end of each of the plurality of light guides.

In many embodiments, the multiplexer alignment system is operatively coupled to the multiplexer so that the probe source beam is directed to scan across the guide proximal end of each of the plurality of light guides at a predetermined time prior to the source beam being directed toward the guide proximal end of each of the plurality of light guides.

In several embodiments, the probe source beam is offset from the source beam as the probe source beam is directed to scan across the guide proximal end of each of the plurality of light guides and the source beam is directed toward the guide proximal end of each of the plurality of light guides.

In some embodiments, the multiplexer alignment system further includes coupling optics that are configured to focus the probe source beam to scan across the guide proximal end of each of the plurality of light guides.

In certain embodiments, the multiplexer is configured to utilize the coupling optics to alternatively focus the source beam on the guide proximal end of each of the plurality of light guides.

In one embodiment, the first beamsplitter includes a dichroic beamsplitter.

In some embodiments, the first beamsplitter is configured to transmit one of the source beam and the probe source beam and to reflect the other of the source beam and the probe source beam.

In certain embodiments, the probe source beam being directed by the multiplexer alignment system to scan across the guide proximal end of each of the plurality of light guides produces a backscattered energy beam that is scattered off of the guide proximal end of each of the plurality of light guides. In some embodiments, the catheter system further includes a system controller that analyzes the backscattered energy beam to determine optical coupling between the guide beams and the plurality of light guides.

In certain embodiments, the system controller is configured to control operation of the first light source to generate pulses of light energy.

In some embodiments, the catheter system further includes a second beamsplitter and a photodetector, the second beamsplitter being configured to (i) receive the backscattered energy beam, and (ii) direct at least a portion of the backscattered energy beam toward the photodetector.

In certain embodiments, the photodetector generates a signal based at least in part on the at least a portion of the backscattered energy beam that is directed toward the photodetector.

In some embodiments, the catheter system further includes an amplifier and signal processing electronics. In certain embodiments, the amplifier is configured to amplify the signal from the photodetector to provide an amplified signal that is directed to the signal processing electronics to determine an intensity of light energy contained within the backscattered energy beam.

In some embodiments, the intensity of light energy contained within the backscattered energy beam is evaluated to determine optimal optical coupling between the guide beams and the plurality of light guides.

In certain embodiments, the multiplexer includes (i) a multiplexer base, (ii) a multiplexer stage that is movably supported on the multiplexer base, (iii) a stage mover that is configured to move the multiplexer stage in a single linear degree of freedom relative to the multiplexer base, and (iv) a redirector that is mounted on the multiplexer stage. In some embodiments, movement of the multiplexer stage relative to the multiplexer base results in corresponding movement of the redirector relative to the multiplexer base.

In certain embodiments, the multiplexer further includes coupling optics that are mounted on the multiplexer stage, the coupling optics being configured to alternatively focus the source beam on the guide proximal end of each of the plurality of light guides. In some embodiments, the source beam being received by the multiplexer initially impinges on the redirector, the redirector being configured to redirect the source beam toward the coupling optics.

In some embodiments, the plurality of light guides are retained at least partially within a guide coupling housing. In certain embodiments, the probe source beam is directed by the multiplexer alignment system to scan across a face of the guide coupling housing.

In some embodiments, the guide proximal end of each of the plurality of light guides is retained within the guide coupling housing.

In many embodiments, the first light source includes a laser. In several embodiments, the second light source includes a laser.

The present invention is further directed toward a method for treating a treatment site within or adjacent to a vessel wall or a heart valve, the method including utilizing the catheter system as described above.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

Figure 1:
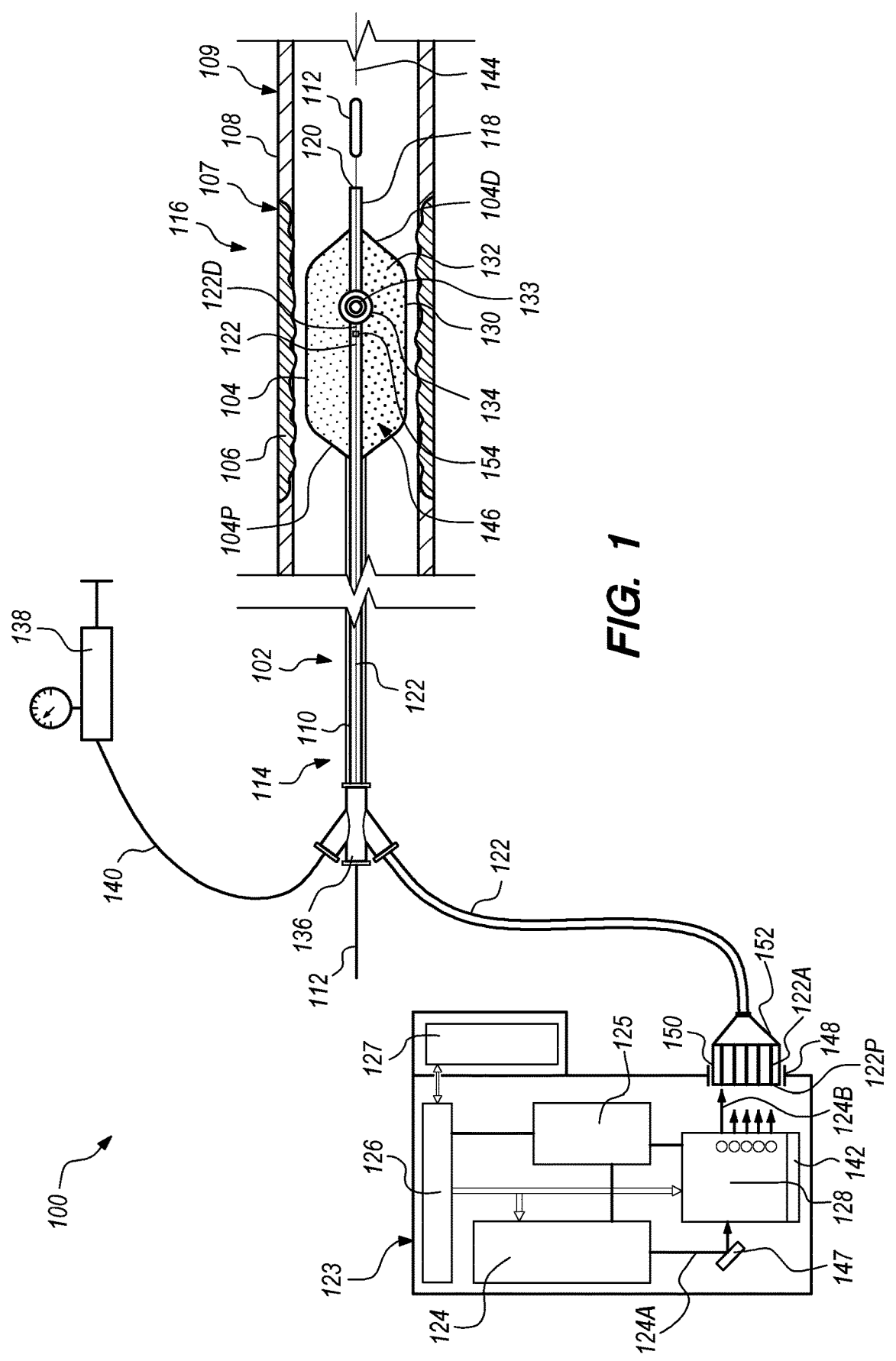
FIG. 1 is a schematic cross-sectional view of an embodiment of a catheter system in accordance with various embodiments herein, the catheter system including a first light source, a plurality of light guides, a multiplexer, and a multiplexer alignment system.

While embodiments of the present invention are susceptible to various modifications and alternative forms, specifics thereof have been shown by way of example and drawings, and are described in detail herein. It is understood, however, that the scope herein is not limited to the particular embodiments described. On the contrary, the intention is to cover modifications, equivalents, and alternatives falling within the spirit and scope herein.

DESCRIPTION

Treatment of vascular lesions can reduce major adverse events or death in affected subjects. As referred to herein, a major adverse event is one that can occur anywhere within the body due to the presence of a vascular lesion. Major adverse events can include, but are not limited to, major adverse cardiac events, major adverse events in the peripheral or central vasculature, major adverse events in the brain, major adverse events in the musculature, or major adverse events in any of the internal organs.

For the treatment of vascular lesions, such as calcium deposits in arteries, it is generally beneficial to be able to treat multiple closely spaced areas with a single insertion and positioning of a catheter balloon. To allow this to occur within an optical excitation system, such as within a laser-driven intravascular lithotripsy device, it is usually desirable to have a number of output channels, e.g., optical fibers and targets, for the treatment process, each output channel including an emitter, e.g., a plasma generator, which can be distributed at appropriate and desired locations within the balloon. Since a high-power laser source is often the largest and most expensive component in the system, having a dedicated laser source for each optical fiber is unlikely to be feasible for a number of reasons including packaging requirements, power consumption, thermal considerations, and economics. For such reasons, it can be advantageous to multiplex a single laser simultaneously and/or sequentially into a number of different optical fibers for treatment purposes. This allows the possibility for using all or a particular portion of the laser power from the single laser with each fiber.

Thus, the catheter systems and related methods disclosed herein are configured to provide a means to power multiple fiber optic channels in a laser-driven pressure wave-generating device that is designed to impart pressure onto and induce fractures in vascular lesions, such as calcified vascular lesions and/or fibrous vascular lesions, using a single light source. More particularly, the invention described in detail herein includes a multiplexer that multiplexes a single energy source or light source, e.g., a single laser source, into one or more of multiple light guides, e.g., fiber optic channels, in a single-use device.

As described in detail herein, the catheter systems and methods of the present invention further incorporate a means to improve optical coupling to an individual output channel, e.g., optical fiber, which is organized in a multi-channel array. The active optical system measures coupling efficiency continuously during the action of the multiplexer and determines the optimal parameters to trigger the energy source. For example, in various embodiments, the present invention incorporates a second energy source to probe the face of the multi-channel array and the individual optical fibers within the multi-channel array. The source is coupled to a common path with the beam of the primary energy source. The focused probe beam spot can be coincident with the primary energy spot or offset to provide scan ahead timing giving the system predictable control over firing of the primary energy source, e.g., the laser. The focused probe beam spot scatters off the face of the multi-channel array and the individual optical fibers. Optics and sensors allow continuous monitoring of the light returned from the probe beam spot. The relative intensity of the returned light correlates and a corresponding signal produced by signal processing electronics correlate to coupling efficiency. As such, the scanning process generates a data stream from which coupling efficiency as a function of multiplexer position is determined. In certain embodiments, the projected spot from the primary energy source laser is configured to lag that of the probe spot in a tightly controlled or calibrated manner. Thus, the system controls parametric motion of the multiplexer and computes optimal time to fire the primary energy source once the multiplexer is in the optimal location. In other embodiments, the probe beam spot can be utilized within an active scanning system that goes through every fiber and finds the X-Y location for each fiber that gives optimal coupling, and doing this without firing the main energy source. Thus, the second energy source could go slowly and do a thorough X-Y scan across the face of the multi-channel array and map the whole thing out. The system would then store that information and use those locations for real-time firing of the primary energy source.

With such designs, the systems and methods of the present invention can be implemented for any multiplexer configuration, either linear, circular, patterned or scanned, provided that the probe and primary laser beams can be combined and spot traced by beam paths, which can then be correlated to parametric motion of the multiplexer mechanism.

It is appreciated that the catheter system and methods of the present invention provide various advantages and/or solves key problems including one or more of: 1) reducing system optical coupling dependence on mechanical tolerances of the output channels (optical fibers) and tolerances of their location in a multi-channel array, 2) reducing performance dependence on the accuracy of connecting and aligning the multi-channel array to the multiplexer, 3) reducing dependence on the accuracy of the positioning mechanism in the multiplexer and the associated quality and precision of its optical and mechanical components, 4) improving speed and performance of the multiplexer and the multi-channel array system, and 5) making it possible to use low cost, low accuracy multi-channel arrays on the single-use device, thereby improving cost targets.

In various embodiments, the catheter systems disclosed herein can include a catheter configured to advance to the treatment site within or adjacent a blood vessel or heart valve within the body of a patient. The catheter includes a catheter shaft, and a balloon that is coupled and/or secured to the catheter shaft. The balloons herein can include a balloon wall that defines a balloon interior and can be configured to receive a balloon fluid within the balloon interior to expand from a deflated configuration suitable for advancing the catheter through a patient's vasculature, to an inflated configuration suitable for anchoring the catheter in position relative to the treatment site. The catheter systems also include the plurality of light guides disposed along the catheter shaft and within the balloon. Each light guide can be configured for generating pressure waves within the balloon for disrupting the vascular lesions.

In various embodiments, the catheter systems and related methods of the present invention utilize a high energy source, e.g., a light source such as a high energy laser source or another suitable high energy source, which provides energy that is guided by an energy guide, e.g., a light guide, to create a localized plasma in the balloon fluid that is retained within a balloon interior of an inflatable balloon of the catheter. As such, the energy guide can sometimes be referred to as, or can be said to incorporate a "plasma generator" at or near a guide distal end of the energy guide that is positioned within the balloon interior. The creation of the localized plasma, in turn, induces a high energy bubble inside the balloon interior to create pressure waves to impart pressure onto and induce fractures in a treatment site, such as a calcified vascular lesion or a fibrous vascular lesion, at a treatment site within or adjacent to a blood vessel wall within a body of a patient.

In some embodiments, the energy source can be configured to provide sub-millisecond pulses of energy, e.g., light energy, from the energy source to initiate plasma formation in the balloon fluid within the balloon to cause rapid bubble formation and to impart pressure waves upon the balloon wall at the treatment site. Thus, the pressure waves can transfer mechanical energy through an incompressible balloon fluid to the treatment site to impart a fracture force on the treatment site. As used herein, the treatment site can include a vascular lesion such as a calcified vascular lesion or a fibrous vascular lesion, typically found in a blood vessel and/or a heart valve.

As used herein, the terms "intravascular lesion", "vascular lesion" and "treatment site" are used interchangeably unless otherwise noted. As such, the intravascular lesions and/or the vascular lesions are sometimes referred to herein simply as "lesions".

Those of ordinary skill in the art will realize that the following detailed description of the present invention is illustrative only and is not intended to be in any way limiting. Other embodiments of the present invention will readily suggest themselves to such skilled persons having the benefit of this disclosure. Reference will now be made in detail to implementations of the present invention as illustrated in the accompanying drawings.

In the interest of clarity, not all of the routine features of the implementations described herein are shown and described. It will, of course, be appreciated that in the development of any such actual implementation, numerous implementation-specific decisions must be made in order to achieve the developer's specific goals, such as compliance with application-related and business-related constraints, and that these specific goals will vary from one implementation to another and from one developer to another. Moreover, it is appreciated that such a development effort might be complex and time-consuming, but would nevertheless be a routine undertaking of engineering for those of ordinary skill in the art having the benefit of this disclosure.

It is appreciated that the catheter systems disclosed herein can include many different forms. Referring now to FIG. 1, a schematic cross-sectional view is shown of a catheter system 100 in accordance with various embodiments herein. As described herein, the catheter system 100 is suitable for imparting pressure to induce fractures in one or more treatment sites within or adjacent a vessel wall of a blood vessel or heart valve within a body of a patient. In the embodiment illustrated in FIG. 1, the catheter system 100 can include one or more of a catheter 102, a light guide bundle 122 including one or more (and preferably a plurality of) light guides 122A, a source manifold 136, a fluid pump 138, and a system console 123 including one or more of a light source 124 (sometimes referred to herein as a "first light source"), a power source 125, a system controller 126, a graphic user interface 127 (a "GUI"), a multiplexer 128, and a multiplexer alignment system 142. Alternatively, the catheter system 100 can include more components or fewer components than those specifically illustrated in FIG. 1.

The catheter 102 is configured to move to a treatment site 106 within or adjacent to a blood vessel 108 within a body 107 of a patient 109. The treatment site 106 can include one or more vascular lesions such as calcified vascular lesions, for example. Additionally, or in the alternative, the treatment site 106 can include vascular lesions such as fibrous vascular lesions.

The catheter 102 can include an inflatable balloon 104 (sometimes referred to herein simply as a "balloon"), a catheter shaft 110 and a guidewire 112. The balloon 104 can be coupled to the catheter shaft 110. The balloon 104 can include a balloon proximal end 104P and a balloon distal end 104D. The catheter shaft 110 can extend from a proximal portion 114 of the catheter system 100 to a distal portion 116 of the catheter system 100. The catheter shaft 110 can include a longitudinal axis 144. The catheter shaft 110 can also include a guidewire lumen 118 which is configured to move over the guidewire 112. The catheter shaft 110 can further include an inflation lumen (not shown). In some embodiments, the catheter 102 can have a distal end opening 120 and can accommodate and be tracked over the guidewire 112 as the catheter 102 is moved and positioned at or near the treatment site 106. In some embodiments, the balloon proximal end 104P can be coupled to the catheter shaft 110, and the balloon distal end 104D can be coupled to the guidewire lumen 118.

The catheter shaft 110 of the catheter 102 can be coupled to the one or more light guides 122A of the light guide bundle 122 that are in optical communication with the light source 124. The light guide(s) 122A can be disposed along the catheter shaft 110 and within the balloon 104. Additionally, each of the light guides 122A can have a guide distal end 122D that is at any suitable longitudinal position relative to a length of the balloon 104. In some embodiments, each light guide 122A can be an optical fiber and the light source 124 can be a laser. The light source 124 can be in optical communication with the light guides 122A at the proximal portion 114 of the catheter system 100. More particularly, as described in detail herein, the light source 124 can selectively and/or alternatively be in optical communication with each of the light guides 122A in any desired combination, order and/or pattern due to the presence and operation of the multiplexer 128. Additionally, as described herein, the light source 124 can be more precisely and accurately coupled in optical communication with each of the light guides 122A due to the presence of the multiplexer alignment system 142.

In some embodiments, the catheter shaft 110 can be coupled to multiple light guides 122A such as a first light guide, a second light guide, a third light guide, etc., which can be disposed at any suitable positions about the guidewire lumen 118 and/or the catheter shaft 110. For example, in certain non-exclusive embodiments, two light guides 122A can be spaced apart by approximately 180 degrees about the circumference of the guidewire lumen 118 and/or the catheter shaft 110; three light guides 122A can be spaced apart by approximately 120 degrees about the circumference of the guidewire lumen 118 and/or the catheter shaft 110; or four light guides 122A can be spaced apart by approximately 90 degrees about the circumference of the guidewire lumen 118 and/or the catheter shaft 110. Still alternatively, multiple light guides 122A need not be uniformly spaced apart from one another about the circumference of the guidewire lumen 118 and/or the catheter shaft 110. More particularly, it is further appreciated that the light guides 122A described herein can be disposed uniformly or non-uniformly about the guidewire lumen 118 and/or the catheter shaft 110 to achieve the desired effect in the desired locations.

The balloon 104 can include a balloon wall 130 that defines a balloon interior 146, and can be inflated with a balloon fluid 132 to expand from a deflated configuration suitable for advancing the catheter 102 through a patient's vasculature, to an inflated configuration suitable for anchoring the catheter 102 in position relative to the treatment site 106. Stated in another manner, when the balloon 104 is in the inflated configuration, the balloon wall 130 of the balloon 104 is configured to be positioned substantially adjacent to the treatment site 106, i.e. to the vascular lesion(s). It is appreciated that although FIG. 1 illustrates the balloon wall 130 of the balloon 104 being shown spaced apart from the treatment site 106 of the blood vessel 108, this is done merely for ease of illustration, and the balloon wall 130 of the balloon 104 will typically be substantially directly adjacent to the treatment site 106 when the balloon is in the inflated configuration.

In some embodiments, the light source 124 of the catheter system 100 can be configured to provide sub-millisecond pulses of light from the light source 124, along the light guides 122A, to a location within the balloon interior 146 of the balloon 104, thereby inducing plasma formation in the balloon fluid 132 within the balloon interior 146 of the balloon 104, i.e. via a plasma generator 133 (illustrated in phantom) located at a guide distal end 122D of each of the light guides 122A. The plasma formation causes rapid bubble formation, and imparts pressure waves upon the treatment site 106. Exemplary plasma-induced bubbles are shown as bubbles 134 in FIG. 1.

The balloons 104 suitable for use in the catheter systems 100 described in detail herein include those that can be passed through the vasculature of a patient when in the deflated configuration. In some embodiments, the balloons 104 herein are made from silicone. In other embodiments, the balloons 104 herein are made from polydimethylsiloxane (PDMS), polyurethane, polymers such as PEBAX™ material available from Arkema, which has a location at King of Prussia, Pennsylvania, USA, nylon, and the like. In some embodiments, the balloons 104 can include those having diameters ranging from one millimeter (mm) to 25 mm in diameter. In some embodiments, the balloons 104 can include those having diameters ranging from at least 1.5 mm to 12 mm in diameter. In some embodiments, the balloons 104 can include those having diameters ranging from at least one mm to five mm in diameter.

Additionally, in some embodiments, the balloons 104 herein can include those having a length ranging from at least five mm to 300 mm. More particularly, in some embodiments, the balloons 104 herein can include those having a length ranging from at least eight mm to 200 mm. It is appreciated that balloons 104 of greater length can be positioned adjacent to larger treatment sites 106, and, thus, may be usable for imparting pressure onto and inducing fractures in larger vascular lesions or multiple vascular lesions at precise locations within the treatment site 106.

Further, the balloons 104 herein can be inflated to inflation pressures of between approximately one atmosphere (atm) and 70 atm. In some embodiments, the balloons 104 herein can be inflated to inflation pressures of from at least 20 atm to 70 atm. In other embodiments, the balloons 104 herein can be inflated to inflation pressures of from at least six atm to 20 atm. In still other embodiments, the balloons 104 herein can be inflated to inflation pressures of from at least three atm to 20 atm. In yet other embodiments, the balloons 104 herein can be inflated to inflation pressures of from at least two atm to ten atm.

Still further, the balloons 104 herein can include those having various shapes, including, but not to be limited to, a conical shape, a square shape, a rectangular shape, a spherical shape, a conical/square shape, a conical/spherical shape, an extended spherical shape, an oval shape, a tapered shape, a bone shape, a stepped diameter shape, an offset shape, or a conical offset shape. In some embodiments, the balloons 104 herein can include a drug eluting coating or a drug eluting stent structure. The drug eluting coating or drug eluting stent can include one or more therapeutic agents including anti-inflammatory agents, anti-neoplastic agents, anti-angiogenic agents, and the like.

The balloon fluid 132 can be a liquid or a gas. Exemplary balloon fluids 132 suitable for use herein can include, but are not limited to one or more of water, saline, contrast medium, fluorocarbons, perfluorocarbons, gases, such as carbon dioxide, and the like. In some embodiments, the balloon fluids 132 described can be used as base inflation fluids. In some embodiments, the balloon fluids 132 include a mixture of saline to contrast medium in a volume ratio of 50:50. In other embodiments, the balloon fluids 132 include a mixture of saline to contrast medium in a volume ratio of 25:75. In still other embodiments, the balloon fluids 132 include a mixture of saline to contrast medium in a volume ratio of 75:25. Additionally, the balloon fluids 132 suitable for use herein can be tailored on the basis of composition, viscosity, and the like in order to manipulate the rate of travel of the pressure waves therein. In certain embodiments, the balloon fluids 132 suitable for use herein are biocompatible. A volume of balloon fluid 132 can be tailored by the chosen light source 124 and the type of balloon fluid 132 used.

In some embodiments, the contrast agents used in the contrast media herein can include, but are not to be limited to, iodine-based contrast agents, such as ionic or non-ionic iodine-based contrast agents. Some non-limiting examples of ionic iodine-based contrast agents include diatrizoate, metrizoate, iothalamate, and ioxaglate. Some non-limiting examples of non-ionic iodine-based contrast agents include iopamidol, iohexol, ioxilan, iopromide, iodixanol, and ioversol. In other embodiments, non-iodine based contrast agents can be used. Suitable non-iodine containing contrast agents can include gadolinium (III)-based contrast agents. Suitable fluorocarbon and perfluorocarbon agents can include, but are not to be limited to, agents such as the perfluorocarbon dodecafluoropentane (DDFP, C5F12).

Additionally, the balloon fluids 132 herein can include those that include absorptive agents that can selectively absorb light in the ultraviolet region (e.g., at least ten nanometers (nm) to 400 nm), the visible region (e.g., at least 400 nm to 780 nm), or the near-infrared region (e.g., at least 780 nm to 2.5 μm) of the electromagnetic spectrum. Suitable absorptive agents can include those with absorption maxima along the spectrum from at least ten nm to 2.5 μm. Alternatively, the balloon fluids 132 can include those that include absorptive agents that can selectively absorb light in the mid-infrared region (e.g., at least 2.5 μm to 15 μm), or the far-infrared region (e.g., at least 15 μm to one mm) of the electromagnetic spectrum. In various embodiments, the absorptive agent can be those that have an absorption maximum matched with the emission maximum of the laser used in the catheter system. By way of non-limiting examples, various lasers described herein can include neodymium:yttrium-aluminum-garnet (Nd:YAG— emission maximum=1064 nm) lasers, holmium:YAG (Ho:YAG— emission maximum=2.1 μm) lasers, or erbium:YAG (Er:YAG— emission maximum=2.94 μm) lasers. In some embodiments, the absorptive agents used herein can be water soluble. In other embodiments, the absorptive agents used herein are not water soluble. In some embodiments, the absorptive agents used in the balloon fluids 132 herein can be tailored to match the peak emission of the light source 124. Various light sources 124 having emission wavelengths of at least ten nanometers to one millimeter are discussed elsewhere herein.

It is appreciated that the catheter system 100 and/or the light guide bundle 122 disclosed herein can include any number of light guides 122A in optical communication with the light source 124 at the proximal portion 114, and with the balloon fluid 132 within the balloon interior 146 of the balloon 104 at the distal portion 116. For example, in some embodiments, the catheter system 100 and/or the light guide bundle 122 can include from one light guide 122A to five light guides 122A. In other embodiments, the catheter system 100 and/or the light guide bundle 122 can include from five light guides 122A to fifteen light guides 122A. In yet other embodiments, the catheter system 100 and/or the light guide bundle 122 can include from ten light guides 122A to thirty light guides 122A. Alternatively, in still other embodiments, the catheter system 100 and/or the light guide bundle 122 can include greater than 30 light guides 122A.

The light guides 122A herein can include an optical fiber or flexible light pipe. The light guides 122A herein can be thin and flexible and can allow light signals to be sent with very little loss of strength. The light guides 122A herein can include a core surrounded by a cladding about its circumference. In some embodiments, the core can be a cylindrical core or a partially cylindrical core. The core and cladding of the light guides 122A can be formed from one or more materials, including but not limited to one or more types of glass, silica, or one or more polymers. The light guides 122A may also include a protective coating, such as a polymer. It is appreciated that the index of refraction of the core will be greater than the index of refraction of the cladding.

Each light guide 122A can guide light along its length from a proximal portion, i.e. a guide proximal end 122P, to a distal portion, i.e. the guide distal end 122D, having at least one optical window (not shown) that is positioned within the balloon interior 146. The light guides 122A can create a light path as a portion of an optical network including the light source 124. The light path within the optical network allows light to travel from one part of the network to another. Both the optical fiber and the flexible light pipe can provide a light path within the optical networks herein.

Further, the light guides 122A herein can assume many configurations about and/or relative to the catheter shaft 110 of the catheters 102 described herein. In some embodiments, the light guides 122A can run parallel to the longitudinal axis 144 of the catheter shaft 110. In some embodiments, the light guides 122A can be physically coupled to the catheter shaft 110. In other embodiments, the light guides 122A can be disposed along a length of an outer diameter of the catheter shaft 110. In yet other embodiments, the light guides 122A herein can be disposed within one or more light guide lumens within the catheter shaft 110.

Additionally, it is further appreciated that the light guides 122A can be disposed at any suitable positions about the circumference of the guidewire lumen 118 and/or the catheter shaft 110, and the guide distal end 122D of each of the light guides 122A can be disposed at any suitable longitudinal position relative to the length of the balloon 104 and/or relative to the length of the guidewire lumen 118 to more effectively and precisely impart pressure waves for purposes of disrupting the vascular lesions at the treatment site 106.

Further, the light guides 122A herein can include one or more photoacoustic transducers 154, where each photoacoustic transducer 154 can be in optical communication with the light guide 122A within which it is disposed. In some embodiments, the photoacoustic transducers 154 can be in optical communication with the guide distal end 122D of the light guide 122A. Additionally, in such embodiments, the photoacoustic transducers 154 can have a shape that corresponds with and/or conforms to the guide distal end 122D of the light guide 122A.

The photoacoustic transducer 154 is configured to convert light energy into an acoustic wave at or near the guide distal end 122D of the light guide 122A. It is appreciated that the direction of the acoustic wave can be tailored by changing an angle of the guide distal end 122D of the light guide 122A.

It is further appreciated that the photoacoustic transducers 154 disposed at the guide distal end 122D of the light guide 122A herein can assume the same shape as the guide distal end 122D of the light guide 122A. For example, in certain non-exclusive embodiments, the photoacoustic transducer 154 and/or the guide distal end 122D can have a conical shape, a convex shape, a concave shape, a bulbous shape, a square shape, a stepped shape, a half-circle shape, an ovoid shape, and the like. It is also appreciated that the light guide 122A can further include additional photoacoustic transducers 154 disposed along one or more side surfaces of the length of the light guide 122A.

The light guides 122A described herein can further include one or more diverting features or "diverters" (not shown in FIG. 1) within the light guide 122A that are configured to direct light to exit the light guide 122A toward a side surface e.g., at or near the guide distal end 122D of the light guide 122A, and toward the balloon wall 130. A diverting feature can include any feature of the system herein that diverts light from the light guide 122A away from its axial path toward a side surface of the light guide 122A. Additionally, the light guides 122A can each include one or more light windows disposed along the longitudinal or axial surfaces of each light guide 122A and in optical communication with a diverting feature. Stated in another manner, the diverting features herein can be configured to direct light in the light guide 122A toward a side surface, e.g., at or near the guide distal end 122D, where the side surface is in optical communication with a light window. The light windows can include a portion of the light guide 122A that allows light to exit the light guide 122A from within the light guide 122A, such as a portion of the light guide 122A lacking a cladding material on or about the light guide 122A.

Examples of the diverting features suitable for use herein include a reflecting element, a refracting element, and a fiber diffuser. Additionally, the diverting features suitable for focusing light away from the tip of the light guides 122A herein can include, but are not to be limited to, those having a convex surface, a gradient-index (GRIN) lens, and a mirror focus lens. Upon contact with the diverting feature, the light is diverted within the light guide 122A to the photoacoustic transducer 154 that is in optical communication with a side surface of the light guide 122A. As noted, the photoacoustic transducer 154 then converts light energy into an acoustic wave that extends away from the side surface of the light guide 122A.

The source manifold 136 can be positioned at or near the proximal portion 114 of the catheter system 100. The source manifold 136 can include one or more proximal end openings that can receive the one or more light guides 122A of the light guide bundle 122, the guidewire 112, and/or an inflation conduit 140 that is coupled in fluid communication with the fluid pump 138. The catheter system 100 can also include the fluid pump 138 that is configured to inflate the balloon 104 with the balloon fluid 132, i.e. via the inflation conduit 140, as needed.

As noted above, in the embodiment illustrated in FIG. 1, the system console 123 includes one or more of the light source 124, the power source 125, the system controller 126, the GUI 127, the multiplexer 128, and the multiplexer alignment system 142. Alternatively, the system console 123 can include more components or fewer components than those specifically illustrated in FIG. 1. For example, in certain non-exclusive alternative embodiments, the system console 123 can be designed without the GUI 127. Still alternatively, one or more of the light source 124, the power source 125, the system controller 126, the GUI 127, the multiplexer 128 and the multiplexer alignment system 142 can be provided within the catheter system 100 without the specific need for the system console 123.

Additionally, as shown, the system console 123, and the components included therewith, is operatively coupled to the catheter 102, the light guide bundle 122, and the remainder of the catheter system 100. For example, in some embodiments, as illustrated in FIG. 1, the system console 123 can include a console connection aperture 148 (also sometimes referred to generally as a "socket") by which the light guide bundle 122 is mechanically coupled to the system console 123. In such embodiments, the light guide bundle 122 can include a guide coupling housing 150 (also sometimes referred to generally as a "ferrule") that houses a portion, e.g., the guide proximal end 122P, of each of the light guides 122A. The guide coupling housing 150 is configured to fit and be selectively retained within the console connection aperture 148 to provide the desired mechanical coupling between the light guide bundle 122 and the system console 123.

Further, the light guide bundle 122 can also include a guide bundler 152 (or "shell") that brings each of the individual light guides 122A closer together so that the light guides 122A and/or the light guide bundle 122 can be in a more compact form as it extends with the catheter 102 into the blood vessel 108 during use of the catheter system 100.

As provided herein, the light source 124 can be selectively and/or alternatively coupled in optical communication with each of the light guides 122A, i.e. to the guide proximal end 122P of each of the light guides 122A, in the light guide bundle 122. In particular, the light source 124 is configured to generate light energy in the form of a source beam 124A, e.g., a pulsed source beam, that can be selectively and/or alternatively directed to and received by each of the light guides 122A in the light guide bundle 122 in any desired combination, order, sequence and/or pattern. More specifically, as described in greater detail herein below, the source beam 124A from the light source 124 is directed through the multiplexer 128 such that individual guide beams 124B (or "multiplexed beams") can be selectively and/or alternatively directed into and received by each of the light guides 122A in the light guide bundle 122. In particular, each pulse of the light source 124, i.e. each pulse of the source beam 124A, can be directed through the multiplexer 128 to generate one or more separate guide beams 124B (only one is shown in FIG. 1) that are selectively and/or alternatively directed to one or more of the light guides 122A in the light guide bundle 122.

The light source 124 can have any suitable design. In certain embodiments, as noted above, the light source 124 can be configured to provide sub-millisecond pulses of light from the light source 124 that are focused onto a small spot, i.e. through the use of the multiplexer alignment system 142, in order to couple it into the guide proximal end 122P of the light guide 122A. Such pulses of light energy are then directed along the light guides 122A to a location within the balloon 104, thereby inducing plasma formation in the balloon fluid 132 within the balloon interior 146 of the balloon 104. In particular, the light energy emitted at the guide distal end 122D of the light guide 122A energizes the plasma generator 133 to form the plasma within the balloon fluid 132 within the balloon interior 146. The plasma formation causes rapid bubble formation, and imparts pressure waves upon the treatment site 106. In such embodiments, the sub-millisecond pulses of light from the light source 124 can be delivered to the treatment site 106 at a frequency of between approximately one hertz (Hz) and 5000 Hz. In some embodiments, the sub-millisecond pulses of light from the light source 124 can be delivered to the treatment site 106 at a frequency of between approximately 30 Hz and 1000 Hz. In other embodiments, the sub-millisecond pulses of light from the light source 124 can be delivered to the treatment site 106 at a frequency of between approximately ten Hz and 100 Hz. In yet other embodiments, the sub-millisecond pulses of light from the light source 124 can be delivered to the treatment site 106 at a frequency of between approximately one Hz and 30 Hz. Alternatively, the sub-millisecond pulses of light can be delivered to the treatment site 106 at a frequency that can be greater than 5000 Hz.

It is appreciated that although the light source 124 is typically utilized to provide pulses of light energy, the light source 124 can still be described as providing a single source beam 124A, i.e. a single pulsed source beam.

The light sources 124 suitable for use herein can include various types of light sources including lasers and lamps. Suitable lasers can include short pulse lasers on the sub-millisecond timescale. In some embodiments, the light source 124 can include lasers on the nanosecond (ns) timescale. The lasers can also include short pulse lasers on the picosecond (ps), femtosecond (fs), and microsecond (us) timescales. It is appreciated that there are many combinations of laser wavelengths, pulse widths and energy levels that can be employed to achieve plasma in the balloon fluid 132 of the catheters 102 described herein. In various embodiments, the pulse widths can include those falling within a range including from at least ten ns to 200 ns. In some embodiments, the pulse widths can include those falling within a range including from at least 20 ns to 100 ns. In other embodiments, the pulse widths can include those falling within a range including from at least one ns to 500 ns.

Additionally, exemplary nanosecond lasers can include those within the UV to IR spectrum, spanning wavelengths of about ten nanometers (nm) to one millimeter (mm). In some embodiments, the light sources 124 suitable for use in the catheter systems 100 herein can include those capable of producing light at wavelengths of from at least 750 nm to 2000 nm. In other embodiments, the light sources 124 can include those capable of producing light at wavelengths of from at least 700 nm to 3000 nm. In still other embodiments, the light sources 124 can include those capable of producing light at wavelengths of from at least 100 nm to ten micrometers (μm). Nanosecond lasers can include those having repetition rates of up to 200 kHz. In some embodiments, the laser can include a Q-switched thulium:yttrium-aluminum-garnet (Tm:YAG) laser. In other embodiments, the laser can include a neodymium:yttrium-aluminum-garnet (Nd:YAG) laser, holmium:yttrium-aluminum-garnet (Ho:YAG) laser, erbium:yttrium-aluminum-garnet (Er:YAG) laser, excimer laser, helium-neon laser, carbon dioxide laser, as well as doped, pulsed, fiber lasers.

The catheter systems 100 disclosed herein can generate pressure waves having maximum pressures in the range of at least one megapascal (MPa) to 100 MPa. The maximum pressure generated by a particular catheter system 100 will depend on the light source 124, the absorbing material, the bubble expansion, the propagation medium, the balloon material, and other factors. In some embodiments, the catheter systems 100 herein can generate pressure waves having maximum pressures in the range of at least two MPa to 50 MPa. In other embodiments, the catheter systems 100 herein can generate pressure waves having maximum pressures in the range of at least two MPa to 30 MPa. In yet other embodiments, the catheter systems 100 herein can generate pressure waves having maximum pressures in the range of at least 15 MPa to 25 MPa.

The pressure waves described herein can be imparted upon the treatment site 106 from a distance within a range from at least 0.1 millimeters (mm) to 25 mm extending radially from the light guides 122A when the catheter 102 is placed at the treatment site 106. In some embodiments, the pressure waves can be imparted upon the treatment site 106 from a distance within a range from at least ten mm to 20 mm extending radially from the light guides 122A when the catheter 102 is placed at the treatment site 106. In other embodiments, the pressure waves can be imparted upon the treatment site 106 from a distance within a range from at least one mm to ten mm extending radially from the light guides 122A when the catheter 102 is placed at the treatment site 106. In yet other embodiments, the pressure waves can be imparted upon the treatment site 106 from a distance within a range from at least 1.5 mm to four mm extending radially from the light guides 122A when the catheter 102 is placed at the treatment site 106. In some embodiments, the pressure waves can be imparted upon the treatment site 106 from a range of at least two MPa to 30 MPa at a distance from 0.1 mm to ten mm. In some embodiments, the pressure waves can be imparted upon the treatment site 106 from a range of at least two MPa to 25 MPa at a distance from 0.1 mm to ten mm.

The power source 125 is electrically coupled to and is configured to provide necessary power to each of the light source 124, the system controller 126, the GUI 127, the multiplexer 128, and the multiplexer alignment system 142. The power source 125 can have any suitable design for such purposes.

As noted, the system controller 126 is electrically coupled to and receives power from the power source 125. Additionally, the system controller 126 is coupled to and is configured to control operation of each of the light source 124, the GUI 127, the multiplexer 128 and the multiplexer alignment system 142. The system controller 126 can include one or more processors or circuits for purposes of controlling the operation of at least the light source 124, the GUI 127, the multiplexer 128 and the multiplexer alignment system 142. For example, the system controller 126 can control the light source 124 for generating pulses of light energy as desired, e.g., at any desired firing rate. Additionally, the system controller 126 can control the multiplexer alignment system 142 to map out and accurately ensure the desired optical coupling between the light source 124 and the light guides 122A. Substantially simultaneously and/or subsequently, the system controller 126 can control the multiplexer 128 so that the light energy from the light source 124, i.e. the source beam 124A, can be selectively and/or alternatively directed to each of the light guides 122A, i.e. in the form of individual guide beams 124B, in a desired manner. Additionally, the system controller 126 can further be configured to control operation of other components of the catheter system 100, e.g., the positioning of the catheter 102 adjacent to the treatment site 106, the inflation of the balloon 104 with the balloon fluid 132, etc. Further, or in the alternative, the catheter system 100 can include one or more additional controllers that can be positioned in any suitable manner for purposes of controlling the various operations of the catheter system 100.

The GUI 127 is accessible by the user or operator of the catheter system 100. Additionally, the GUI 127 is electrically connected to the system controller 126. With such design, the GUI 127 can be used by the user or operator to ensure that the catheter system 100 is employed as desired to impart pressure onto and induce fractures into the vascular lesions at the treatment site 106. Additionally, the GUI 127 can provide the user or operator with information that can be used before, during and after use of the catheter system 100. In one embodiment, the GUI 127 can provide static visual data and/or information to the user or operator. In addition, or in the alternative, the GUI 127 can provide dynamic visual data and/or information to the user or operator, such as video data or any other data that changes over time, e.g., during use of the catheter system 100. Further, in various embodiments, the GUI 127 can include one or more colors, different sizes, varying brightness, etc., that may act as alerts to the user or operator. Additionally, or in the alternative, the GUI 127 can provide audio data or information to the user or operator. It is appreciated that the specifics of the GUI 127 can vary depending upon the design requirements of the catheter system 100, or the specific needs, specifications and/or desires of the user or operator.

As provided herein, the multiplexer 128 is configured to selectively and/or alternatively direct light energy from the light source 124 to each of the light guides 122A in the light guide bundle 122. More particularly, the multiplexer 128 is configured to receive light energy from a single light source 124, e.g., a single source beam 124A from a single laser source, and selectively and/or alternatively direct such light energy in the form of individual guide beams 124B to each of the light guides 122A in the light guide bundle 122 in any desired combination, sequence, order and/or pattern. As such, the multiplexer 128 enables a single light source 124 to be channeled simultaneously and/or sequentially through a plurality of light guides 122A such that the catheter system 100 is able to impart pressure onto and induce fractures in vascular lesions at the treatment site 106 within or adjacent to a vessel wall of the blood vessel 108 in a desired manner. Additionally, as shown, the catheter system 100 can include one or more optical elements 147 for purposes of directing the light energy, e.g., the source beam 124A, from the light source 124 to the multiplexer 128.

Additionally, as provided herein, the multiplexer alignment system 142 is configured to ensure that the multiplexer 128 is precisely and accurately aligned so that the individual guide beams 124B are optically coupled onto the guide proximal end 122P of the desired light guide 122A. More specifically, in various embodiments, the multiplexer alignment system 142 provides an effective means to improve optical coupling between the light source 124 and the guide proximal end 122P of each of the light guides 122A within the light guide bundle 122 by measuring coupling efficiency and determining the optimal parameters to trigger firing of the light source 124. As described herein, in some embodiments, the multiplexer alignment system 142 can be configured to operate continuously during coincident use of the multiplexer 128. Additionally, or in the alternative, in other embodiments, the multiplexer alignment system 142 can be configured to actively scan each of the light guides 122A of the light guide bundle 122 to find and map out the X-Y location for each light guide 122A that provides optimal coupling, before the firing of the light source 124 and the operation of the multiplexer 128. In such alternative embodiments, the catheter system 100, e.g., the system controller 126, could be configured to store the information from the multiplexer alignment system 142 and use the mapped out locations for each light guide 122A for real-time firing of the light source 124 and operation of the multiplexer 128.

As described herein, the multiplexer 128 and/or the multiplexer alignment system 142 can have any suitable designs for purposes of precisely, selectively and/or alternatively directing the light energy from the light source 124 to each of the light guides 122A of the light guide bundle 122. Various non-exclusive alternative embodiments of the multiplexer 128 and the multiplexer alignment system 142 are described in detail herein below.

Figure 2:
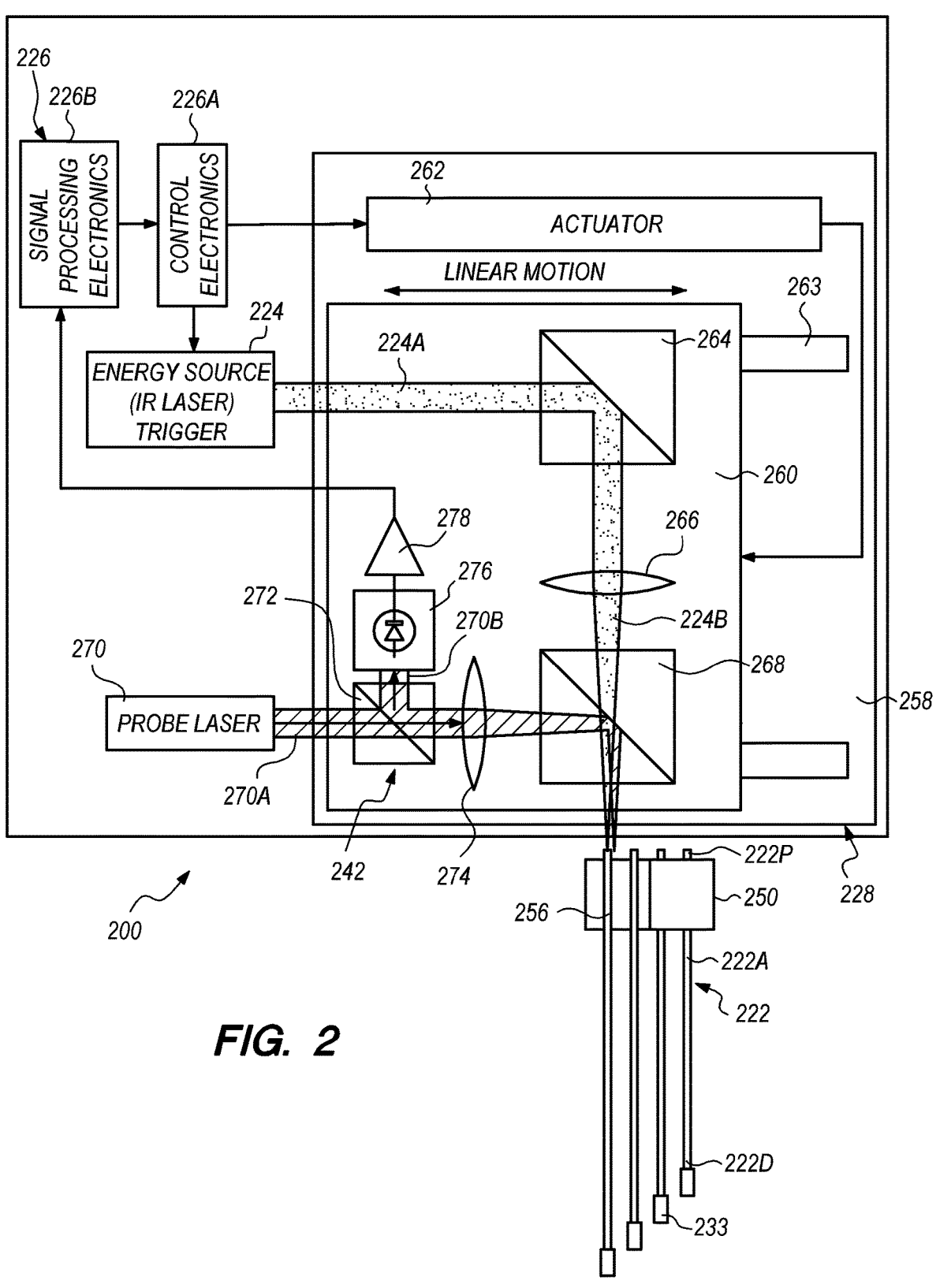
FIG. 2 is a simplified schematic illustration of a portion of an embodiment of the catheter system including an embodiment of the multiplexer and the multiplexer alignment system.

FIG. 2 is a simplified schematic illustration of a portion of an embodiment of the catheter system 200 including an embodiment of the multiplexer 228 and the multiplexer alignment system 242. More particularly, FIG. 2 illustrates a light guide bundle 222 including a plurality of light guides 222A; a light source 224; a system controller 226 including control electronics 226A and signal processing electronics 226B; the multiplexer 228 that receives light energy in the form of a source beam 224A, e.g., a pulsed source beam and/or a semi-continuous wave source beam, from the light source 224 and selectively and/or alternatively directs the light energy in the form of individual guide beams 224B onto a guide proximal end 222P of each of the plurality of the light guides 222A; and the multiplexer alignment system 242 that utilizes light energy from a second light source 270 in the form of a probe source beam 270A to probe a face of the light guide bundle 222 and/or the guide proximal end 222P of each of the light guides 222A in the light guide bundle 222 as a means to improve optical coupling between the guide beams 224B and the guide proximal end 222P of each of the light guides 222A. The light guide bundle 222 and/or the light guides 222A, and the light source 224 are substantially similar in design and function as described in detail herein above. Accordingly, such components will not be described in detail in relation to the embodiment illustrated in FIG. 2. It is further appreciated that certain components of the system console 123 illustrated and described above in relation to FIG. 1, e.g., the power source 125 and the GUI 127, are not illustrated in FIG. 2 for purposes of simplicity and ease of illustration, but would typically be included in many embodiments.

As illustrated, in some embodiments, the control electronics 226A and the signal processing electronics 226B can be included as part of the system controller 226. Alternatively, the control electronics 226A and/or the signal processing electronics 226B can be provided independently of the system controller 226 and can be in electrical communication with the system controller 226.

It is appreciated that the light guide bundle 222 can include any suitable number of light guides 222A, which can be positioned and/or oriented relative to one another in any suitable manner, e.g., to best align the plurality of light guides 222A relative to the multiplexer 228 and/or the multiplexer alignment system 242. For example, in the embodiment illustrated in FIG. 2, the light guide bundle 222 includes four light guides 222A that are aligned in a linear arrangement relative to one another. Alternatively, the light guide bundle 222 can include a different number of light guides 222A, i.e. greater than four or fewer than four light guides 222A, and/or the light guides 222A can be arranged in a different manner relative to one another.

As shown in FIG. 2, each of the light guides 222A includes a plasma generator 233 that is positioned at the guide distal end 222D of the light guide 222A.

Additionally, as illustrated, the guide proximal end 222P of each of the plurality of light guides 222A is retained within a guide coupling housing 250, i.e. within guide coupling slots 256 that are formed into the guide coupling housing 250. In various embodiments, the guide coupling housing 250 is configured to be selectively coupled to the system console 123 (illustrated in FIG. 1) so that the guide coupling slots 256, and thus the light guides 222A, are maintained in a desired fixed position relative to the multiplexer 228 and the multiplexer alignment system 242 during use of the catheter system 200. In some embodiments, the guide coupling slots 256 are provided in the form of V-grooves, such as in a V-groove ferrule block commonly used in multichannel fiber optics communication systems. Alternatively, the guide coupling slots 256 can have another suitable design.

It is appreciated that the guide coupling housing 250 can have any suitable number of guide coupling slots 256, which can be positioned and/or oriented relative to one another in any suitable manner, e.g., to best align the guide coupling slots 256 and thus the light guides 222A relative to the multiplexer 228 and the multiplexer alignment system 242. In the embodiment illustrated in FIG. 2, the guide coupling housing 250 includes four guide coupling slots 256 that are spaced apart in a linear arrangement relative to one another, with precise interval spacing between adjacent guide coupling slots 256. Thus, in such embodiment, the guide coupling housing 250 is capable of retaining the guide proximal end 222P of up to four light guides 222A. Alternatively, the guide coupling housing 250 can have a different number of guide coupling slots 256, i.e. greater than four or fewer than four guide coupling slots 256, and/or the guide coupling slots 256 can be arranged in a different manner relative to one another.

As noted above, the multiplexer 228 is configured to receive light energy in the form of the source beam 224A from the light source 224 and selectively and/or alternatively direct the light energy in the form of individual guide beams 224B onto the guide proximal end 222P of each of the light guides 222A. As such, as shown in FIG. 2, the multiplexer 228 is operatively and/or optically coupled in optical communication to the light guide bundle 222, i.e. to the plurality of light guides 222A.

The design of the multiplexer 228 can be varied depending on the requirements of the catheter system 200, the relative positioning of the light guides 222A, and/or to suit the desires of the user or operator of the catheter system 200. In the embodiment illustrated in FIG. 2, the multiplexer 228 includes one or more of a multiplexer base 258, a multiplexer stage 260, a stage mover 262, a redirector 264, coupling optics 266, and a first beamsplitter 268, which are used in conjunction with the system controller 226, i.e. the control electronics 226A and/or the signal processing electronics 226B, and the multiplexer alignment system 242 as described in detail herein. Alternatively, the multiplexer 228 can include more components or fewer components than those specifically illustrated in FIG. 2.

Additionally, as noted above, the multiplexer alignment system 242 is configured to probe the face of the light guide bundle 222 (i.e. the face of the guide coupling housing 250) and/or the guide proximal end 222P of each of the light guides 222A in the light guide bundle 222 as a means to improve optical coupling between the guide beams 224B and the guide proximal end 222P of each of the light guides 222A.

The design of the multiplexer alignment system 242 can be varied depending on the requirements of the catheter system 200, the relative positioning of the light guides 222A, and/or to suit the desires of the user or operator of the catheter system 200. In the embodiment illustrated in FIG. 2, the multiplexer alignment system 242 includes one or more of the second light source 270, the first beamsplitter 268, a second beamsplitter 272, an optical element 274, a photodetector 276 and an amplifier 278, which are used in conjunction with the system controller 226, i.e. the control electronics 226A and/or the signal processing electronics 226B, and the multiplexer 228. As described in detail herein, the second light source 270 provides light energy in the form of the probe source beam 270A that is directed to scan across the guide proximal end 222P of each of the light guides 222A during a mapping process. As such, as shown in FIG. 2, the multiplexer alignment system 242 and/or the second light source 270 is operatively and/or optically coupled in optical communication to the light guide bundle 222, i.e. to the plurality of light guides 222A. Alternatively, the multiplexer alignment system 242 can include more components or fewer components than those specifically illustrated in FIG. 2.

During use of the catheter system 200, the multiplexer base 258 is fixed in position relative to the light source 224 and the light guides 222A. Additionally, in this embodiment, the multiplexer stage 260 is movably supported on the multiplexer base 258. More particularly, in the embodiment shown in FIG. 2, the stage mover 262 is configured to move the multiplexer stage 260 along a linear path relative to the multiplexer base 258. Further, in certain embodiments, the stage mover 262 can be configured to move the multiplexer stage 260 linearly relative to the multiplexer base 258 along one or more stage guides 263 that are coupled to the multiplexer base 258.

As shown in FIG. 2, the redirector 264, the coupling optics 266 and the first beamsplitter 268 of the multiplexer 228 are mounted on and/or retained by the multiplexer stage 260. Thus, movement of the multiplexer stage 260 relative to the multiplexer base 258 results in corresponding movement of the redirector 264, the coupling optics 266 and the first beamsplitter 268 relative to the fixed multiplexer base 258. Further, with the light guides 222A being fixed in position relative to the multiplexer base 258, movement of the multiplexer stage 260 results in corresponding movement of the redirector 264, the coupling optics 266 and the first beamsplitter 268 relative to the light guides 222A.

Additionally, as shown in FIG. 2, the first beamsplitter 268, the second beamsplitter 272, the optical element 274, the photodetector 276 and the amplifier 278 of the multiplexer alignment system 242 are also mounted on and/or retained by the multiplexer stage 260. Thus, movement of the multiplexer stage 260 relative to the multiplexer base 258 results in corresponding movement of the first beamsplitter 268, the second beamsplitter 272, the optical element 274, the photodetector 276 and the amplifier 278 relative to the fixed multiplexer base 258. Further, with the light guides 222A being fixed in position relative to the multiplexer base 258, movement of the multiplexer stage 260 results in corresponding movement of the first beamsplitter 268, the second beamsplitter 272, the optical element 274, the photodetector 276 and the amplifier 278 relative to the light guides 222A. It is understood that in this, and various other embodiments, the photodetector 276 can include additional focusing or collecting optics.

In various embodiments, in conjunction with use of the multiplexer alignment system 242, the multiplexer 228 is configured to precisely align the coupling optics 266 with each of the light guides 222A such that the source beam 224A generated by the light source 224 can be precisely directed and focused by the multiplexer 228 as a corresponding guide beam 224B onto the guide proximal end 222P of each of the light guides 222A. In its simplest form, as shown in FIG. 2, the multiplexer 228 uses a precision mechanism, i.e. the stage mover 262, to translate the coupling optics 266 along a linear path. This approach requires a single degree of freedom. In certain embodiments, the linear translation mechanism, i.e. the stage mover 262, and/or the multiplexer stage 260 can be electronically controlled to line the beam path of the guide beam 224B sequentially with each individual light guide 222A that is retained, in part, within the guide coupling housing 250 during a scanning process. Alternatively, the stage mover 262 can be equipped with mechanical stops so that the coupling optics 266 can be precisely aligned with the position of each of the light guides 222A.

In this embodiment, the stage mover 262 can have any suitable design for purposes of moving the multiplexer stage 260 in a linear manner relative to the multiplexer base 258. More particularly, the stage mover 262 can be any suitable type of linear translation mechanism.

As noted above, the multiplexer stage 260 is configured to carry the necessary optics, e.g., the redirector 264 and the coupling optics 266, to direct and focus the light energy generated by the light source 224 to each light guide 222A for optimal coupling. With such design, the low divergence of the guide beam 224A over the short distance of motion of the translated multiplexer stage 260 has minimum impact on coupling efficiency to the light guide 222A.

Additionally, in this embodiment, the source beam 224A being directed toward the multiplexer 228 initially impinges on the redirector 264, which is configured to redirect the source beam 224A toward the coupling optics 266. In some embodiments, the redirector 264 redirects the source beam 224A by approximately 90 degrees toward the coupling optics 266. Alternatively, the redirector 264 can redirect the source beam 224A by more than 90 degrees or less than 90 degrees toward the coupling optics 266. Thus, the redirector 264 that is mounted on the multiplexer stage 260 is configured to direct the source beam 224A through the coupling optics 266 so that individual guide beams 224B are focused into the individual light guides 222A in the guide coupling housing 250.

The coupling optics 266 can have any suitable design for purposes of focusing the individual guide beams 224B to each of the light guides 222A. In one embodiment, the coupling optics 266 includes two lenses that are specifically configured to focus the individual guide beams 224B as desired. Alternatively, the coupling optics 266 can have another suitable design.

In certain non-exclusive alternative embodiments, the steering of the source beam 224A so that it is properly directed and focused to each of the light guides 222A can be accomplished using mirrors that are attached to optomechanical scanners, X-Y galvanometers or other multi-axis beam steering devices.

It is appreciated that the operation of aligning the beam path of the guide beam 224B with a selected light guide 222A assumes that the motion axis is perfectly parallel to the axis of the light guide bundle 222 and/or the individual light guides 222A. In some embodiments, a vertical dither can be included to track this axis.

As shown in FIG. 2, the probe source beam 270A from the second energy source 270 is initially directed toward the second beamsplitter 272, from where at least a portion of the probe source beam 270A is directed onward toward the optical element 274. Further, as shown in the embodiment illustrated in FIG. 2, the multiplexer alignment system 242, in conjunction with the multiplexer 228, is configured to precisely align the optical element 274, e.g., a coupling lens, relative to each of the light guides 222A such that the probe source beam 270A generated by the second light source 270 can be precisely directed and focused by the multiplexer alignment system 242 to scan across the face of the guide coupling housing 250 and/or the guide proximal end 222P of each of the light guides 222A.

Additionally, as illustrated, each of the individual guide beams 224B and the probe source beam 270A are all directed to impinge on the first beamsplitter 268 prior to being directed toward the light guides 222A. Stated in another manner, in this embodiment, the first beamsplitter 268 is positioned in the optical path of the individual guide beams 224B between the coupling optics and the light guides 222A, and the first beamsplitter 268 is also positioned in the optical path of the probe source beam 270A between the optical element 274 and the light guides 222A. In certain embodiments, the first beamsplitter 268 can be a dichroic beamsplitter that is configured to transmit light having wavelengths longer than a predetermined cutoff wavelength, and reflect (and redirect, e.g., by approximately 90 degrees or another suitable amount) light having wavelengths shorter than the predetermined cutoff wavelength. For example, in some embodiments, the light source 224 can be a pulsed infrared laser source such that the individual guide beams 224B have a wavelength in the infrared light range; and the second light source 270 can be a low-power, visible light continuous wave laser source such that the probe source beam 270A has a wavelength in the visible light range. In such embodiments, the first beamsplitter 268 can have a predetermined cutoff wavelength such that the individual guide beams 224B will be transmitted through the first beamsplitter 268 toward the light guides 222A, while the probe source beam 270A will be reflected by the first beamsplitter 268 and redirected toward the light guides 222A. Thus, as shown, the first beamsplitter 268 allows the path of the probe source beam 270A to be effectively combined with the path of the individual guide beams 224B. Alternatively, the first beamsplitter 268 and/or the light source 224 and the second light source 270 can have another suitable design.

Additionally, or in the alternative, in one embodiment, the second light source 270 can include and/or incorporate high-speed modulation in order to allow phase-sensitive (lock-in) detection. In such embodiment, it is appreciated that the modulation must be much faster than dwell time on target as the probe source beam 270A from the second light source 270 scans across the face of the guide coupling housing 250 and/or the guide proximal end 222P of each of the light guides 222A.

During operation of the catheter system 200, the control electronics 226A drive the stage mover 262 to move the multiplexer stage 260 in a desired manner so that the probe source beam 270A and the individual guide beams 224B scan across the face of the guide coupling housing 250 and/or the guide proximal end 222P of each of the light guides 222A. Additionally, the optical element 274 of the multiplexer alignment system 242 is used to focus the probe source beam 270A down to form a spot that will couple to the guide proximal end 222P of each light guide 222A similarly to the individual guide beams 224B as directed and focused by the redirector 264 and the coupling optics 266 of the multiplexer 228. In some embodiments, the design and focal length of the optical element 274 may be configured to create a spot size for the probe source beam 270A that is larger than the spot size for the individual guide beams 224B. This can be used to cover more of the guide proximal end 222P of each light guide 222 as the scanning occurs.

In certain embodiments, as shown in FIG. 2, the catheter system 200 is controlled such that the probe source beam 270A is slightly offset from the individual guide beams 224B as they are scanned across the face of the guide coupling housing 250. More particularly, in such embodiments, the optical element 274 and the coupling optics 266 can be configured and/or positioned such that the probe source beam 270A slightly leads or is slightly ahead of the individual guide beams 224B during the scanning process. Stated in another manner, the coupling optics 266 in the multiplexer 228 and the optical element 274 of the multiplexer alignment system 242 are aligned such that the spot from the guide beam 224B is formed a controlled distance lagging the spot from the probe source beam 270A.

Additionally, during operation, the second light source 270 is configured to operate continuously as the multiplexer 228 and the multiplexer alignment system 242 scan across the face of the guide coupling housing 250. In particular, the spot from the probe source beam 270A of the second light source 270 is focused by the optical element 274 onto the end face of the guide coupling housing 250 and the faces of the individual light guides 222A during the scanning process. During the scanning process, at least a portion of the light in the focused spot from the probe source beam 270A scatters off the faces of the guide coupling housing 250 and the individual light guides 222A, and is directed back toward the first beamsplitter 268 as a backscattered energy beam 270B. The backscattered energy beam 270B is reflected off of and redirected by the first beamsplitter 268 toward the optical element 274 where it is collected and collimated. Thus, the optical element 274 acts to both form a spot from the second energy source 270 as it is focused toward and onto the guide coupling housing 250, and to collect the light scattered from the probe source beam 270A impinging on the guide coupling housing 250 and/or the faces of the light guides 222A, i.e. the backscattered energy beam 270B, and collimate such light.

Further, or in the alternative, in certain embodiments, the guide proximal end 222P of each of the light guides 222A can be coated with an anti-reflective coating at the wavelength of the guide beams 224B and a highly-reflective coating at the wavelength of the probe source beam 270A. With such design, the degree of backscatter for the probe source beam 270A, i.e. to provide the backscattered energy beam 270B, can be improved.

The optical element 274 then focuses the backscattered energy beam 270B back toward the second beamsplitter 272. More specifically, as shown, the second beamsplitter 272 is not only positioned in the optical path of the probe source beam 270A from the second light source 270, but the second beamsplitter 272 is also positioned in the optical path of the backscattered energy beam 270B between the optical element 274 and the photodetector 276. In one embodiment, the second beamsplitter 272 can be a 10/90 beamsplitter that is configured to transmit ten percent of the incident beam and redirect or reflect 90 percent of the incident beam. This allows a small percentage of the incident light from the backscattered energy beam 270B to pass through and reflects most of the light returned as the backscattered energy beam 270B onto the photodetector 276. Thus, the optical element 274 effectively couples at least a portion of the light energy scattered from the faces of the guide coupling housing 250 and the individual light guides 222A, i.e. in the form of the backscattered energy beam 270B, onto the photodetector 276. With such design, a significant portion of the visible light scattered from the faces of the guide coupling housing 250 and the individual light guides 222A is collected by the photodetector 276. It is appreciated that the small percentage of transmitted light back through the second beam splitter 272 is easily compensated for by increasing the power of the second energy source 270. This technique increases the signal-to-noise ratio (SNR) of the detection system. Alternatively, the second beamsplitter 272 can have another suitable design. For example, in certain non-exclusive alternative embodiments, the second beamsplitter 272 can be a 1/99 beamsplitter, a 5/95 beamsplitter, a 20/80 beamsplitter, a 30/70 beamsplitter, a 40/60 beamsplitter, a 50/50 beamsplitter, a 60/40 beamsplitter, a 70/30 beamsplitter, an 80/20 beamsplitter, a 90/10 beamsplitter, a 95/5 beamsplitter, a 99/1 beamsplitter, or another suitable design.

Additionally, in some embodiments, the photodetector 276 then generates a signal that is based on the portion of the visible light scattered from the faces of the guide coupling housing 250 and the individual light guides 222A, i.e. the portion of the backscattered energy beam 270B, which has been collected by the photodetector 276. As shown in FIG. 2, the signal from the photodetector 276 is then directed toward the amplifier 278 where the signal from the photodetector 276 is amplified. The amplified signal is thus utilized, e.g., within the signal processing electronics 226B, to determine the intensity of the backscattered energy beam 270B.

As described herein, the design of the second beamsplitter 272 should be such that at least a sufficient portion of the backscattered energy beam 270B needs to be directed onto the photodetector 276 to generate a strong enough signal to be effectively evaluated by the signal processing electronics 226B.

Additionally, it is appreciated that the photodetector 276 can have any suitable design for purposes of effectively collecting the portion of the visible light, i.e. the backscattered beam 270B, scattered from the faces of the guide coupling housing 250 and the individual light guides 222A. For example, in one non-exclusive embodiment, the photodetector 276 can include a narrow band spectral filter that is configured to match the wavelength of the probe source beam 270A from the second light source 270 so as to reduce background noise.

As the probe source beam 270A scans across the face of the guide coupling housing 250, the local reflectance creates strong backscatter and, thus, a large signal. For example, when the spot from the probe source beam 270A is far away from the guide proximal end 222P of the light guides 222A, the amount of backscatter, and thus the corresponding signal, will be high. As the spot from the probe source beam 270A comes into alignment with the guide proximal end 222P and thus the fiber core, more light will be coupled into the light guide and the backscatter signal will decrease. When the signal reaches a relative minimum, it is an indication of precise optimal coupling. Stated in another manner, as described herein, when the intensity of the backscattered energy beam 270B is determined to be at a local minimum, i.e. by the signal processing electronics 226B, then it is determined that it is an appropriate time to fire the light source 224 so that a guide beam 224B is precisely directed and coupled onto the guide proximal end 222P of the desired light guide 222A. The signal processing electronics 226B and the control electronics 226A monitor and keep track of this information.

More particularly, with the system controller 226 and/or the control electronics 226A controlling the speed of the scanning process, and with the offset between the probe source beam 270A and the individual guide beams 224B being known, the time between the optimal alignment for coupling the probe source beam 270A and time when the individual guide beams 224B will be at that location can be determined exactly. This allows the catheter system 200 to fully scan the face of the guide coupling housing 250 and/or the guide proximal end 222P of each of the light guides 222A to determine the location of optimal coupling and leave time to correctly position the spot and fire the light source 224 accordingly. It is appreciated that this general concept can be applied for having the light source 224 fire and have the individual guide beams 224B be precisely coupled onto the guide proximal end 222P of each of the light guides 222A in any suitable combination, order and/or pattern. This general concept is illustrated in FIGS. 3A through 3D.

In particular, FIGS. 3A-3D are a schematic illustration representative of a timing scheme as the multiplexer and the multiplexer alignment system are scanning relative to the plurality of light guides, and a graphical representation of backscattered beam intensity as a function of scan position which is used to determine proper timing for firing of the light source. As shown, four light guides 322A are organized into a linear array by a guide coupling housing 350. The location of a probe spot 380P from the probe source beam is shown along with the projected location of a guide spot 380G from the individual guide beam from the pulsed light source when it is fired. In particular, in FIG. 3A, the probe spot 380P from the probe source beam is initially approaching the guide proximal end 322P of the third light guide 322A (labeled with the number "3"). As shown, the projected guide spot 380G for the guide beam is also shown as slightly lagging the probe spot 380P from the probe source beam in the scanning direction. Additionally, the graph to the right of the diagram shows the intensity signal of measured backscatter as a function of the position of the multiplexer. The multiplexer alignment system determines optimal coupling efficiency by identifying the local minimum in the curve.

Figures 3A, 3B:
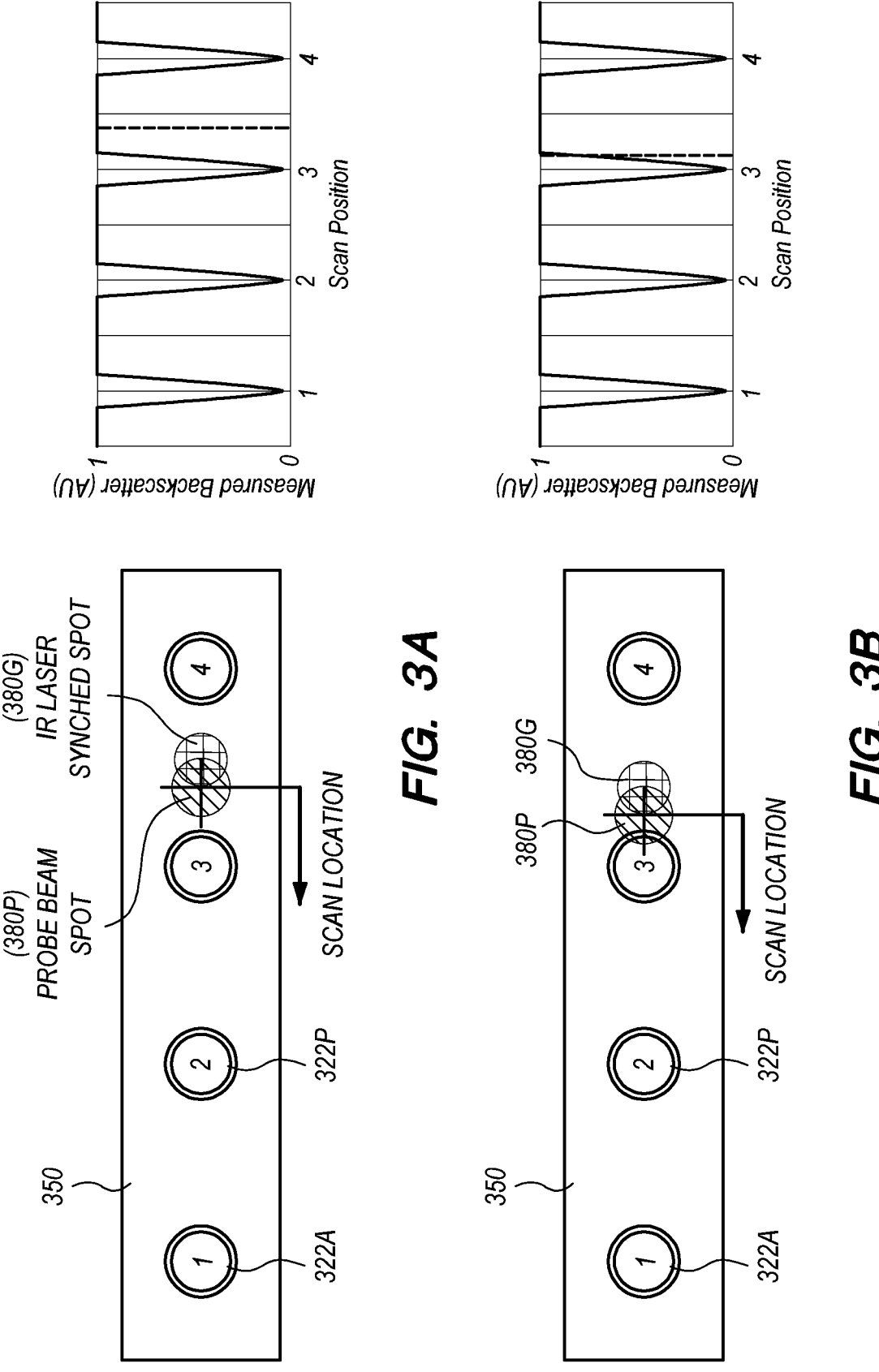
FIGS. 3A-3D are a schematic illustration representative of a timing scheme as the multiplexer and the multiplexer alignment system are scanning relative to the plurality of light guides, and a graphical representation of backscattered beam intensity as a function of scan position which is used to determine proper timing for firing of the first light source.
Figures 3C, 3D:
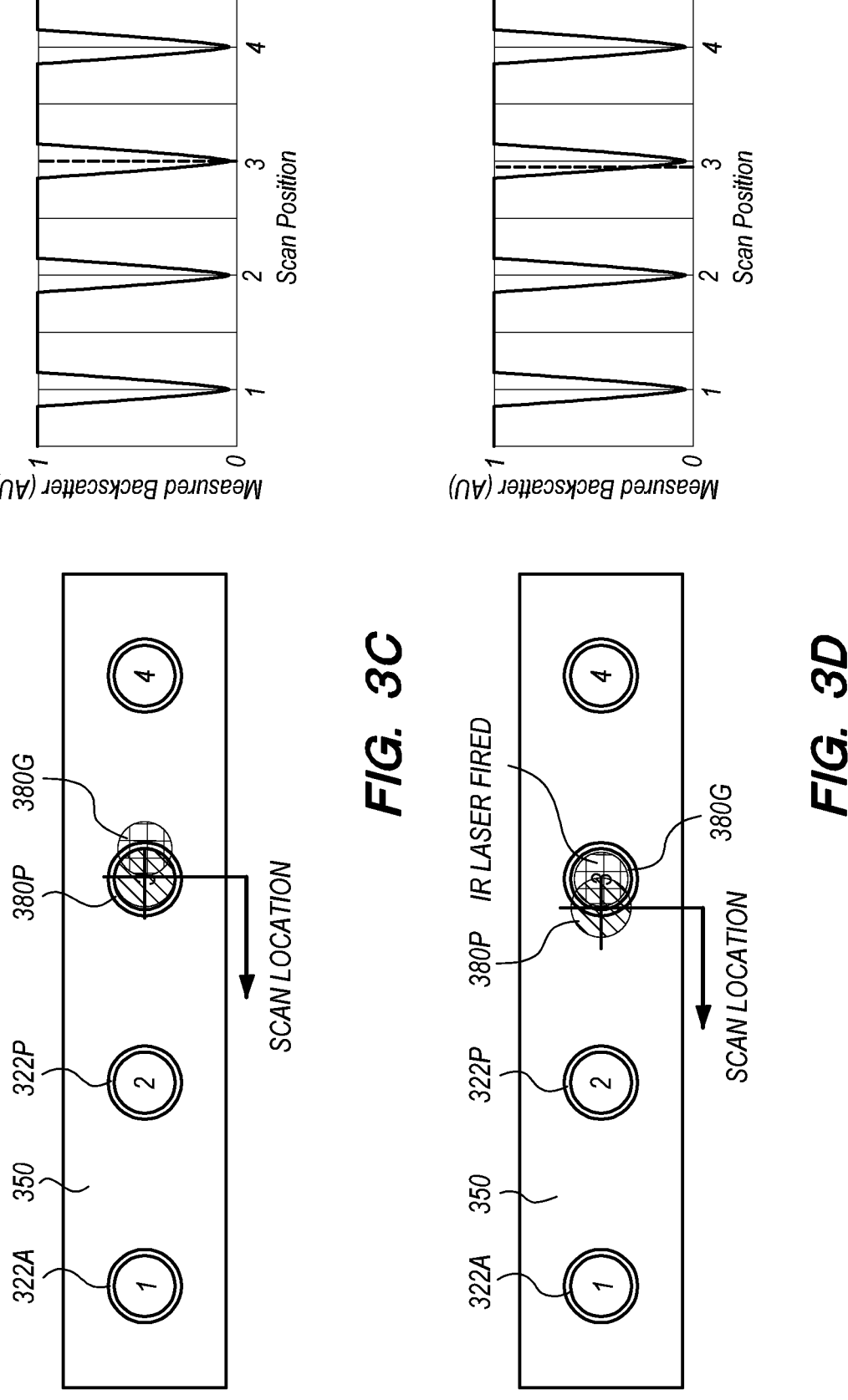

Next, in FIG. 3B, the probe spot 380P from the probe source beam is first starting to impinge on the guide proximal end 322P of the third light guide 322A, with the projected guide spot 380G from the guide beam again slightly lagging behind along the scanning direction. Then, in FIG. 3C, the probe spot 380P from the probe source beam is precisely impinging on the guide proximal end 322P of the third light guide 322A. As shown in the graph to the right, at such point the intensity signal is shown at a local minimum along the curve. Once the probe spot 380P from the probe source beam has passed this location and the guide spot from the primary beam comes into location, the light source is fired. Thus, based on the known offset between the probe source beam and the guide beam, and the known speed of the scan, it is understood that at this point it is the appropriate time to fire the light source so that the guide beam will be precisely coupled into the guide proximal end of the third light guide. Refinement of the timing of this process can achieve exact tuning for other characteristics of the laser pulse timing and characteristics and multiplexer dynamics. Such timing is shown in FIG. 3D.

Returning now to FIG. 2, although FIG. 2 illustrates that the light guides 222A are fixed in position relative to the multiplexer base 258, in some alternative embodiments, it is appreciated that the light guides 222A can be configured to move relative to the coupling optics 266 and the optical element 274 that are fixed in position. In such embodiments, the guide coupling housing 250 itself would move, e.g., the guide coupling housing 250 can be carried by a linear translation stage. The multiplexer alignment system 242 would need to monitor the position of this stage and determine parametric motion for the projected guide spot from the light source 224 while scanning and determining location for optimal coupling. The system controls the stage and steps it to align a light guide 222A with the guide beam 224B and coupling optics 266 when the determined position for optimal coupling was reached. While such an embodiment can be effective, it is further appreciated that additional protection and controls would be required to make it safe and reliable as the guide coupling housing 250 moves relative to the coupling optics 266 of the multiplexer 228 during use.

Still alternatively, in another embodiment, the scanning process for each of the multiplexer alignment system 242 and the multiplexer 228 can be conducted independently from one another. In particular, in one non-exclusive alternative embodiment, the catheter system 200 can be configured such that the multiplexer alignment system 242 conducts a full scanning and mapping of the faces of the guide coupling housing 250 and/or the guide proximal ends 222P of each of the light guides 222A, without the multiplexer 228 scanning as well substantially simultaneously. Thus, in such embodiment, the multiplexer alignment system 242 would scan through every light guide 222A and find the X-Y location for each light guide 222A that gives optimal coupling, and do this without firing the main light source 224. It could go slowly and do a thorough X-Y scan across the face of the guide coupling housing 250 and map the whole thing out. Such information would then be stored in the control electronics, with such information on locations being subsequently used for real-time firing of the primary light source 224. In this embodiment, the multiplexer alignment system 242 could still utilize the second light source 270 such as shown in FIG. 2. Alternatively, the multiplexer alignment system 242 could also be configured to use the same light source 224 as is being used and manipulated by the multiplexer 228.

Figure 4:
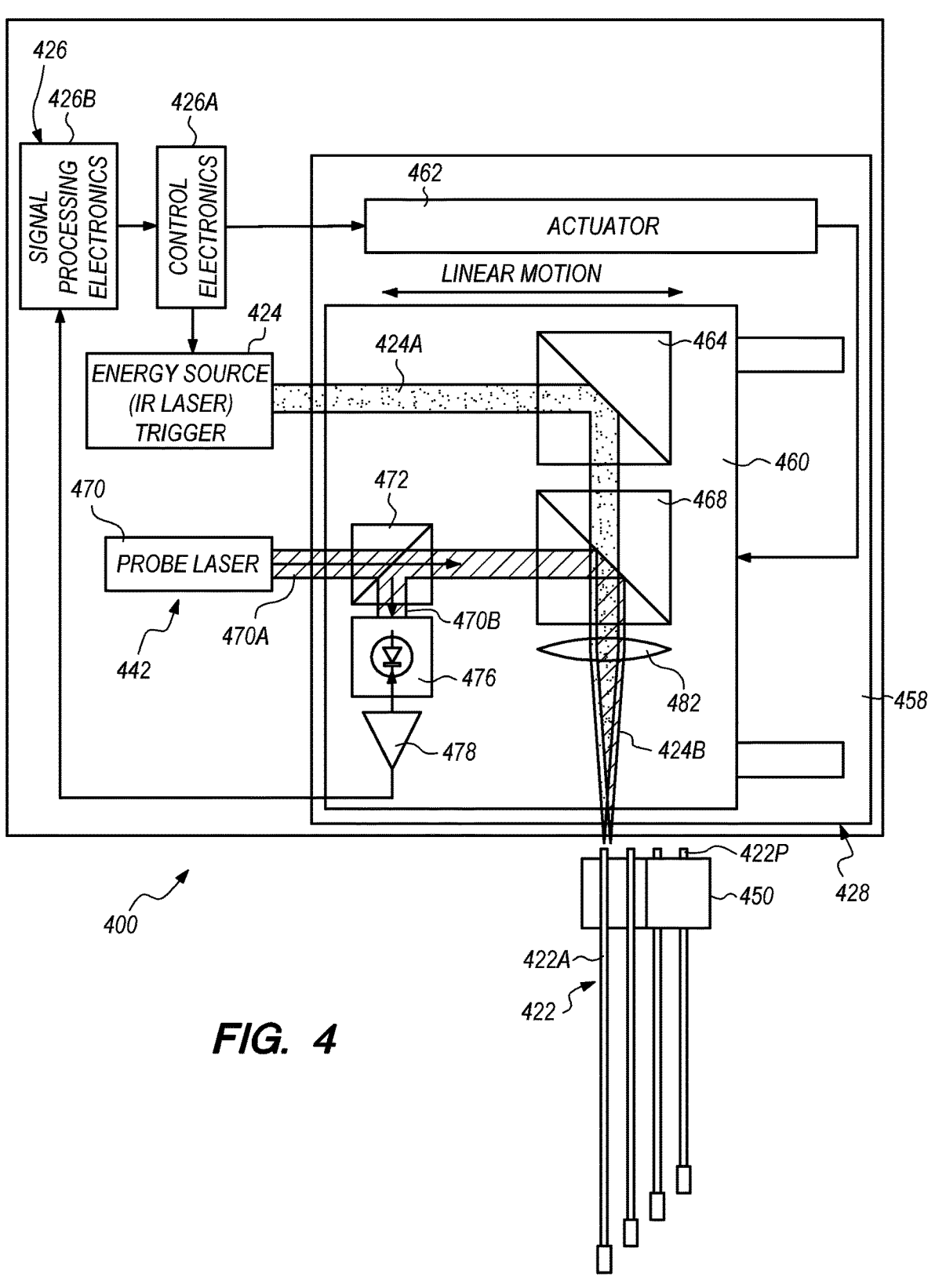
FIG. 4 is a simplified schematic illustration of a portion of another embodiment of the catheter system including another embodiment of the multiplexer and the multiplexer alignment system.

FIG. 4 is a simplified schematic illustration of a portion of another embodiment of the catheter system 400 including another embodiment of the multiplexer 428 and the multiplexer alignment system 442. As illustrated, the embodiment of the catheter system 400 illustrated in FIG. 7, including the multiplexer 428 and the multiplexer alignment system 442, is substantially similar in design and function to the catheter system 200 as illustrated and described in relation to FIG. 2. For example, as shown, the catheter system 400 again includes a light guide bundle 422 including a plurality of light guides 422A retained within a guide coupling housing 450; a light source 424 that generates a source beam 424A; a system controller 426 including control electronics 426A and signal processing electronics 426B; the multiplexer 428 and the multiplexer alignment system 442.

It is appreciated that the light guide bundle 422 can include any suitable number of light guides 422A, which can be positioned and/or oriented relative to one another in any suitable manner, e.g., to best align the plurality of light guides 422A relative to the multiplexer 428 and the multiplexer alignment system 442. For example, in the embodiment illustrated in FIG. 4, the light guide bundle 422 again includes four light guides 422A that are aligned in a generally linear arrangement relative to one another, with the guide proximal end 422P of each of the light guides 422A being retained within the guide coupling housing 450. The light guide bundle 422 and/or the light guides 422A are substantially similar in design and function as described in detail herein above. Accordingly, such components will not be described in detail in relation to the embodiment illustrated in FIG. 4.

As noted, the multiplexer 428 and the multiplexer alignment system 442 are substantially similar in design and function to what was described in detail herein above in relation to FIG. 2. In particular, the multiplexer 428 again includes one or more of a multiplexer base 458, a multiplexer stage 460, a stage mover 462, a redirector 464, and a first beamsplitter 468, which are used in conjunction with the system controller 426, i.e. the control electronics 426A and/or the signal processing electronics 426B, and the multiplexer alignment system 442. Additionally, the multiplexer alignment system 442 again includes one or more of a second light source 470 that generates a probe source beam 470A, the first beamsplitter 468, a second beamsplitter 472, a photodetector 476 and an amplifier 478, which are used in conjunction with the system controller 426, i.e. the control electronics 426A and/or the signal processing electronics 426B, and the multiplexer 428.

However, in this embodiment, the relative positioning of certain components of the multiplexer 428 and/or the multiplexer alignment system 442 have been modified from the previous embodiment. Additionally, as shown, the coupling optics 266 of the multiplexer 228 and the optical element 274 of the multiplexer alignment system 242 have been replaced by coupling optics 482, which are configured to be included within and used by both the multiplexer 428 and the multiplexer alignment system 442.

More specifically, as illustrated, each of the source beam 424A and the probe source beam 470A are directed toward and impinge upon the first beamsplitter 468 before being directed toward the coupling optics 482. As shown in FIG. 4, the source beam 424A is transmitted through the first beamsplitter 468, e.g., a dichroic beamsplitter, as individual guide beams 424B that are directed through the coupling optics 482 to be directed and focused to scan across the face of the guide coupling housing 450 and/or the guide proximal end 422P of each of the light guides 422A. Similarly, as shown, the probe source beam 470A is redirected by the first beamsplitter 468 so that the probe source beam 470A is also directed through the coupling optics 482 to be directed and focused to scan across the face of the guide coupling housing 450 and/or the guide proximal end 422P of each of the light guides 422A. With such design, i.e. with use of coupling optics 482 that is used for both the multiplexer 428 and the multiplexer alignment system 442, the overall design can have a simplified and more compact layout. The guide beams 424B and the probe source beam 470A are focused down after the coupling optics 482 thereby improving damage threshold for the coupling optics 482. Additionally, such design also moves the focal part of the guide beams 424B and the probe source beam 470A further out from the multiplexer stage 460 which eases the configuration for the connection of the guide coupling housing 450 to the system console 123 (illustrated in FIG. 1).

Similar to the previous embodiment, during the scanning process, at least a portion of the light in the focused spot from the probe source beam 470A scatters off the faces of the guide coupling housing 450 and the individual light guides 422A, and is directed back toward the coupling optics 482 and the first beamsplitter 468 as a backscattered energy beam 470B. After being focused and collimated by the coupling optics 482, the backscattered energy beam 470B is reflected off of and redirected by the first beamsplitter 468 toward the second beamsplitter 472, e.g., a 10/90 beamsplitter or another suitable type of beamsplitter (i.e. with different levels of transmittance and reflectance of the incident beam). The second beamsplitter 472 subsequently reflects a portion, e.g., most, of the light returned as the backscattered energy beam 470B onto the photodetector 476.

Additionally, in some embodiments, the photodetector 476 then generates a signal that is based on the portion of the visible light scattered from the faces of the guide coupling housing 450 and the individual light guides 422A, i.e. the portion of the backscattered energy beam 470B, which has been collected by the photodetector 476. As shown in FIG. 4, the signal from the photodetector 476 is then directed toward the amplifier 478 where the signal from the photodetector 476 is amplified. The amplified signal is thus utilized, e.g., within the signal processing electronics 426B, to determine the intensity of the backscattered energy beam 470B. It is understood that in this, and various other embodiments, the photodetector 476 can include additional focusing or collecting optics.

Further, as with the previous embodiment, when the intensity of the backscattered energy beam 470B is determined to be at a local minimum, i.e. by the signal processing electronics 426B, then it is determined that it is an appropriate time to fire the light source 424 so that a guide beam 424B is precisely directed and coupled onto the guide proximal end 422P of the desired light guide 422A. The signal processing electronics 426B and the control electronics 426A monitor and keep track of this information. More particularly, with the system controller 426 and/or the control electronics 426A controlling the speed of the scanning process, and with the offset between the probe source beam 470A and the individual guide beams 424B being known, the time between the optimal alignment for coupling the probe source beam 470A and time when the individual guide beams 424B will be at that location can be determined exactly. This allows the catheter system 400 to fully scan the face of the guide coupling housing 450 and/or the guide proximal end 422P of each of the light guides 422A to determine the location of optimal coupling and leave time to correctly position the spot and fire the light source 424 accordingly. It is appreciated that this general concept can be applied for having the light source 424 fire and have the individual guide beams 424B be precisely coupled onto the guide proximal end 422P of each of the light guides 422A in any suitable combination, order and/or pattern.

Moreover, although FIG. 4 illustrates that the light guides 422A are fixed in position relative to the multiplexer base 458, in some alternative embodiments, it is appreciated that the light guides 422A can be configured to move relative to the coupling optics 482 that are fixed in position. In such embodiments, the guide coupling housing 450 itself would move, e.g., the guide coupling housing 450 can be carried by a linear translation stage. The multiplexer alignment system 442 would need to monitor the position of this stage and determine parametric motion for the projected guide spot from the light source 424 while scanning and determining location for optimal coupling. The system controls the stage and steps it to align a light guide 422A with the guide beam 424B and coupling optics 482 when the determined position for optimal coupling was reached.

Figure 5:
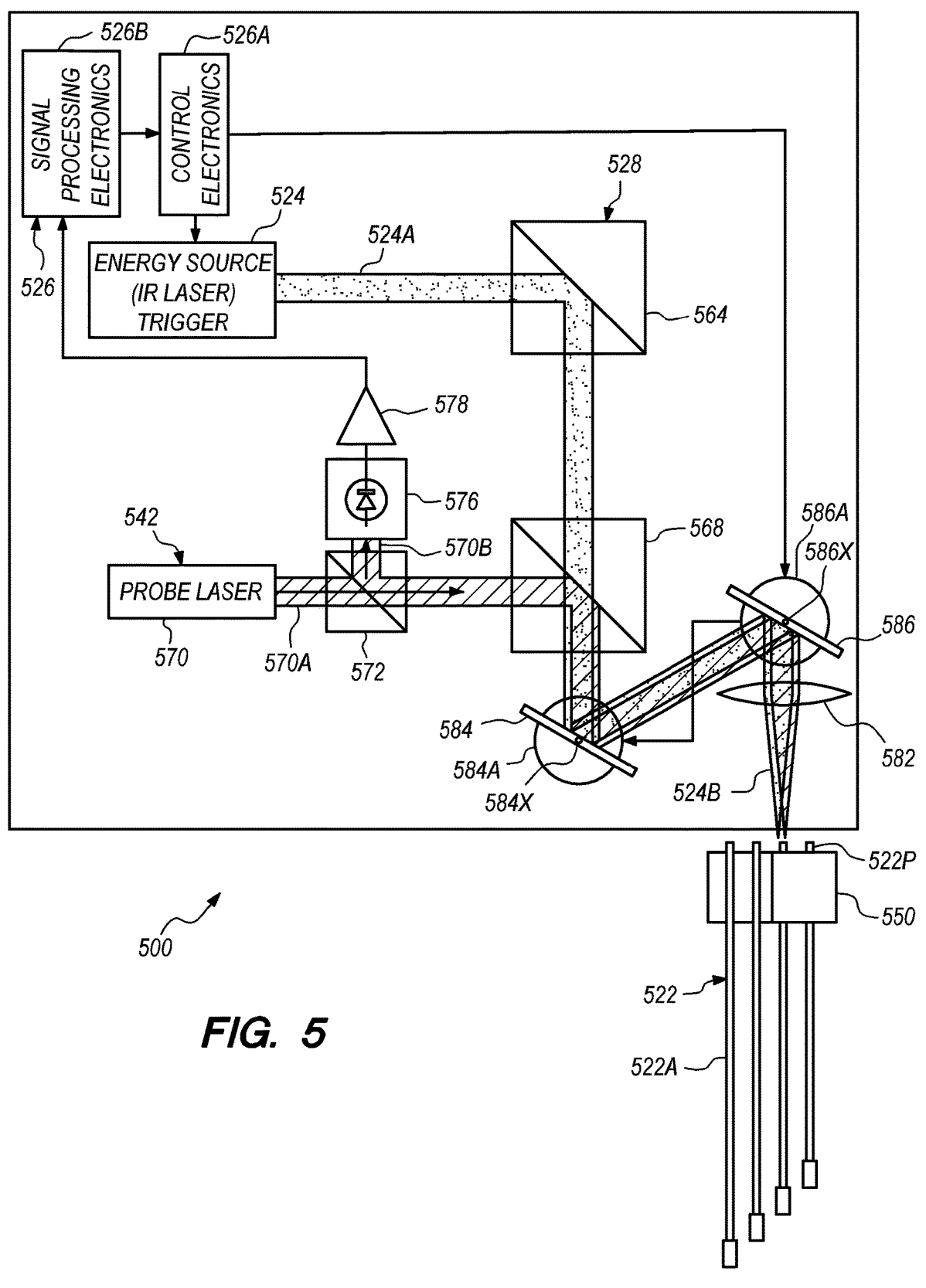
FIG. 5 is a simplified schematic illustration of a portion of still another embodiment of the catheter system including still another embodiment of the multiplexer and the multiplexer alignment system.

FIG. 5 is a simplified schematic illustration of a portion of still another embodiment of the catheter system 500 including still another embodiment of the multiplexer 528 and the multiplexer alignment system 542. In particular, as shown in FIG. 5, the catheter system 500 can include one or more of a light guide bundle 522 including a plurality of light guides 522A retained within a guide coupling housing 550; a light source 524 that generates a source beam 524A; a system controller 526 including control electronics 526A and signal processing electronics 526B; the multiplexer 528 and the multiplexer alignment system 542.

It is appreciated that the light guide bundle 522 can include any suitable number of light guides 522A, which can be positioned and/or oriented relative to one another in any suitable manner, e.g., to best align the plurality of light guides 522A relative to the multiplexer 528 and the multiplexer alignment system 542. For example, in the embodiment illustrated in FIG. 5, the light guide bundle 522 again includes four light guides 522A that are aligned in a generally linear arrangement relative to one another, with the guide proximal end 522P of each of the light guides 522A being retained within the guide coupling housing 550. The light guide bundle 522 and/or the light guides 522A are substantially similar in design and function as described in detail herein above. Accordingly, such components will not be described in detail in relation to the embodiment illustrated in FIG. 5.

As with the previous embodiments, the multiplexer 528 is configured to receive light energy in the form of the source beam 524A, e.g., a pulsed source beam, from the light source 524 and direct the light energy in the form of individual guide beams 524B onto the guide proximal end 522P of each of the plurality of the light guides 522A in any desired combination, order, sequence and/or pattern.

The design of the multiplexer 528 can be varied depending on the requirements of the catheter system 500, the relative positioning of the light guides 522A, and/or to suit the desires of the user or operator of the catheter system 500. In the embodiment illustrated in FIG. 5, the multiplexer 528 includes one or more of a (fixed) redirector 564, a first beamsplitter 568, a first movable redirector 584, a second movable redirector 586, and coupling optics 582, which are used in conjunction with the system controller 526, i.e. the control electronics 526A and/or the signal processing electronics 526B, and the multiplexer alignment system 542 as described in detail herein. Alternatively, the multiplexer 528 can include more components or fewer components than those specifically illustrated in FIG. 5.

Additionally, as with the previous embodiments, the multiplexer alignment system 542 is configured to probe the face of the light guide bundle 522 (i.e. the face of the guide coupling housing 550) and/or the guide proximal end 522P of each of the light guides 522A in the light guide bundle 522 as a means to improve optical coupling between the guide beams 524B and the guide proximal end 522P of each of the light guides 522A.

The design of the multiplexer alignment system 542 can be varied depending on the requirements of the catheter system 500, the relative positioning of the light guides 522A, and/or to suit the desires of the user or operator of the catheter system 500. In the embodiment illustrated in FIG. 5, the multiplexer alignment system 542 includes one or more of the second light source 570, the first beamsplitter 568, a second beamsplitter 572, the first movable redirector 584, the second movable redirector 586, the coupling optics 582, a photodetector 576 and an amplifier 578, which are used in conjunction with the system controller 526, i.e. the control electronics 526A and/or the signal processing electronics 526B, and the multiplexer 528. As described in detail herein, the second light source 570 provides light energy in the form of the probe source beam 570A that is directed to scan across the guide proximal end 522P of each of the light guides 522A during a mapping process. Alternatively, the multiplexer alignment system 542 can include more components or fewer components than those specifically illustrated in FIG. 5.

As above, in various embodiments, the multiplexer 528 and the multiplexer alignment system 542 are configured to operate substantially simultaneously, with the probe source beam 570A from the second light source 570 slightly leading the guide beams 524B from the light source 524, as both the probe source beam 570A and the individual guide beams 524B are scanning across the face of the guide coupling housing 550. Alternatively, in other embodiments, the multiplexer alignment system 542 can be configured to fully map out the face of the guide coupling housing 550 with the probe source beam 570A from the second light source 570 prior to any use of the light source 524 and the multiplexer 528 that are configured to direct and focus individual guide beams 524B onto the guide proximal end 522P of each of the light guides 522A in any desired sequence, order or pattern. The general operation of each of the multiplexer 528 and the multiplexer alignment system 542 in the embodiments shown in FIG. 5 will now be described in greater detail.

During use of the multiplexer 528, the source beam 524A from the light source 524 is initially directed toward and impinges on the redirector 564, which is configured to redirect the source beam 524A, e.g., by approximately 90 degrees or another suitable amount, toward the first beamsplitter 568, e.g., a dichroic beamsplitter. Subsequently, based on the design of the first beamsplitter 568, the source beam 524A is transmitted through the first beamsplitter 568 and toward the first movable redirector 584. As shown, the first movable redirector 584 is configured to redirect the source beam 524A toward the second movable redirector 586. In this embodiment, the first movable redirector 584 is selectively rotatable about a rotational axis 584X, i.e. by a first redirector mover 584A, to adjust the angle of the source beam 524A as the source beam 524A is directed toward the second movable redirector 586. The source beam 524A is then redirected by the second movable redirector 586 and directed toward the coupling optics 582 as a guide beam 524B that will be coupled by the coupling optics 582 onto the guide proximal end 522P of each light guide 522A as desired. In this embodiment, the second movable redirector 586 is selectively rotatable about a rotational axis 586X, i.e. by a second redirector mover 586A, to adjust the angle of the guide beam 524B as the guide beam 524B is directed toward the coupling optics 582. As used herein, the coupling optics 582 can alternatively include a simple lens, a compound lends or an f-theta lens.

It is appreciated that the first movable redirector 584 and the second movable redirector 586, and the corresponding redirector movers 584A, 586A, can have any suitable design for purposes of redirecting the source beam 524A and/or the guide beams 524B in a desired manner. For example, in one embodiment, each of the first movable redirector 584 and the second movable redirector 586 can be provided in the form of a galvanometer, i.e. a galvanometer mirror scanner, that includes a mirror (or other reflective surface) that is rotated about the rotational axis 584X, 586X using the redirector mover 584A, 586A, respectively. Alternatively, the movable redirectors 584, 586, can include one or more multi-axis scanners. The movers 584A, 586A are utilized to rotate the movable redirectors 584, 586, respectively, in order to steer the guide beam 524B into the coupling optics 582, i.e. at a desired incident angle, so that the guide beam 524B can be selectively focused by the coupling optics 582 onto any of the light guides 522A within the light guide bundle 522. In particular, as the movable redirectors 584, 586 are rotated, the movable redirectors 584, 586 steer the guide beam 524B into the coupling optics 582, e.g., a focusing lens, at different angles. This results in scanning of the guide beam 524B in a linear manner, translating the focal point into different light guides 522A mounted within the light guide bundle 522. Thus, by changing the angle of the movable redirectors 584, 586, the guide beam 524B can be selectively steered onto the guide proximal end 522P of any of the light guides 522A in the light guide bundle 522. In non-exclusive alternative embodiments, the movable redirectors 584, 586 can include mirrors attached to optomechanical scanners, galvanometers or other multi-axis beam steering devices that are used to direct the source beam 524A and/or the guide beams 524B as desired through the coupling optics 582 so the guide beams 524B are coupled into selected light guides 522A in any desired manner.

Additionally, during use of the multiplexer alignment system 542, as shown in FIG. 5, the probe source beam 570A from the second energy source 570 is initially directed toward the second beamsplitter 572, from where at least a portion of the probe source beam 570A is directed onward toward the first beamsplitter 568. Subsequently, based on the design of the first beamsplitter 568, the probe source beam 570A is redirected by the first beamsplitter 568 and toward the first movable redirector 584. From here, the probe source beam 570A follows the same path as described above for the source beam 524A and/or the guide beams 524B as they are ultimately directed and focused onto the light guides 522A. In particular, as illustrated, the first movable redirector 584 is configured to redirect the probe source beam 570A toward the second movable redirector 586, which then redirects the probe source beam 570A toward the coupling optics 582. The coupling optics 582 then direct and focus the probe source beam 570A toward the guide coupling housing 550. By adjusting the angles of each of the first movable redirector 584 and the second movable redirector 586 as described above, the probe source beam 570A can then be focused by the coupling optics 582 to scan across the face of the guide coupling housing 550 and/or the guide proximal end 522P of each of the light guides 522A in the light guide bundle 522.

As noted, in certain embodiments, as shown in FIG. 5, the catheter system 500 is controlled such that the probe source beam 570A is slightly offset from the individual guide beams 524B as they are scanned across the face of the guide coupling housing 550. More particularly, in such embodiments, the movable redirectors 584, 586 and the coupling optics 582 can be configured and/or positioned such that the probe source beam 570A slightly leads or is slightly ahead of the individual guide beams 524B during the scanning process. Stated in another manner, the movable redirectors 584, 586 and the coupling optics 582 are aligned such that the spot from the guide beam 524B is formed a controlled distance lagging the spot from the probe source beam 570A.

Further, similar to the previous embodiments, during the scanning process, at least a portion of the light in the focused spot from the probe source beam 570A scatters off the faces of the guide coupling housing 550 and the individual light guides 522A, and is directed back toward the coupling optics 582, the second movable redirector 586, the first movable redirector 584, and the first beamsplitter 568 as a backscattered energy beam 570B. After being focused and collimated by the coupling optics 582, and redirected by the second movable redirector 586 and the first movable redirector 584, the backscattered energy beam 570B is reflected off of and redirected by the first beamsplitter 568 toward the second beamsplitter 572, e.g., a 10/90 beamsplitter or another suitable type of beamsplitter (i.e. with different levels of transmittance and reflectance of the incident beam). The second beamsplitter 572 subsequently reflects a portion, e.g., most, of the light returned as the backscattered energy beam 570B onto the photodetector 576.

Additionally, in some embodiments, the photodetector 576 then generates a signal that is based on the portion of the visible light scattered from the faces of the guide coupling housing 550 and the individual light guides 522A, i.e. the portion of the backscattered energy beam 570B, which has been collected by the photodetector 576. As shown in FIG. 5, the signal from the photodetector 576 is then directed toward the amplifier 578 where the signal from the photodetector 576 is amplified. The amplified signal is thus utilized, e.g., within the signal processing electronics 526B, to determine the intensity of the backscattered energy beam 570B.

Further, as with the previous embodiments, when the intensity of the backscattered energy beam 570B is determined to be at a local minimum, i.e. by the signal processing electronics 526B, then it is determined that it is an appropriate time to fire the light source 524 so that a guide beam 524B is precisely directed and coupled onto the guide proximal end 522P of the desired light guide 522A. The signal processing electronics 526B and the control electronics 526A monitor and keep track of this information. More particularly, with the system controller 526 and/or the control electronics 526A controlling the speed of the scanning process, and with the offset between the probe source beam 570A and the individual guide beams 524B being known, the time between the optimal alignment for coupling the probe source beam 570A and time when the individual guide beams 524B will be at that location can be determined exactly. This allows the catheter system 500 to fully scan the face of the guide coupling housing 550 and/or the guide proximal end 522P of each of the light guides 522A to determine the location of optimal coupling and leave time to correctly position the spot and fire the light source 524 accordingly. It is appreciated that this general concept can be applied for having the light source 524 fire and have the individual guide beams 524B be precisely coupled onto the guide proximal end 522P of each of the light guides 522A in any suitable combination, order and/or pattern.

Figure 6:
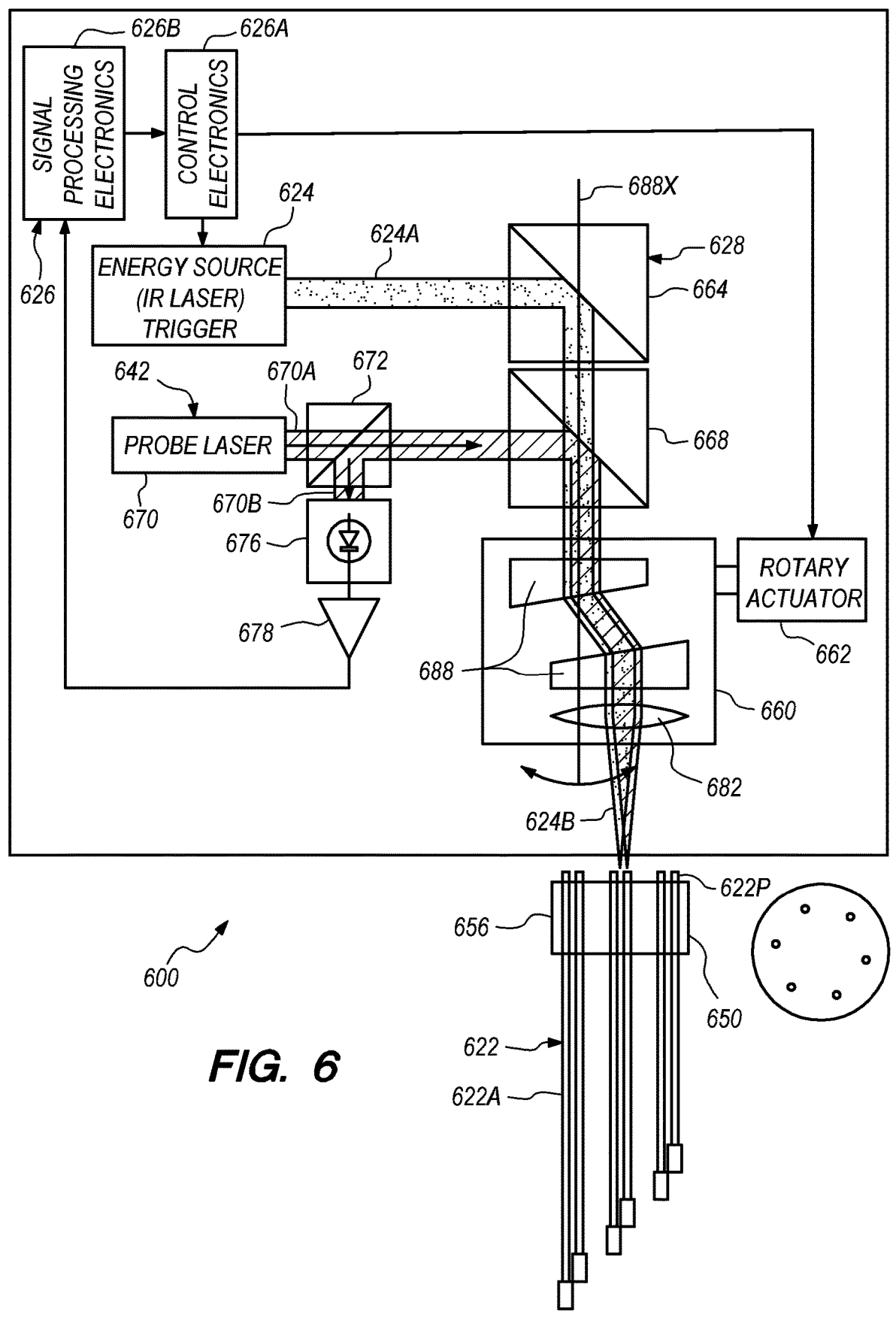
FIG. 6 is a simplified schematic illustration of a portion of yet another embodiment of the catheter system including yet another embodiment of the multiplexer and the multiplexer alignment system.

FIG. 6 is a simplified schematic illustration of a portion of yet another embodiment of the catheter system 600 including yet another embodiment of the multiplexer 628 and the multiplexer alignment system 642. In particular, as shown in FIG. 6, the catheter system 600 can include one or more of a light guide bundle 622 including a plurality of light guides 622A retained within a guide coupling housing 650; a light source 624 that generates a source beam 624A; a system controller 626 including control electronics 626A and signal processing electronics 626B; the multiplexer 628 and the multiplexer alignment system 642.

It is appreciated that the light guide bundle 622 can include any suitable number of light guides 622A, which can be positioned and/or oriented relative to one another in any suitable manner, e.g., to best align the plurality of light guides 622A relative to the multiplexer 628 and the multiplexer alignment system 642. For example, in the embodiment illustrated in FIG. 6, the light guide bundle 622 includes six light guides 622A that are aligned in a generally circular arrangement relative to one another, with the guide proximal end 622P of each of the light guides 622A being retained within guide coupling slots 656 within the guide coupling housing 650, i.e. a generally cylindrical-shaped guide coupling housing 650. The light guide bundle 622 and/or the light guides 622A are substantially similar in design and function as described in detail herein above. Accordingly, such components will not be described in detail in relation to the embodiment illustrated in FIG. 6.

As with the previous embodiments, the multiplexer 628 is configured to receive light energy in the form of the source beam 624A, e.g., a pulsed source beam, from the light source 624 and direct the light energy in the form of individual guide beams 624B onto the guide proximal end 622P of each of the plurality of the light guides 622A in any desired combination, order, sequence and/or pattern.

The design of the multiplexer 628 can be varied depending on the requirements of the catheter system 600, the relative positioning of the light guides 622A, and/or to suit the desires of the user or operator of the catheter system 600. In the embodiment illustrated in FIG. 6, the multiplexer 628 includes one or more of a redirector 664, a first beamsplitter 668, a multiplexer stage 660, a stage mover 662, a beam path adjuster 688, and coupling optics 682, which are used in conjunction with the system controller 626, i.e. the control electronics 626A and/or the signal processing electronics 626B, and the multiplexer alignment system 642 as described in detail herein. Alternatively, the multiplexer 628 can include more components or fewer components than those specifically illustrated in FIG. 6.

Additionally, as with the previous embodiments, the multiplexer alignment system 642 is configured to probe the face of the light guide bundle 622 (i.e. the face of the guide coupling housing 650) and/or the guide proximal end 622P of each of the light guides 622A in the light guide bundle 622 as a means to improve optical coupling between the guide beams 624B and the guide proximal end 622P of each of the light guides 622A.

The design of the multiplexer alignment system 642 can be varied depending on the requirements of the catheter system 600, the relative positioning of the light guides 622A, and/or to suit the desires of the user or operator of the catheter system 600. In the embodiment illustrated in FIG. 6, the multiplexer alignment system 642 includes one or more of the second light source 670, the first beamsplitter 668, a second beamsplitter 672, the beam path adjuster 688, the coupling optics 682, a photodetector 676 and an amplifier 678, which are used in conjunction with the system controller 626, i.e. the control electronics 626A and/or the signal processing electronics 626B, and the multiplexer 628. As described in detail herein, the second light source 670 provides light energy in the form of the probe source beam 670A that is directed to scan across the guide proximal end 622P of each of the light guides 622A during a mapping process. Alternatively, the multiplexer alignment system 642 can include more components or fewer components than those specifically illustrated in FIG. 6.

As above, in various embodiments, the multiplexer 628 and the multiplexer alignment system 642 are configured to operate substantially simultaneously, with the probe source beam 670A from the second light source 670 slightly leading the guide beams 624B from the light source 624, as both the probe source beam 670A and the individual guide beams 624B are scanning across the face of the guide coupling housing 650. Alternatively, in other embodiments, the multiplexer alignment system 642 can be configured to fully map out the face of the guide coupling housing 650 with the probe source beam 670A from the second light source 670 prior to any use of the light source 624 and the multiplexer 628 that are configured to direct and focus individual guide beams 624B onto the guide proximal end 622P of each of the light guides 622A in any desired sequence, order or pattern. The general operation of each of the multiplexer 628 and the multiplexer alignment system 642 in the embodiments shown in FIG. 6 will now be described in greater detail.

During use of the multiplexer 628, the source beam 624A from the light source 624 is initially directed toward and impinges on the redirector 664, which is configured to redirect the source beam 624A, e.g., by approximately 90 degrees or another suitable amount, toward the first beamsplitter 668, e.g., a dichroic beamsplitter. Subsequently, based on the design of the first beamsplitter 668, the source beam 624A is transmitted through the first beamsplitter 668 and toward the beam path adjuster 688.

As shown, the beam path adjuster 688 and the coupling optics 682 are mounted on and/or retained by the multiplexer stage 660. Additionally, as shown in the embodiment illustrated in FIG. 6, the stage mover 662 is configured to move the multiplexer stage 660 in a rotational manner. More particularly, in this embodiment, the multiplexer stage 660 and/or the stage mover 662 requires a single rotational degree of freedom. Additionally, as shown, the multiplexer stage 660 and/or the beam path adjuster 688 is aligned with the beam path of the source beam 624A from the redirector 664 on a rotational axis 688X. As such, the multiplexer stage 660 is configured to be rotated by the stage mover 662 about the rotational axis 688X.

During use of the catheter system 600, the source beam 624A is initially directed toward the multiplexer stage 660 along the rotational axis 688X. Subsequently, the beam path adjuster 688 is configured to deviate the source beam 624A a fixed distance laterally, i.e. off the rotational axis 688X, such that the source beam 624A is directed in a direction that is substantially parallel to and spaced apart from the rotational axis 688X. More specifically, the beam path adjuster 688 deviates the source beam 624A to coincide with the radius of the circular pattern of the light guides 622A in the guide coupling housing 650. As the multiplexer stage 660 is rotated, the source beam 624A that is directed through the beam path adjuster 688 traces out a circular path.

It is appreciated that the beam path adjuster 688 can have any suitable design. For example, in certain non-exclusive alternative embodiments, the beam path adjuster 688 can be provided in the form of an anamorphic prism pair, a pair of wedge prisms, or a pair of close-spaced right angle mirrors or prisms. Alternatively, the beam path adjuster 688 can include another suitable configuration of optics in order to achieve the desired lateral beam offset.

Additionally, as noted, the coupling optics 682 are also mounted on and/or retained by the multiplexer stage 660. As with the previous embodiments, the coupling optics 682 are configured to focus the individual guide beams 624B to each of the light guides 622A in the light guide bundle 622 retained, in part, within the guide coupling housing 650 for optimal coupling.

Further, during use of the multiplexer alignment system 642, as shown in FIG. 6, the probe source beam 670A from the second energy source 670 is initially directed toward the second beamsplitter 672, from where at least a portion of the probe source beam 670A is directed onward toward the first beamsplitter 668. Subsequently, based on the design of the first beamsplitter 668, the probe source beam 670A is redirected by the first beamsplitter 668 and toward the beam path adjuster 688. From here, the probe source beam 670A follows the same path as described above for the source beam 624A and/or the guide beams 624B as they are ultimately directed and focused onto the light guides 622A. In particular, as illustrated, the beam path adjuster 688 is configured to deviate the probe source beam 670A a fixed distance laterally, i.e. off the rotational axis 688X, such that the probe source beam 670A is directed in a direction that is substantially parallel to and spaced apart from the rotational axis 688X toward the coupling optics 682. The coupling optics 682 then direct and focus the probe source beam 670A toward the guide coupling housing 650. By rotating the multiplexer stage 660 with the stage mover 662 in a rotational manner as described above, the probe source beam 670A can then be focused by the coupling optics 682 to scan circularly about the face of the guide coupling housing 650 and/or the guide proximal end 622P of each of the light guides 622A in the light guide bundle 622.

In this embodiment, the stage mover 662 can have any suitable design for purposes of moving the multiplexer stage 660 in a rotational manner about the rotational axis 688X. More particularly, the stage mover 662 can be any suitable type of rotational mechanism. Additionally, in some embodiments, the stage mover 662 can be electronically controlled, e.g., using stepper motors or a piezo-actuated rotational stage, to line the beam path of the guide beam 624B sequentially with each individual light guide 622A that is retained, in part, within the guide coupling housing 650. Alternatively, in other embodiments, the stage mover 662 and/or the multiplexer stage 660 can be equipped with mechanical stops so that the coupling optics 682 can be precisely aligned with the position of each of the light guides 622A.

As noted, in certain embodiments, as shown in FIG. 6, the catheter system 600 is controlled such that the probe source beam 670A is slightly offset from the individual guide beams 624B as they are scanned about the face of the guide coupling housing 650. More particularly, in such embodiments, the beam path adjuster 688 and the coupling optics 682 can be configured and/or positioned such that the probe source beam 670A slightly leads or is slightly ahead of the individual guide beams 624B during the scanning process. Stated in another manner, the beam path adjuster 688 and the coupling optics 682 are aligned such that the spot from the guide beam 624B is formed a controlled distance lagging the spot from the probe source beam 670A.

Further, similar to the previous embodiments, during the scanning process, at least a portion of the light in the focused spot from the probe source beam 670A scatters off the faces of the guide coupling housing 650 and the individual light guides 622A, and is directed back toward the coupling optics 682, the beam path adjuster 688, and the first beamsplitter 668 as a backscattered energy beam 670B. After being focused and collimated by the coupling optics 682, and redirected by the beam path adjuster 688, the backscattered energy beam 670B is reflected off of and redirected by the first beamsplitter 668 toward the second beamsplitter 672, e.g., a 10/90 beamsplitter or another suitable type of beamsplitter (i.e. with different levels of transmittance and reflectance of the incident beam). The second beamsplitter 672 subsequently reflects a portion, e.g., most, of the light returned as the backscattered energy beam 670B onto the photodetector 676.

Additionally, in some embodiments, the photodetector 676 then generates a signal that is based on the portion of the visible light scattered from the faces of the guide coupling housing 650 and the individual light guides 622A, i.e. the portion of the backscattered energy beam 670B, which has been collected by the photodetector 676. As shown in FIG. 6, the signal from the photodetector 676 is then directed toward the amplifier 678 where the signal from the photodetector 676 is amplified. The amplified signal is thus utilized, e.g., within the signal processing electronics 626B, to determine the intensity of the backscattered energy beam 670B.

Further, as with the previous embodiments, when the intensity of the backscattered energy beam 670B is determined to be at a local minimum, i.e. by the signal processing electronics 626B, then it is determined that it is an appropriate time to fire the light source 624 so that a guide beam 624B is precisely directed and coupled onto the guide proximal end 622P of the desired light guide 622A. The signal processing electronics 626B and the control electronics 626A monitor and keep track of this information. More particularly, with the system controller 626 and/or the control electronics 626A controlling the speed of the scanning process, and with the offset between the probe source beam 670A and the individual guide beams 624B being known, the time between the optimal alignment for coupling the probe source beam 670A and time when the individual guide beams 624B will be at that location can be determined exactly. This allows the catheter system 600 to fully scan the face of the guide coupling housing 650 and/or the guide proximal end 622P of each of the light guides 622A to determine the location of optimal coupling and leave time to correctly position the spot and fire the light source 624 accordingly. It is appreciated that this general concept can be applied for having the light source 624 fire and have the individual guide beams 624B be precisely coupled onto the guide proximal end 622P of each of the light guides 622A in any suitable combination, order and/or pattern.

Alternatively, although FIG. 6 illustrates that the light guides 622A are fixed in position relative to the multiplexer stage 660, in some embodiments, it is appreciated that the light guides 622A can be configured to move, e.g., rotate relative to coupling optics 682 that are fixed in position. In such embodiments, the guide coupling housing 650 itself would move, e.g., the guide coupling housing 650 can be rotated about the rotational axis 688X, and the system controller 626 can control the rotational stage to move in a stepped manner so that the light guides 622A are each aligned, in a desired pattern, with the coupling optics and the guide beams 624B. The multiplexer alignment system 642 would need to monitor the position of this stage and determine motion for the projected guide spot from the light source 624 while scanning and determining location for optimal coupling. The system controls the stage and steps it to align a light guide 622A with the guide beam 624B and coupling optics 682 when the determined position for optimal coupling was reached. In such embodiment, the guide coupling housing 650 would not be continuously rotated, but would be rotated a fixed number of degrees and then counter-rotated to avoid the winding of the light guides 622A.

Figure 7:
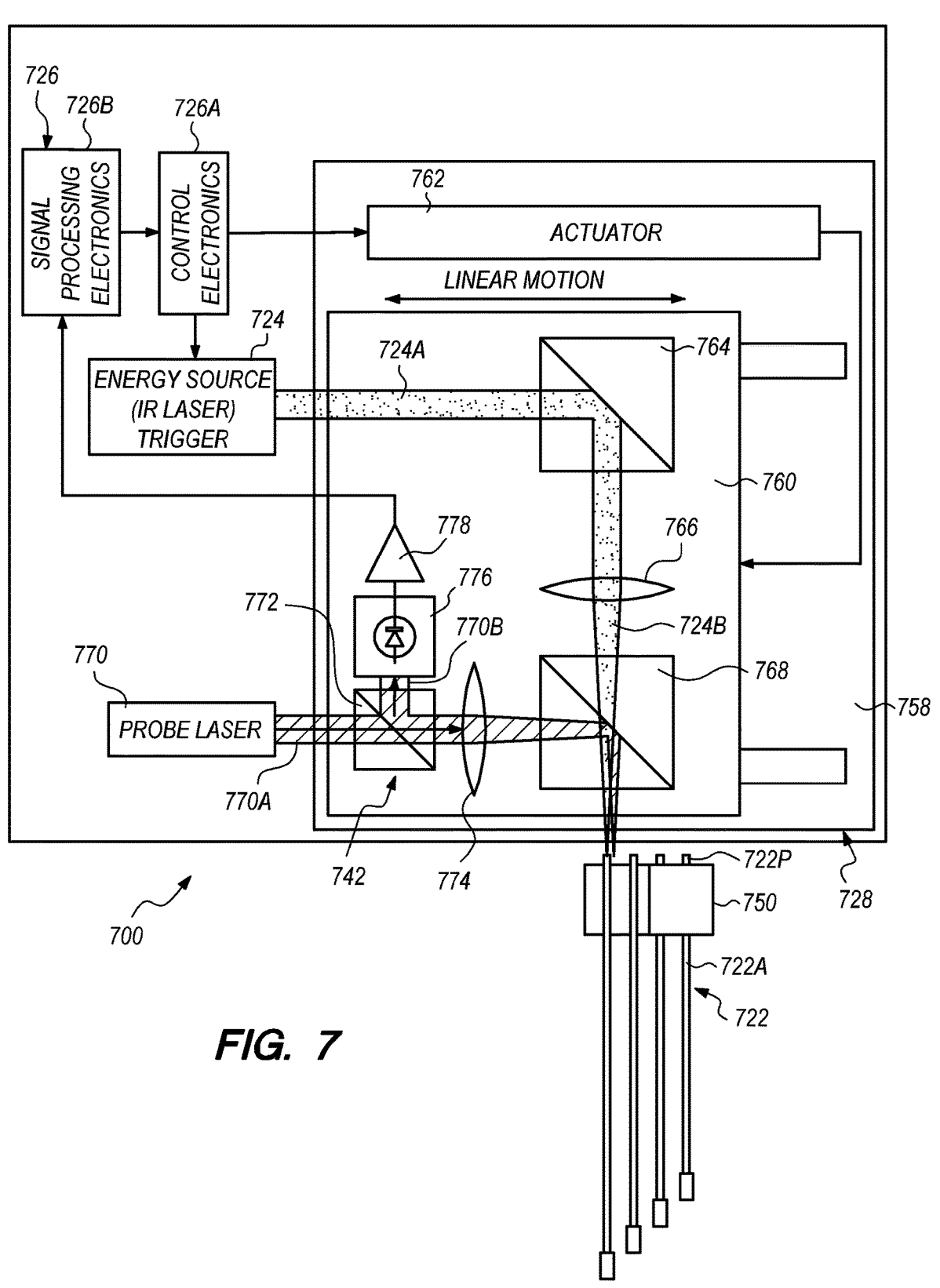
FIG. 7 is a simplified schematic illustration of a portion of still yet another embodiment of the catheter system including still yet another embodiment of the multiplexer and the multiplexer alignment system.

FIG. 7 is a simplified schematic illustration of a portion of still yet another embodiment of the catheter system 700 including still yet another embodiment of the multiplexer 728 and the multiplexer alignment system 742. As illustrated, the embodiment of the catheter system 700 illustrated in FIG. 7, including the multiplexer 728 and the multiplexer alignment system 742 is substantially similar to the catheter system 200 as illustrated and described in relation to FIG. 2. For example, as shown, the catheter system 700 again includes a light guide bundle 722 including a plurality of light guides 722A retained within a guide coupling housing 750; a light source 724 that generates a source beam 724A; a system controller 726 including control electronics 726A and signal processing electronics 726B; the multiplexer 728 and the multiplexer alignment system 742.

It is appreciated that the light guide bundle 722 can include any suitable number of light guides 722A, which can be positioned and/or oriented relative to one another in any suitable manner, e.g., to best align the plurality of light guides 722A relative to the multiplexer 728 and the multiplexer alignment system 742. For example, in the embodiment illustrated in FIG. 4, the light guide bundle 722 again includes four light guides 722A that are aligned in a generally linear arrangement relative to one another, with the guide proximal end 722P of each of the light guides 722A being retained within the guide coupling housing 750. The light guide bundle 722 and/or the light guides 722A are substantially similar in design and function as described in detail herein above. Accordingly, such components will not be described in detail in relation to the embodiment illustrated in FIG. 7.

As noted, the multiplexer 728 and the multiplexer alignment system 742 are substantially similar in design and function to what was described in detail herein above in relation to FIG. 2. In particular, the multiplexer 728 again includes one or more of a multiplexer base 758, a multiplexer stage 760, a stage mover 762, a redirector 764, coupling optics 766, and a first beamsplitter 768, which are used in conjunction with the system controller 726, i.e. the control electronics 726A and/or the signal processing electronics 726B, and the multiplexer alignment system 742. Additionally, the multiplexer alignment system 742 again includes one or more of a second light source 770 that generates a probe source beam 770A, the first beamsplitter 768, a second beamsplitter 772, an optical element 774, a photodetector 776 and an amplifier 778, which are used in conjunction with the system controller 726, i.e. the control electronics 726A and/or the signal processing electronics 726B, and the multiplexer 728.

However, in this embodiment, the mode of operation of the catheter system 700 is somewhat different in that the scanning process for each of the multiplexer alignment system 742 and the multiplexer 728 are conducted independently from one another. In particular, in such embodiment, the catheter system 700 is configured such that the multiplexer alignment system 742 conducts a full scanning and mapping of the faces of the guide coupling housing 750 and/or the guide proximal ends 722P of each of the light guides 722A with the probe source beam 770A from the second light source 770 which is scattered back at least partially as the backscattered energy beam 770B, without the multiplexer 728 scanning with individual guide beams 724B as well substantially simultaneously. Thus, in such embodiment, the multiplexer alignment system 742 would scan through every light guide 722A and find the X-Y location for each light guide 722A that gives optimal coupling, and do this without firing the main light source 724. It could go slowly and do a thorough X-Y scan across the face of the guide coupling housing 750 and map the whole thing out. Such information would then be stored in the control electronics 726A, with such information on locations being subsequently used for real-time firing of the primary light source 724. In this embodiment, the multiplexer alignment system 742 could still utilize the second light source 770 such as shown in FIG. 7. Alternatively, the multiplexer alignment system 742 could also be configured to use the same light source 724 as is being used and manipulated by the multiplexer 728.

In application of this alternative embodiment, the catheter system 700 could be used following the steps of: 1) user inserts guide coupling housing 750 into the system console 123 (illustrated in FIG. 1), 2) the catheter system 700 locks the guide coupling housing 750 in place and switches to standby mode, 3) the multiplexer alignment system 742 scans across the face of the guide coupling housing 750 following some X-Y pattern (zig-zag, etc.) mapping out the location for optimal coupling for each light guide 722A, 4) the system controller 726 and/or the control electronics 726A stores all of those locations and switches over to ready mode, 5) the user actuates the catheter 102 (illustrated in FIG. 1) and the multiplexer 728 scans across face of the guide coupling housing 750 and stops at each optimal X-Y location and fires the light source 724.

Although the embodiment described in FIG. 7 is shown as being employed within an embodiment that is substantially similar to that illustrated and described in relation to FIG. 2, it is appreciated that such alternative mode of operation of the multiplexer and the multiplexer alignment system can be utilized with any of the embodiments illustrated and described herein.

As described in detail herein, in various embodiments, the multiplexer and the multiplexer alignment system can be utilized to solve one or more of the problems that exist in more traditional catheter systems. For example:

1) The multiplexer and the multiplexer alignment system reduce optical coupling dependence on the precision and mechanical tolerance stack-ups of assemblies and true alignment for the light guides, the guide coupling housing, and associated connections, thereby making it possible to use low-cost, low-precision components on the single-use device and improve cost of goods sold.

2) The multiplexer and the multiplexer alignment system reduce the multiplexer performance dependence on the accuracy of the positioning mechanism in the multiplexer and associated quality and precision of its optical and mechanical components thereby improving speed and performance of the multiplexer and the overall catheter system.

It should be noted that, as used in this specification and the appended claims, the singular forms "a," "an," and "the" include plural referents unless the content and/or context clearly dictates otherwise. It should also be noted that the term "or" is generally employed in its sense including "and/or" unless the content or context clearly dictates otherwise.

It should also be noted that, as used in this specification and the appended claims, the phrase "configured" describes a system, apparatus, or other structure that is constructed or configured to perform a particular task or adopt a particular configuration. The phrase "configured" can be used interchangeably with other similar phrases such as arranged and configured, constructed and arranged, constructed, manufactured and arranged, and the like.

The headings used herein are provided for consistency with suggestions under 37 CFR 1.77 or otherwise to provide organizational cues. These headings shall not be viewed to limit or characterize the invention(s) set out in any claims that may issue from this disclosure. As an example, a description of a technology in the "Background" is not an admission that technology is prior art to any invention(s) in this disclosure. Neither is the "Summary" or "Abstract" to be considered as a characterization of the invention(s) set forth in issued claims.

The embodiments described herein are not intended to be exhaustive or to limit the invention to the precise forms disclosed in the following detailed description. Rather, the embodiments are chosen and described so that others skilled in the art can appreciate and understand the principles and practices. As such, aspects have been described with reference to various specific and preferred embodiments and techniques. However, it should be understood that many variations and modifications may be made while remaining within the spirit and scope herein.

It is understood that although a number of different embodiments of the catheter systems have been illustrated and described herein, one or more features of any one embodiment can be combined with one or more features of one or more of the other embodiments, provided that such combination satisfies the intent of the present invention.

While a number of exemplary aspects and embodiments of the catheter systems have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope, and no limitations are intended to the details of construction or design herein shown.

What is claimed is:

1. A catheter system for treating a treatment site within or adjacent to a vessel wall or heart valve, the catheter system comprising:

a first light source that is configured to generate a source beam;

a plurality of light guides that are each configured to alternatively receive the source beam from the first light source, each light guide having a guide proximal end;

a multiplexer that is configured to receive the source beam from the first light source, the multiplexer being configured to alternatively direct the source beam from the first light source to each of the plurality of light guides;

a multiplexer alignment system that is operatively coupled to the multiplexer, the multiplexer alignment system including a second light source that is configured to generate a probe source beam, a second beamsplitter, and a photodetector, the probe source beam being configured to produce a backscattered energy beam that is scattered off of the guide proximal end of each of the plurality of light guides, the second beamsplitter being configured to receive the backscattered energy beam and direct at least a portion of the backscattered energy beam toward the photodetector, the photodetector being configured to generate a signal based at least in part on the at least a portion of the backscattered energy beam that is directed toward the photodetector;

a first beamsplitter that is configured to receive (i) the source beam from the first light source, and (ii) the probe source beam from the second light source, the first beamsplitter being configured to direct the probe source beam and the source beam toward the guide proximal end of each of the plurality of light guides with the probe source beam laterally offset a known distance from the source beam; and a system controller that is configured to:

cause the second light source to generate the probe source beam toward the first beam splitter;

cause the multiplexer alignment system to scan the probe source beam across the guide proximal end of each of the plurality of light guides at a known speed;

receive the signal from the photodetector based on the backscattered energy beam;

determine a start time to generate the source beam based on the signal generated by the photodetector, the known distance, and the known speed so that the source beam is optically coupled to the guide proximal end of a light guide of the plurality of light guides when the first light source generates the source beam; and cause the first light source to generate the source beam at the start time.

2. The catheter system of claim 1 wherein the multiplexer alignment system is operatively coupled to the multiplexer so that the probe source beam is directed to scan across the guide proximal end of each of the plurality of light guides at a predetermined time prior to the source beam being directed toward the guide proximal end of each of the plurality of light guides.

3. The catheter system of claim 1 wherein the multiplexer alignment system further includes coupling optics that are configured to focus the probe source beam to scan across the guide proximal end of each of the plurality of light guides.

4. The catheter system of claim 3 wherein the multiplexer is configured to utilize the coupling optics to alternatively focus the source beam on the guide proximal end of each of the plurality of light guides.

5. The catheter system of claim 1 wherein the first beamsplitter includes a dichroic beamsplitter.

6. The catheter system of claim 1 wherein the first beamsplitter is configured to transmit one of the source beam and the probe source beam and to reflect the other of the source beam and the probe source beam.

7. The catheter system of claim 1 further comprising an amplifier and signal processing electronics; and wherein the amplifier is configured to amplify the signal from the photodetector to provide an amplified signal that is directed to the signal processing electronics to determine an intensity of light energy contained within the backscattered energy beam.

8. The catheter system of claim 7 wherein the system controller is configured to evaluate the intensity of light energy contained within the backscattered energy beam and determine optimal optical coupling between the probe source beam and the plurality of light guides.

9. The catheter system of claim 1 wherein the multiplexer includes (i) a multiplexer base, (ii) a multiplexer stage that is movably supported on the multiplexer base, (iii) a stage mover that is configured to move the multiplexer stage in a single linear degree of freedom relative to the multiplexer base in response to a signal from the system controller, and (iv) a redirector that is mounted on the multiplexer stage; and wherein movement of the multiplexer stage relative to the multiplexer base is configured to result in corresponding movement of the redirector relative to the multiplexer base.

10. The catheter system of claim 9 wherein the multiplexer further includes coupling optics that are mounted on the multiplexer stage, the coupling optics being configured to alternatively focus the source beam on the guide proximal end of each of the plurality of light guides; and wherein the source beam being received by the multiplexer initially impinges on the redirector, the redirector being configured to redirect the source beam toward the coupling optics.

11. The catheter system of claim 1 wherein the plurality of light guides includes at least a first light guide and a second light guide; and wherein the system controller is configured to alternatingly direct the probe source beam and the source beam toward the guide proximal end of each of the first light guide and the second light guide so that (i) the probe source beam scans across the guide proximal end of the first light guide, (ii) the source beam subsequently scans across the guide proximal end of the first light guide, (iii) the probe source beam scans across the guide proximal end of the second light guide, and (iv) the source beam subsequently scans across the guide proximal end of the second light guide.

12. The catheter system of claim 1 wherein system controller is configured to cause the source beam to be directed to the proximal end of the light guide while the causing the probe source to scan across the guide proximal end of each of the plurality of light guides.

13. A catheter system for treating a treatment site within or adjacent to a vessel wall or heart valve, the catheter system comprising:

a first light source that is configured to generate a source beam;

a plurality of light guides that are each configured to receive the source beam from the first light source, each light guide having a guide proximal end, the plurality of light guides including at least a first light guide and a second light guide;

a multiplexer that is configured to receive the source beam from the first light source, the multiplexer being configured to direct the source beam from the first light source to each of the plurality of light guides;

a multiplexer alignment system that is operatively coupled to the multiplexer, the multiplexer alignment system including: a second light source that is configured to generate a probe source beam that is configured to be directed by the multiplexer alignment system; a first beamsplitter that is configured to receive (i) the source beam from the first light source, and (ii) the probe source beam from the second light source, the first beamsplitter being configured to direct the probe source beam and the source beam toward the guide proximal end of each of the first light guide and the second light guide with the source beam at a known offset distance from the probe source beam so that (i) the probe source beam scans across the guide proximal end of the first light guide, (ii) the source beam subsequently scans across the guide proximal end of the first light guide, (iii) the probe source beam scans across the guide proximal end of the second light guide, and (iv) the source beam subsequently scans across the guide proximal end of the second light guide, the probe source beam being configured to scan across the guide proximal end of each of the plurality of light guides to produce a backscattered energy beam that is scattered off of the guide proximal end of each of the plurality of light guides; and a photodetector that is configured to generate a signal based at least in part on the at least a portion of the backscattered energy beam that is directed toward the photodetector; and a system controller that is configured to analyze the signal generated by the photodetector to determine optical coupling between the probe source and the plurality of light guides and cause the first light source to generate the source beam at a start time to optically couple the source beam with the proximal end of one or both of the first light guide and the second light guide, the start time being determined by the system controller based on the signal generated by the photodetector and the known offset distance.

14. The catheter system of claim 13 wherein the plurality of light guides are retained at least partially within a guide coupling housing; and wherein the probe source beam is configured to be directed by the system controller to scan across a face of the guide coupling housing.

15. The catheter system of claim 14 wherein the guide proximal end of each of the plurality of light guides is retained within the guide coupling housing.

16. The catheter system of claim 13 wherein at least one of the first light source and the second light source includes a laser.

17. The catheter system of claim 13 wherein the multiplexer alignment system further includes coupling optics that are configured to focus the probe source beam to scan across the guide proximal end of each of the plurality of light guides.

18. The catheter system of claim 17 wherein the multiplexer is configured to utilize the coupling optics to alternatively focus the source beam on the guide proximal end of each of the plurality of light guides.

19. The catheter system of claim 13 wherein the first beamsplitter includes a dichroic beamsplitter.

20. A catheter system for treating a treatment site within or adjacent to a vessel wall or heart valve, the catheter system comprising:

a first light source that is configured to generate a source beam;

a second light source that is configured to generate a probe source beam;

a plurality of light guides that are each configured to receive the source beam from the first light source, each light guide having a guide proximal end, the plurality of light guides including at least a first light guide and a second light guide;

a multiplexer that is configured to receive the source beam, the multiplexer being configured to alternatively direct the source beam to each of the plurality of light guides;

a first beamsplitter that is configured to receive (i) the source beam from the first light source, and (ii) the probe source beam from the second light source, the first beamsplitter being configured to direct the probe source beam and the source beam toward the guide proximal end of each of the first light guide and the second light guide with the source beam at a known offset distance from the probe source beam so that (i) the probe source beam scans across the guide proximal end of the first light guide, (ii) the source beam subsequently scans across the guide proximal end of the first light guide, (iii) the probe source beam scans across the guide proximal end of the second light guide, and (iv) the source beam subsequently scans across the guide proximal end of the second light guide, the probe source beam being configured to produce a backscattered energy beam that is scattered off of the guide proximal end of each of the plurality of light guides;

a photodetector that is configured to generate a signal based at least in part on the at least a portion of the backscattered energy beam that is directed toward the photodetector; and a system controller that is configured to:

cause the probe source beam to scan across one or both of the first light and the second light guide at a known speed;

analyze the signal generated by the photodetector to determine optical coupling between the probe source beam and the plurality of light guides; and cause the first light source to generate the source beam at a start time, the starting being determined by the system controller based on determining an optical coupling between the probe source beam and the proximal end of one of the first light guide and the second light guide, the known offset distance, and the known speed.

* * * * *